US012640245B2

(12) United States Patent
Minkus

(10) Patent No.: US 12,640,245 B2
(45) Date of Patent: May 26, 2026

(54) SYSTEM FOR REMOTE PERITONEAL DIALYSIS EXCHANGES

(71) Applicants:VANTIVE US HEALTHCARE LLC, Deerfield, IL (US); VANTIVE HEALTH GMBH, Glattpark (CH)

(72) Inventor: Marc Steven Minkus, Bannockburn, IL (US)

(73) Assignees: Vantive US Healthcare LLC, Deerfield, IL (US); Vantive Health GMBH, Glattpark (CH)

( * ) Notice: Subject to any disclaimer, the term of this patent is extended or adjusted under 35 U.S.C. 154(b) by 72 days.

(21) Appl. No.: 17/500,466

(22) Filed: Oct. 13, 2021

(65) Prior Publication Data

US 2022/0036989 A1      Feb. 3, 2022

Related U.S. Application Data

(63) Continuation of application No. 14/204,852, filed on Mar. 11, 2014, now Pat. No. 11,170,883.

(Continued)

(51) Int. Cl.
*G16H 20/10*          (2018.01)
*A61L 2/00*          (2006.01)
(Continued)

(52) U.S. Cl.
CPC ................ *G16H 20/10* (2018.01); *A61L 2/00* (2013.01); *A61L 9/00* (2013.01); *A61M 1/155* (2022.05); *A61M 1/159* (2022.05); *A61M 1/1657* (2022.05); *A61M 1/1674* (2014.02); *A61M 1/168* (2013.01); *A61M 1/1682*

(2014.02); *A61M 1/1686* (2013.01); *A61M 1/28* (2013.01); *A61M 1/282* (2014.02); *A61M 1/284* (2014.02);

(Continued)

(58) Field of Classification Search
None
See application file for complete search history.

(56) References Cited

U.S. PATENT DOCUMENTS

| 4,085,046 A | 4/1978 | Saporito |
| 4,560,472 A | 12/1985 | Granzow et al. |

(Continued)

FOREIGN PATENT DOCUMENTS

| CA | 2905393 C | 4/2020 | |
| DE | 19520916 A1 * | 1/1997 | .......... A61M 1/1656 |

(Continued)

OTHER PUBLICATIONS

Japanese Office Action and English translation for related Japanese Application No. 2019-151185; action dated Jun. 28, 2022; (6 pages).

(Continued)

*Primary Examiner* — Benjamin L Lebron
*Assistant Examiner* — Eric J McCullough
(74) *Attorney, Agent, or Firm* — K&L Gates LLP

(57)          ABSTRACT

A peritoneal dialysis system includes (i) a fill container, and (ii) an energizing unit that removably accepts the fill container, the energizing unit including a sterilization source so configured and arranged relative to the fill container when accepted by the energizing unit to place fluid within the fill container in a physiologically safe condition for delivery to the peritoneal cavity of a patient.

14 Claims, 24 Drawing Sheets

Related U.S. Application Data

(60) Provisional application No. 61/917,739, filed on Dec. 18, 2013, provisional application No. 61/784,562, filed on Mar. 14, 2013.

(51) Int. Cl.

| | |
|---|---|
| *A61L 9/00* | (2006.01) |
| *A61M 1/14* | (2006.01) |
| *A61M 1/16* | (2006.01) |
| *A61M 1/28* | (2006.01) |
| *G16H 20/40* | (2018.01) |

(52) U.S. Cl.
CPC ............ *A61M 1/288* (2014.02); *G16H 20/40* (2018.01); *A61M 2205/11* (2013.01)

(56) References Cited

U.S. PATENT DOCUMENTS

| | | | |
|---|---|---|---|
| 4,596,551 A | 6/1986 | Golinski et al. | |
| 4,747,822 A | 5/1988 | Peabody | |
| 5,015,389 A * | 5/1991 | Portillo, Jr. ......... | A61M 1/1656 |
| | | | 424/686 |
| 5,094,748 A | 3/1992 | Portillo | |
| 5,591,344 A | 1/1997 | Kenley et al. | |
| 5,851,384 A * | 12/1998 | Shen ................... | A61M 1/1657 |
| | | | 422/106 |
| 5,944,684 A | 8/1999 | Roberts et al. | |
| 6,491,658 B1 | 12/2002 | Miura | |
| 10,350,343 B2 | 7/2019 | Minkus | |
| 2003/0155531 A1 * | 8/2003 | Clark ........................ | A61L 2/24 |
| | | | 250/492.1 |
| 2009/0009179 A1 | 1/2009 | Sobue et al. | |
| 2009/0182263 A1 * | 7/2009 | Burbank ............... | A61J 1/2003 |
| | | | 210/767 |
| 2009/0299273 A1 | 12/2009 | Lee et al. | |
| 2009/0309835 A1 | 12/2009 | Levin et al. | |
| 2010/0010428 A1 | 1/2010 | Yu et al. | |
| 2011/0120035 A1 | 5/2011 | Staebler | |
| 2012/0071815 A1 * | 3/2012 | Childers ................. | A61M 1/28 |
| | | | 604/29 |
| 2012/0203570 A1 | 8/2012 | Medvitz et al. | |
| 2014/0074506 A1 | 3/2014 | Oliver et al. | |
| 2014/0316332 A1 | 10/2014 | Lo et al. | |

FOREIGN PATENT DOCUMENTS

| | | | | |
|---|---|---|---|---|
| DE | 69530904 T2 | 1/2004 | | |
| DE | 102006019390 A1 * | 10/2007 | ............... | A61L 2/04 |
| EP | 2331165 B1 | 11/2017 | | |
| EP | 3495005 B1 | 1/2021 | | |
| EP | 3824920 A1 | 5/2021 | | |
| WO | 00/57935 A1 | 10/2000 | | |
| WO | 2005/0066872 A2 | 7/2005 | | |
| WO | 2010/135078 A2 | 11/2010 | | |
| WO | 2012/095301 A1 | 1/2012 | | |

OTHER PUBLICATIONS

Canadian Office Action dated Aug. 31, 2022; Examination Search Report dated Aug. 30, 2022; Canadian Patent Application No. 3,074,091; 3 Pages.

Ng et al., "In-Centre Intermittent Peritoneal Dialysis: A viable interim option to an eventual definitive renal replacement therapy?", Med J Malaysia vol. 67 No. 2 Apr. 2012, pp. 151-154.

J.A.M.A., Jun. 20, 1959, vol. 170, No. 8, pp. 91-98: "Peritoneal Dialysis—Technique and Applications".

American Journal of Kidney Diseases, vol. 27, No. 6 (June), 1996: pp. 844-847: "Self-Delivery of Hemodialysis Care: A therapy in itself".

Peritoneal Dialysis International, vol. 31, pp. 121-126, 2011: "PD in the developing world—Advancing the use and quality of peritoneal dialysis by developing a peritoneal dialysis satellite center program".

American Journal of Kidney Diseases, vol. 35, No. 4 (April), 2000: pp. 638-643: "Patient Assessment of Quality of Care In a Chronic Peritoneal Dialysis Facility".

Central dialysis delivery system for the automatic peritoneal dialysis machine; Harold McDonald Jr and Richard essert 1965.

* cited by examiner

SYSTEM FOR REMOTE PERITONEAL DIALYSIS EXCHANGES

PRIORITY CLAIM

This application claims priority to and the benefit as a continuation of U.S. patent application Ser. No. 14/204,852, filed on Mar. 11, 2014, now U.S. Pat. No. 11,170,883, entitled, "System And Method For Peritoneal Dialysis Exchanges Having Reusable Energizing Unit", which claims priority to and the benefit of (i) U.S. Provisional Application No. 61/917,739, filed Dec. 18, 2013, entitled, "System And Method For Remote Peritoneal Dialysis Exchanges" and (ii) U.S. Provisional Application No. 61/784,562, filed Mar. 14, 2013, entitled, "System And Method For Remote Peritoneal Dialysis Exchanges", the entire contents of each of which are incorporated herein by reference and relied upon.

BACKGROUND

The present disclosure relates to peritoneal dialysis treatment. More specifically, the present disclosure relates to systems and methods of enabling convenient and inexpensive peritoneal dialysis treatment for multiple patients in a single location.

Many people suffer from renal disease, in which the kidneys do not adequately filter toxins and waste products from the blood. When kidney failure occurs, water and minerals become unbalanced in blood and tissues, and toxic end products of nitrogen metabolism (e.g., urea, creatinine, uric acid and others) can accumulate. A person with failed kidneys cannot continue to live without replacing at least the filtration functions of the kidneys.

Different forms of dialysis treatment are used to treat patients suffering from renal disease. One form of dialysis treatment is hemodialysis, in which the patient's blood is passed through an artificial kidney dialysis machine and cleansed before reentering the patient. Because hemodialysis is an extracorporeal procedure, there are certain limitations associated with the treatment. For example, treatment typically lasts several hours and is generally performed in a treatment center about three times per week.

A second form of dialysis treatment is peritoneal dialysis, in which the patient's own peritoneum is used as a semi-permeable membrane rather than an artificial kidney. One advantage to peritoneal dialysis is that patients can undertake treatment at home instead of visiting a medical facility or utilizing costly equipment associated with hemodialysis treatment.

When a patient undergoes peritoneal dialysis treatment, a dialysis solution is periodically infused into the peritoneum through an implanted catheter. Diffusion and osmosis exchanges take place between the dialysis solution and the bloodstream across the natural body membranes, which remove the water, toxins and waste products that the kidneys normally excrete. After a period of time, the used dialysis solution is drained from the peritoneum and replaced with fresh fluid. The period of time that the dialysis solution remains in the patient's peritoneum is referred to as the dwell time.

There are generally two types of peritoneal dialysis treatment: automated peritoneal dialysis ("APD") and continuous ambulatory peritoneal dialysis ("CAPD"). APD uses a dialysis machine to drain, fill and dwell dialysis solution from the peritoneum through an implanted catheter. Several drain, fill, and dwell cycles normally occur while the patient is connected to the dialysis machine. The main advantage of APD is that it is hands-free regarding the patient and can therefore be performed at night while the patient is asleep, freeing the patient during the day.

With CAPD, a dialysis solution is manually introduced into the peritoneum through an implanted catheter. During the dwell time, an exchange of solutes between the dialysis solution and the blood is achieved. Once this exchange is achieved, the patient manually drains the dialysis solution from the peritoneum and manually replaces the drained solution with fresh fluid. This process is repeated per a doctor's prescription. One advantage to CAPD is that patients do not need a machine as gravity is used to fill and drain the patient.

Regardless of whether the patient performs APD or CAPD, the patient's prescription may call for a midday exchange. During a midday exchange, the patient drains used dialysate from the patient's peritoneum and fills the peritoneum with a fresh supply of dialysate. The midday exchange can be cumbersome especially for a patient at work. If the patient cannot return home, then the patient has to find a place at work to perform the procedure. The solution and disposables needed to perform the procedure also need to be available at work. The transfer and storage of the materials and the procedure may be awkward or embarrassing for the patient.

A need exists accordingly for an improved peritoneal dialysis treatment, especially for single exchanges, such as midday exchanges.

SUMMARY

The present disclosure seeks to solve these and other needs by providing a system and method to enable multiple patients to receive a peritoneal dialysis treatment at a remote location such that the patients do not have to store fresh dialysis solution or related supplies at home or work. The present system and method are useful for example for patients that do not have time to return home to perform dialysis treatment during the day. The system and method are useful for patients in developing countries and low income areas that do not have access to or the means to have dedicated home dialysis equipment. The system and method also provide effective peritoneal dialysis treatment to numerous patients in a convenient and cost effective manner. For example, the system and method can be used by a patient with a hectic work or daily schedule, allowing the patient to stop off at a facility according to the present disclosure on the way to or from work, during work, or during or in conjunction with other daily activities. A busy patient can use home equipment in combination with a facility according to the present disclosure to optimize his or her time, for example, by stopping at a facility for a fill (or drain and fill) session and then performing a subsequent drain (or drain and fill) session upon returning home at some time later.

The system and method include a facility. The facility includes a plurality of peritoneal dialysis treatment stations or rooms. Each treatment station or room is capable of performing one or more peritoneal dialysis patient exchange. It is contemplated to provide the dialysis stations or rooms with electrical and/or entertainment equipment, such as televisions, computers, headphones, tablets, Internet access, and the like, so that the patient can be entertained or perform work during the exchange, and possibly over an extended period if the patient performs multiple exchanges. Thus, a patient may leave work, go to the facility, and perform an exchange while logging into the patient's internal work website to continue work.

A facility can be located alternatively at a worksite, so that patients can conveniently receive treatment before, during or after work without disrupting their work schedules. A facility can further alternatively be located within or nearby a housing unit, at a train station, bus station or airport, or at a hostel or other temporary dwelling location, for example, to allow residents of the unit or dwelling to receive convenient treatment without having to own their own dialysis equipment or store their own disposable supplies. Such a facility is especially useful in developing countries in which most residents do not have the means for or access to dedicated home dialysis equipment. Certain countries, for example in Asia, provide temporary dwelling locations near work, so that employees can live near work during the week and return home on the weekend. The facilities of the present disclosure can be located at or near any such temporary dwelling locations.

It is contemplated for each facility to have a front desk or entry area. Patient visits to the facility can be by appointment and/or allow for walk-in business. The patient in an embodiment carries a computer readable medium having the patient's therapy prescription or other patient identification that allows the patient's prescription to be verified. Once verified, the patient is allowed into a treatment area of the facility, connected to a correct type of filling apparatus, e.g., batch or bagged, and provided with prescribed disposable supplies. The patient then proceeds to a designated exchange station, which may be covered by, e.g., curtains or cubicle dividers.

The exchange stations can include an automated peritoneal dialysis ("APD") machine, such as a HomeChoice™ or HomeChoicePro™ machine provided by the assignee of the present disclosure. The stations can alternatively be configured to provide a continuous ambulatory peritoneal dialysis ("CAPD") treatment. In an embodiment, the facility provides both in-center APD and CAPD stations to meet the needs of any operational dialysis prescription.

Both APD and CAPD treatments use a disposable set. The APD disposable set typically involves a disposable pumping cassette that is coupled to and operated by an APD machine. A plurality of tubes are connected to the disposable cassette. The tubes connect to the patient, a drain, and to one or more supply bag of peritoneal dialysis solution or dialysate. The CAPD disposable set is typically simpler because the set does not need to interact with a machine. The set includes a plurality of tubes for connecting to the patient, the drain, and one or more dialysis fluid supply. The set may use a manually operated valve to switch between cycles or instead use manual pinch clamps.

The patient whether using bagged solution or batch solution is provided with the correct amount and type of dialysis solution. In a CAPD treatment, once the patient enters the treatment area, the patient manually drains his or her effluent dialysis fluid, and then manually fills his or her peritoneum with dialysis solution provided by the facility. In an in-center APD treatment, the patient proceeds to a designated dialysis machine. The patient is provided with a cassette for the machine, which is loaded into the machine to perform one or more automatic exchanges.

The drain at each facility can include a large community or house drain. The community or house drain allows multiple patients to quickly drain to a common tank or basin. Structure and methodology are provided to ensure sterile connection to and disconnection from the common drain, which is also the case with large dialysate storage vessels or multi-treatment fill containers discussed in detail below. For example, the treatment area can provide sterilization units (e.g., UV-radiation) or sterilization agents (e.g., rubbing alcohol) for sterile connection. The treatment areas may also provide weigh scales, blood pressure cuffs and sample collection bags and associated analyzers, which may all be used to enhance treatment and patient care.

The patient can alternatively drain into a single patient drain container or bag. In either of the community or single drain container situations, it is contemplated to enable a sample of the patient's effluent to be taken. It is expressly contemplated for the facility to perform onsite effluent analysis if the patient desires and/or if the patient's prescription calls for an effluent analysis to be performed. The facility's house drain complies with any regulations regarding the disposal of biowaste. Likewise, the facility is equipped to properly dispose of the effluent waste containers and the used disposable cassettes and sets.

Alternatively, instead of discarding the used dialysate, a portion or all of the effluent dialysate may be regenerated into useable dialysate, e.g., using a sorbent system. The sorbent system removes undesirable components from effluent dialysate absorbed from the patient (e.g., toxins, fibrin and metabolic wastes), so that the dialysate can be used again. The sorbent system can also add desirable components (e.g., dextrose, glucose, and/or salts) to the regenerated dialysate to reconstitute the dialysate and to maintain a desired osmotic gradient for ultrafiltration removal. Using a sorbent system to clean the effluent dialysate collected by the facility enables the facility to reduce the amount of fresh dialysate that must be ordered and stored. For example, a single patient can use several hundred liters of fresh dialysate every month, so even a small facility serving only one-hundred patients can reduce its inventory of fresh dialysate by thousands of liters per month if the facility has a sorbent system in place to regenerate used dialysate. Using a sorbent system to clean the effluent dialysate collected by the facility also reduces the amount of used fluid that is discarded to the environment.

Alternatively or in addition to sorbent regeneration, other forms of effluent cleaning for regeneration may be used, such as any one or more of electrodialysis ("ED"), electrodialysis reversal ("EDR"), electrodeionization ("EDI"), ultrafiltration, reverse osmosis filtering, ultraviolet radiation, or ozone. Ozone can be created online by subjecting oxygen to ultraviolet light. The ozone can then be drawn into the effluent stream, e.g., via a venture pump. Ozone tends not to store well under positive pressure.

The dialysis solution or dialysate can be bagged or be stored in a large storage vessel. Dialysate used at home or at work is typically bagged, and it is contemplated to use bagged dialysate at the facilities of the present disclosure. Alternatively or additionally, the dialysate can be stored in a large vessel that is common to multiple patients. The dialysates are provided in different varieties, e.g., have different dextrose and glucose levels, and are set for each individual patient per their prescription. A midday exchange may, for example, use a different dialysate than the patient's prescribed nighttime dialysate. It is accordingly contemplated to provide different vessels having dialysates with different glucose or dextrose levels.

The vessels may each have a plurality of outlets, which each connect to a different patient line, e.g., for gravity delivery. It is contemplated to place an ultraviolet ("UV") lamp about each outlet so that each new connection is sterilized before any fluid is allowed to flow to the patient. The UV lamps can be in the form of clamshells that open to allow connection and disconnection. After connection, the clamshells are closed and the connection is UV sterilized. The connections can alternatively or additionally be sterilized by other methods, for example, through the use of hydrogen peroxide vapor, gamma irradiation, peracetic acid, ethylene oxide, ethanol, formalin, glutaraldehyde, low energy electron beam and/or any other sterilization method known in the art. For safety, some of these sterilization methods may be performed in a room segregated from the patients.

Various embodiments herein are targeted for countries that do not have medical reimbursement, and in which patient's needing dialysis treatments may not be able to afford treatment. One major goal here is to reduce the amount of disposable waste and thus disposable cost as much as possible. One good way to reduce the amount of disposable waste is to refurbish and reuse components that touch fresh and spent dialysis fluid. Thus in multiple embodiments discussed below, a reusable drain container is provided. The reusable drain container is portable. The patient receives a dry, disinfected drain container upon entering the facility and returns the drain container filled with effluent fluid after a remote exchange has taken place.

In one implementation, the reusable drain container is coupled with a filled, sterilized and heated fill container and a reusable CAPD set. The patient receives all three reusable units upon entering the facility, transports same to a patient station, performs a remote PD exchange, and brings the used units back to the front desk of the facility for refurbishment. The patient may receive a deposit back for returning the units if a deposit is required to receive the units.

Each of the three units is then refurbished. In one embodiment, some or all of the drain container, fill container and CAPD set are sent to an offsite, e.g., central, location for disinfection, sterilization and for re-loading the fill container with sterilized dialysate. Alternatively, the drain container may be disinfected at the treatment facility. It is contemplated in this first implementation, however, that the equipment used to prepare and sterilize the dialysate and the fluid be located offsite, and that the facility maintain a minimal amount of equipment. For example, the facility may only need a larger warmer to warm the filled reusable fill containers and perhaps a hot water disinfection bath or unit to disinfect the reusable drain containers if merely disinfecting of the drain container (as opposed to sterilization) is acceptable. The majority of the refurbishing is done offsite with used units being shipped out of and refurbished units being shipped into the treatment facility daily.

It is further contemplated to provide a pouch that holds the CAPD set. The pouch releasably snaps onto the reusable drain container for shipment. The CAPD set may be configured to have three tubing legs, one running to the patient, a second leg running to the fill container, and a third leg running to the drain container. The three legs meet at a junction. A manual flow control device is provided at the junction to allow the patient to switch from a drain phase or sequence, to a flush phase or sequence (for priming), and then to a patient fill phase or sequence. The CAPD set may be configured alternatively to be a single line. Here, the patient connects the single line first to the patient and the drain container to perform a patient drain. The patient then disconnects the line from the drain container and reconnects the same end of the line to a fill container. The patient then performs a patient fill, perhaps needing to prime the patient line first by venting air through a hydrophobic vent provided in the single line CAPD set.

The single line CAPD set may be easier to disinfect and sterilize than the three-legged CAPD set. The drain line in particular may become filled with fibrin and other patient particulates. The single line CAPD set may be more easily flushed of such particulates. Also, the reconnection of the single line APD set to the patient for filling may push some of the particulates back to the patient prior to the end of patient fill, eliminating the need to remove those particles after the remote exchange is completed. Nevertheless, it is contemplated that the three-legged APD set can also be properly cleared of patient particulates and subsequently disinfected.

In another implementation, the reusable drain container is coupled with a permanent or semi-permanent filling system. That is, each CAPD patient station of a treatment facility is provided with a filling system that is mounted in place and is not transported back and forth to and from the front desk of the treatment facility. The filling system includes an energizing unit and a fill container. The fill container resides within the energizing unit and remains within the unit until it needs to be removed for cleaning, replacement or for some other infrequent purpose. The energizing unit is open along at least one surface so that the fill container can be easily removed from the unit. The energizing unit includes a control unit that controls a plurality of valves and records readings from a plurality of sensors. The valves and sensors are tethered to the energizing unit via electrical wiring, so that they can be moved and releasably coupled to the fill container during normal use and removed from the fill container when the container needs to be removed from the energizing unit for whatever reason. The valves pinch close or unpinch open tubing leading to and from the fill container to perform container fills and container dispenses. The sensors provide needed feedback to the control unit, such as liquid temperature and conductivity feedback.

The energizing unit in one embodiment includes a weigh scale that records how much liquid is delivered to and how much dialysate is dispensed from the fill container. The energizing unit includes other actuators depending upon what is needed. For example, if the liquid provided to the fill container is not sufficiently sterile, the energizing unit is equipped with a plurality of ultraviolet ("UV") lights that irradiate the liquid to perform the needed remaining sterilization. If the liquid provided to the fill container is not heated to body temperature, the energizing unit is provided with one or more heating coil that heats the liquid to a proper temperature. If the liquid provided to the fill container is purified water instead of dialysate, the fill container is provided with a removable cap to accept dialysate additives, e.g., granulated or powderized additives. The energizing unit's conductivity sensors send a signal to its control unit to confirm that the additive has been mixed with the proper volume of water. The additive can be provided in a tear-open packet.

A separate sterilizing unit can be provided in addition to the permanent or semi-permanent filling system. The sterilizing unit is used to provide any additional sterilization needed for the CAPD sets at the point and time of use. Either of the three-legged or single line CAPD sets can be used with the filling system and the sterilizing unit. The sterilizing unit can in turn be used with any embodiment described herein requiring PD set sterilization.

The sterilization unit in one embodiment includes a clamshell or hinged arrangement with a base and a lid. The base and lid are each provided with UV lights that irradiate and sterilize the CAPD sets. The patient sets the CAPD set into the base, closes the lid and presses a switch or button to begin the sterilization. In one embodiment, the UV irradiation takes place for a preset amount of time known to sterilize the CAPD set in a worse case scenario and then shuts down automatically. The patient can immediately remove the CAPD set for use. The sterilization unit's irradiation in combination with between-exchange disinfection (e.g., via hot water bath) eliminates the need for the CAPD set to be packaged in a sterilized bag, reducing disposable waste. The CAPD sets are reused, further reducing disposable waste.

The filling system, reused fill container, reused drain container and sterilization unit enable the treatment facility to be self-contained, that is, to not require shipments to or from a refurbishment center. The treatment facility in one embodiment need only have one or more backroom water purification unit, a backroom hot water bath disinfection system or unit and perhaps a backroom pre-heater for use in combination with the localized patient station filling systems and sterilization units. The only waste produced in one embodiment is the packet used to hold the granulated or powdered dialysate additives.

The systems and methods herein enable the patient to alternate between a home treatment and treatment at one or more peritoneal dialysis facility. The home treatment can be a PD treatment or a blood treatment, such as hemodialysis ("HD"). It has been proposed that a combination HD and PD regimen is beneficial. The PD facility may also be more convenient for an HD patient who is traveling on work or business.

One or more server computer can be connected over a web portal to the patient's home equipment and the various facilities to store data related to the patient's at home and in-facility treatments in an electronic medical record database. The database can be accessed each time the patient needs treatment to verify the parameters of the patient's prescription, and/or to verify or allow the patient to receive treatment at the facility. Thus, the patient may not need to carry a computer readable medium. The patient can instead be recorded to and located on the system. The system also allows the patient's physician to access and alter the patient's treatment. The patient's home equipment and the various facilities can both immediately receive that updated information and adjust the patient's treatment accordingly.

It should be appreciated however that the system does not have to be server based. Instead, the facility can use a computer for accepting and verifying a patient's prescription, e.g., via a flash drive or computer stick, and identify the patient's prescribed solution type and volume. This alternative facility can be used in developing countries and other areas in which a server based system and website is not feasible. In developing countries, some or all of the peristaltic treatment can be performed at a facility.

The present system and method allow the patient to receive convenient peritoneal dialysis treatment without having to return home throughout the day. The system and method can free the patient from having to store large quantities of dialysis solution at his or her home assuming, for example, that the patient performs all or most of all peritoneal dialysis exchanges at one of the treatment facilities of the present disclosure. If several treatment facilities are located throughout the patient's town or city of residence, the patient can likely find convenient access to peritoneal dialysis treatment regardless of what he or she has to do on a given day.

It is accordingly an advantage of the present disclosure to provide a system and method for performing remote peritoneal dialysis exchanges.

It is another advantage of the present disclosure to provide a system and method for providing convenient peritoneal dialysis exchanges.

It is a further advantage of the present disclosure to provide a system and method for performing peritoneal dialysis exchanges in combination with home peritoneal dialysis treatments.

It is yet another advantage of the present disclosure to provide a system and method for communicating treatment data from a remote peritoneal dialysis exchange facility to a patient's clinic or hospital.

It is yet a further advantage of the present disclosure to provide a system and method for providing remote peritoneal dialysis exchanges in which there are multiple, selectable ways of providing treatment.

It is still another advantage of the present disclosure to provide a system and method for providing remote peritoneal dialysis exchanges in a manner that reduces disposable waste.

It is still a further advantage of the present disclosure to provide a system and method for performing remote peritoneal dialysis exchanges in a safe and sterile manner.

Further still, it is an advantage of the present disclosure to provide a system and method for providing remote peritoneal dialysis exchanges that reuse dialysis fluid and/or make dialysis fluid online.

Still further, it is an advantage of the present disclosure to provide a peritoneal dialysis system and method that produces very little disposable waste or cost.

Still another advantage of the present disclosure is to provide peritoneal dialysis filling units and sterilization units that sterilize the treatment fluid and treatment sets at the point and time of use.

Still a further advantage of the present disclosure is to provide reusable fill containers, drain containers and CAPD sets that can be refurbished for reuse.

Additional features and advantages are described herein, and will be apparent from the following Detailed Description and Figures.

DETAILED DESCRIPTION

Treatment Facility Locations

Figure 1:
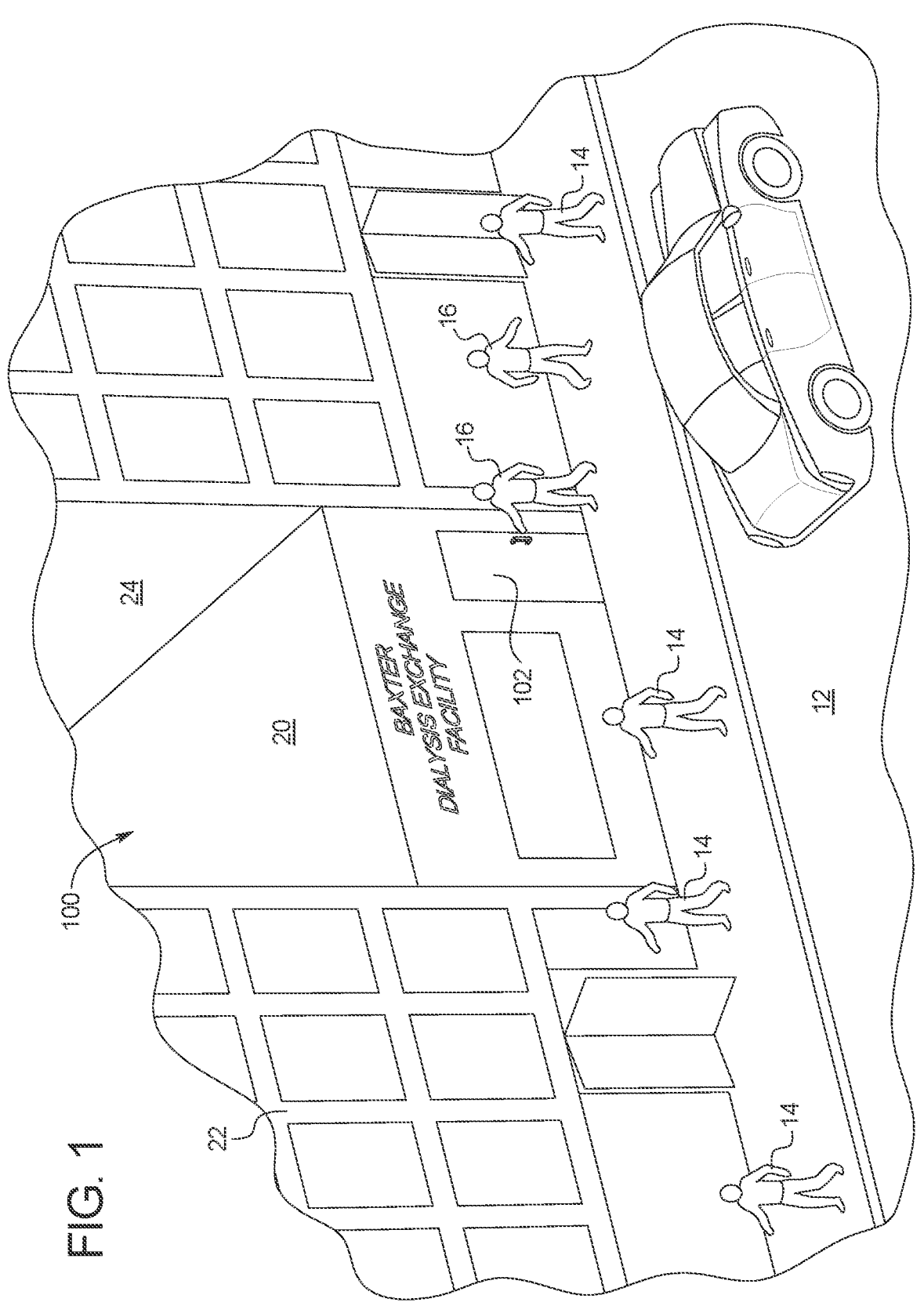
FIG. 1 is a perspective view of one embodiment for locating a peritoneal dialysis exchange facility of the present disclosure.

Referring now to the drawings and in particular to FIG. 1, one embodiment for locating a treatment facility 100 of the present disclosure is illustrated. It is contemplated to place treatment facility 100 in a large city and on a busy street 12, in which there is a large amount of travel of pedestrians 14, including one or more dialysis patient 16. Patients 16 can be strictly peritoneal dialysis ("PD") patients. It is contemplated however that if a doctor or clinician agrees, a patient who typically undergoes hemodialysis ("HD"), hemofiltration ("HF") or hemodiafiltration ("HDF") could also perform one or more PD exchange at facility 100. For example, a patient 16 traveling on business or vacation can perform a PD treatment at a facility 100 in place of the patient's normal treatment if it is more convenient to do so.

Street 12 in the illustrated embodiment is a busy street with much sidewalk traffic, providing a high amount of visibility to facility 100. In FIG. 1, treatment facility 100 is the sole business residing within a building 20 bounded by buildings 22 and 24. Facility 100 could alternatively be one of many businesses housed inside a larger building or sky rise, such as building 22 or 24. Street 12 can be a busy city street as illustrated or a suburban street or drive, for example, at a mall, strip mall, business park, or another high visibility location. Facility 100 can be located at or near a hospital, medical center or doctor's office if desired. Facility 100 can be marked clearly as illustrated in FIG. 1 or be generically adorned for discrete entry and exit.

Figure 10:
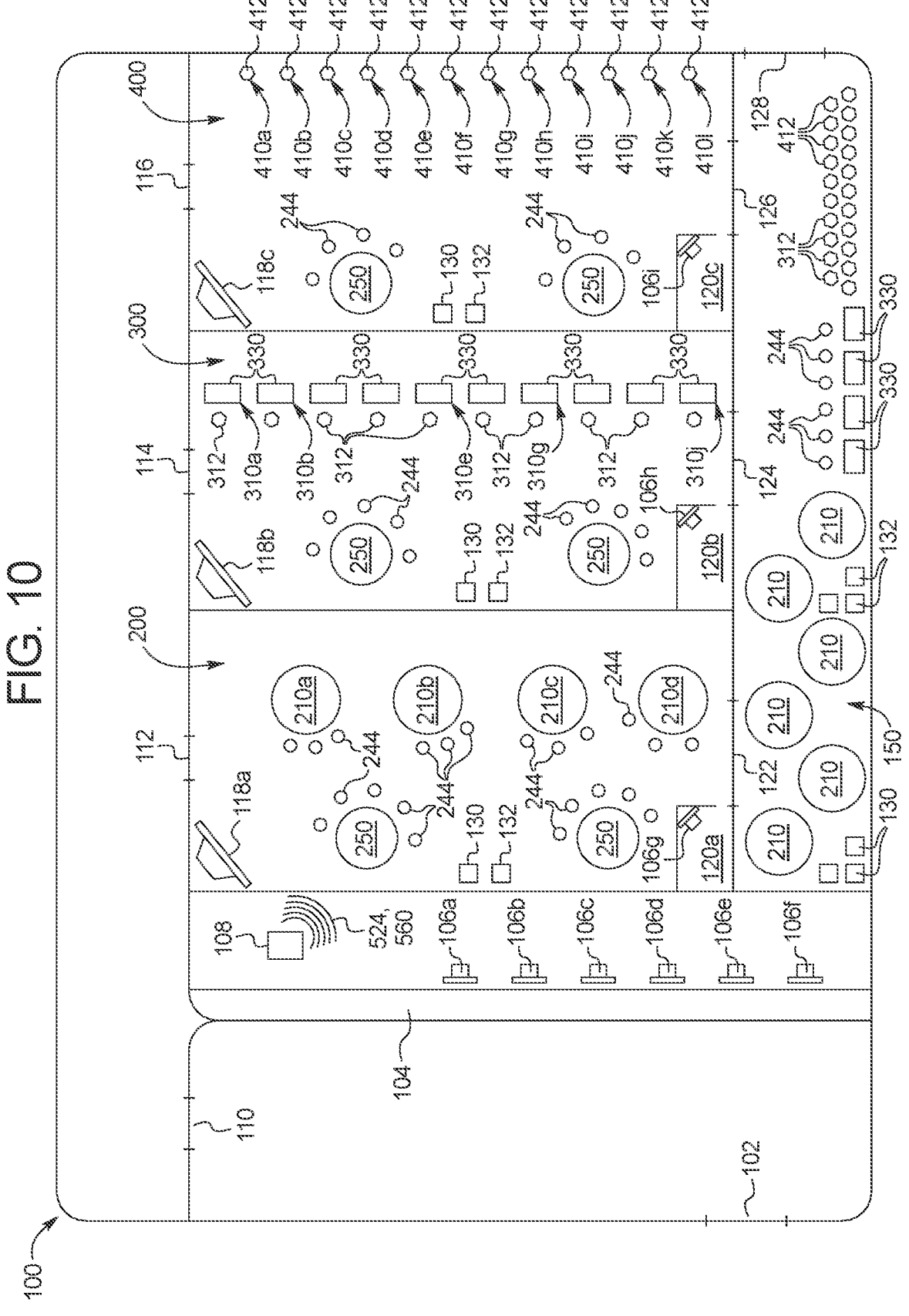
FIG. 10 is a plan view of one embodiment of a peritoneal dialysis exchange facility according to the present disclosure.

As discussed additionally in connection with FIG. 10, facility 100 includes a door 102 through which patients 16 enter and exit. Door 102 can be located on the outside of facility 100 as illustrated or be located inside of the building, down a hallway and on any floor of a building, such as a building full of doctor's offices. Door 102 can be opened freely by any pedestrian 14 or patient 16, or if desired, door 102 can be locked and provided with an automatic opener that patient 16 opens by sliding a card, or which is opened electronically by a person working inside of facility 100 upon the appearance of or door ell ring by patient 16.

Figure 2:
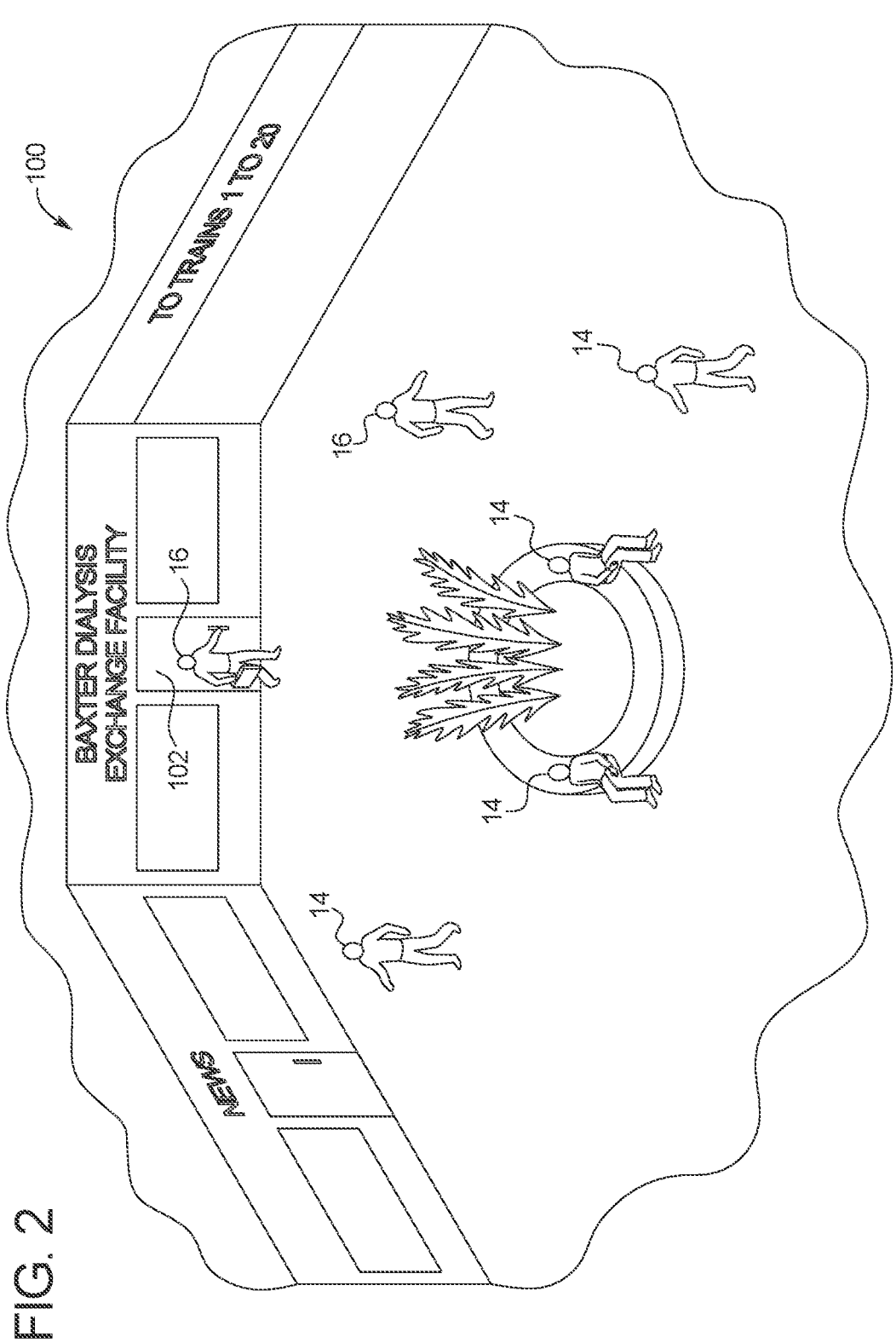
FIG. 2 is a perspective view of another embodiment for locating a peritoneal dialysis exchange facility of the present disclosure.

Referring now to FIG. 2, facility 100 is located alternatively inside of a building, here a train station or depot. It is expressly contemplated to place facilities 100 of the present disclosure at places of mass transit, such as train stations, bus stations, airports and the like, so that patients arriving at the location or departing from the location can perform one or more dialysis exchange upon arriving at the location, e.g., before heading to work, or before departing on a train, bus or airplane, etc., e.g., after work or before a long trip.

Certain countries have temporary dwelling or sleeping facilities that workers use during the week before returning home on the weekend. It is expressly contemplated to place facilities 100 at such locations or at hostels, hotels, nursing homes or condominium complexes. It is also expressly contemplated to place PD exchange facilities 100 at places of work, such as at a large factory or at a central location within an industrial park, so that people at work can take an hour or so to perform one or more dialysis exchange either before, during or after work (e.g., a midday exchange).

Treatment Facility Configurations

Figure 3:
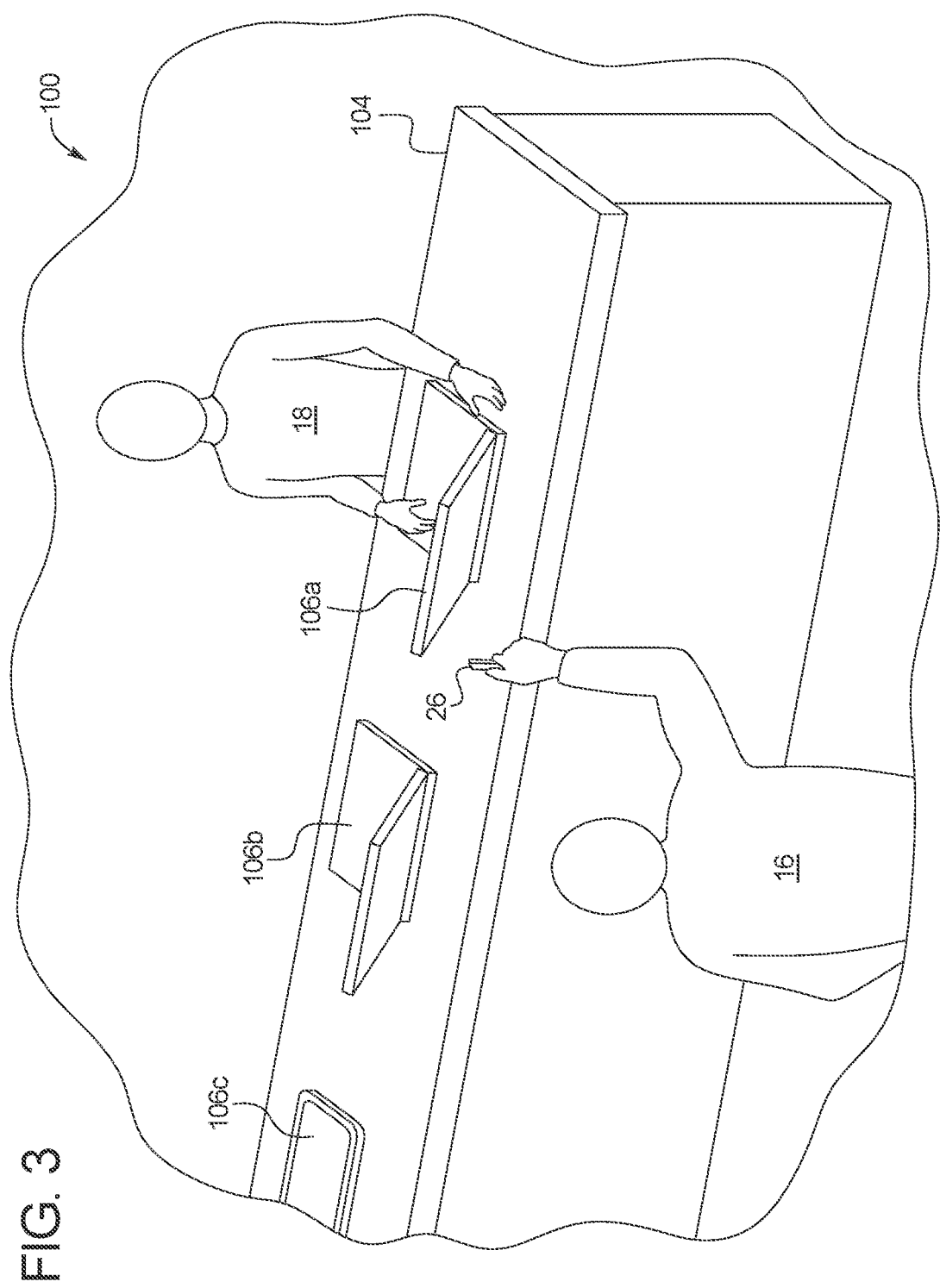
FIG. 3 is a perspective view of one embodiment for initiating a treatment session once a patient enters a peritoneal dialysis exchange facility of the present disclosure.

Referring now to FIG. 3, and as shown in conjunction with FIG. 10, once patient 16 enters facility through door 102, the patient encounters a desk 104 in one embodiment, and is able to speak with a facility professional 18 manning a computer 106a or 106b, smart tablet 106c, or some combination thereof. The interaction between patient 16 and facility professional 18 is described in more detail below in connection with FIGS. 10, 14 and 15, but generally the interaction is one in which facility professional 18 validates patient 16 and verifies that the patient is authorized, e.g., prescribed to, receive treatment at facility 100, and if so identifies the type of and parameters for the treatment. In the illustrated embodiment, patient 16 hands facility professional 18 a smart card, memory stick, flash drive or the like 26, which facility professional 18 inserts into or otherwise electronically connects to computers 106*a*, 106*b*, tablet 106*c* or some combination thereof. It is also contemplated to allow patient 16 to show a barcode or other marking using the patient's smart phone or tablet, which facility professional 18 visually scans at desk 104. Other structure and functionality for authorizing and/or verifying patient 16 is discussed below.

Figure 4:
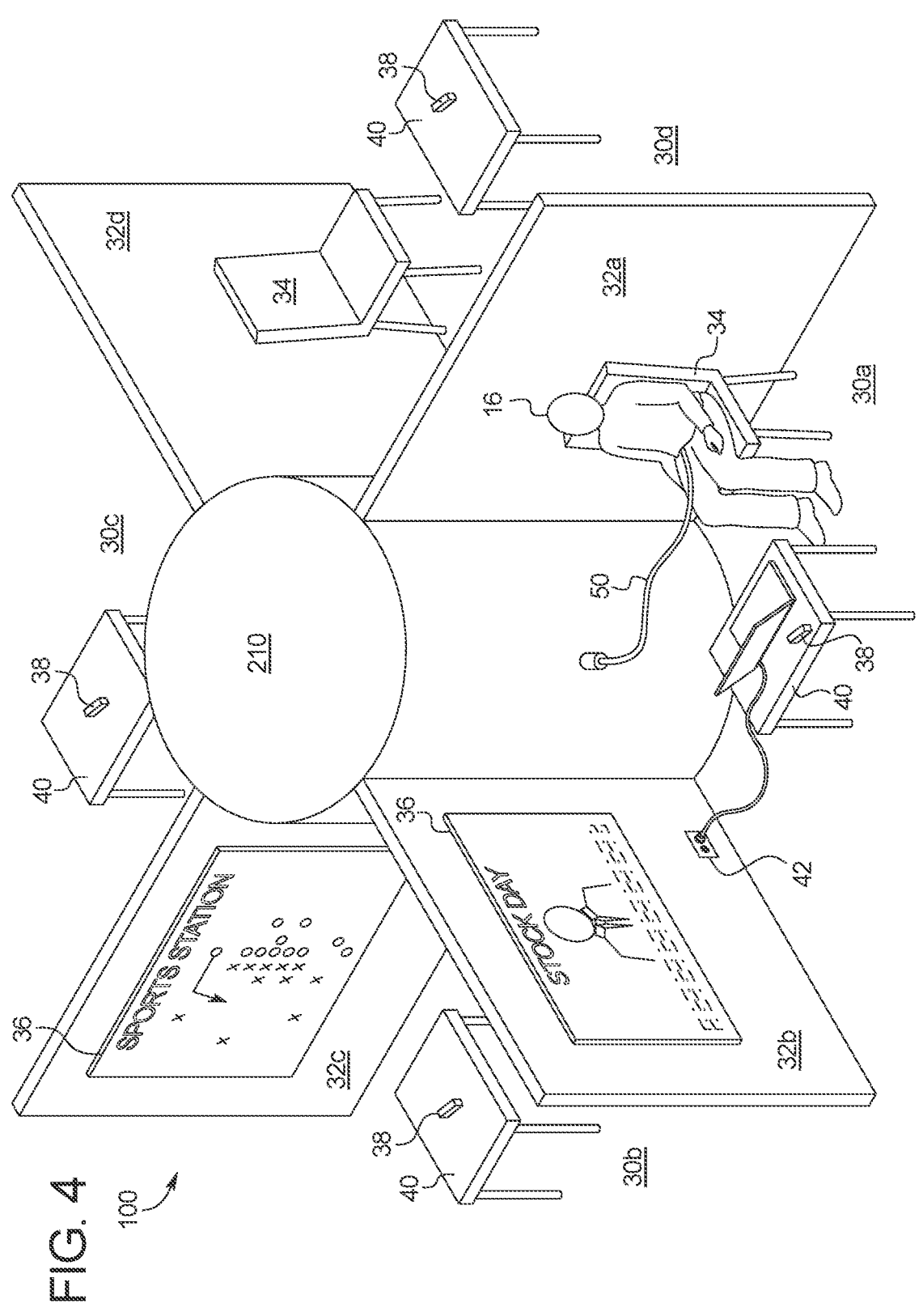
FIG. 4 is a perspective view of one embodiment for structuring a batch treatment area of an exchange facility of the present disclosure.

Referring now to FIG. 4, a large batch tank CAPD system is illustrated. Here, once patient 16 is authorized or verified at desk 104, patient 16 is allowed to enter a treatment area of facility 100. FIG. 4 illustrates one embodiment in which patient 16 receives dialysis fluid from a larger dialysis batch solution tank 210. Treatments involving larger dialysis batch solution tanks 210 are discussed in detail below in connection with FIGS. 10 and 11. For now, it is important to know that multiple patients 16 can perform exchanges simultaneously using a single larger dialysis solution tank 210.

In the illustrated embodiment, larger dialysis solution tank 210 is used as a hub from which a plurality of walls 32*a* to 32*d* extend to form a plurality of individual and semi-private patient stations 30*a* to 30*d*. More or less than four walls and patient stations may be formed for a given hub tank 210. Multiple hub tanks 210, each having separation walls and corresponding patient stations may be located behind the desk area 104 of a given facility 100. Although not illustrated, patient stations 30*a* to 30*d* may be enclosed by a curtain, wall and/or door, for example.

In the illustrated embodiment, each patient station 30*a* to 30*d* includes a chair, sofa, bed, or the like 34, which allows the patient to rest comfortably during the one or more PD exchange. The opposing wall from the wall against which chair, sofa, or bed 34 is placed can have a television or computer monitor 36 to provide entertainment and/or information to patient 16 during the one or more PD exchange. Television 36 is controlled via a remote control 38, which can be set on and/or stored in a desk or table 40, and which can all be provided in each patient station 30*a* to 30*d* in the illustrated embodiment. One or more wall outlet 42 can be provided for each patient station 30*a* to 30*d* to power the patient's personal computer, smart phone, tablet, combination computer/tablet, compact disk player, digital music player, portable television, and the like.

Figure 11:
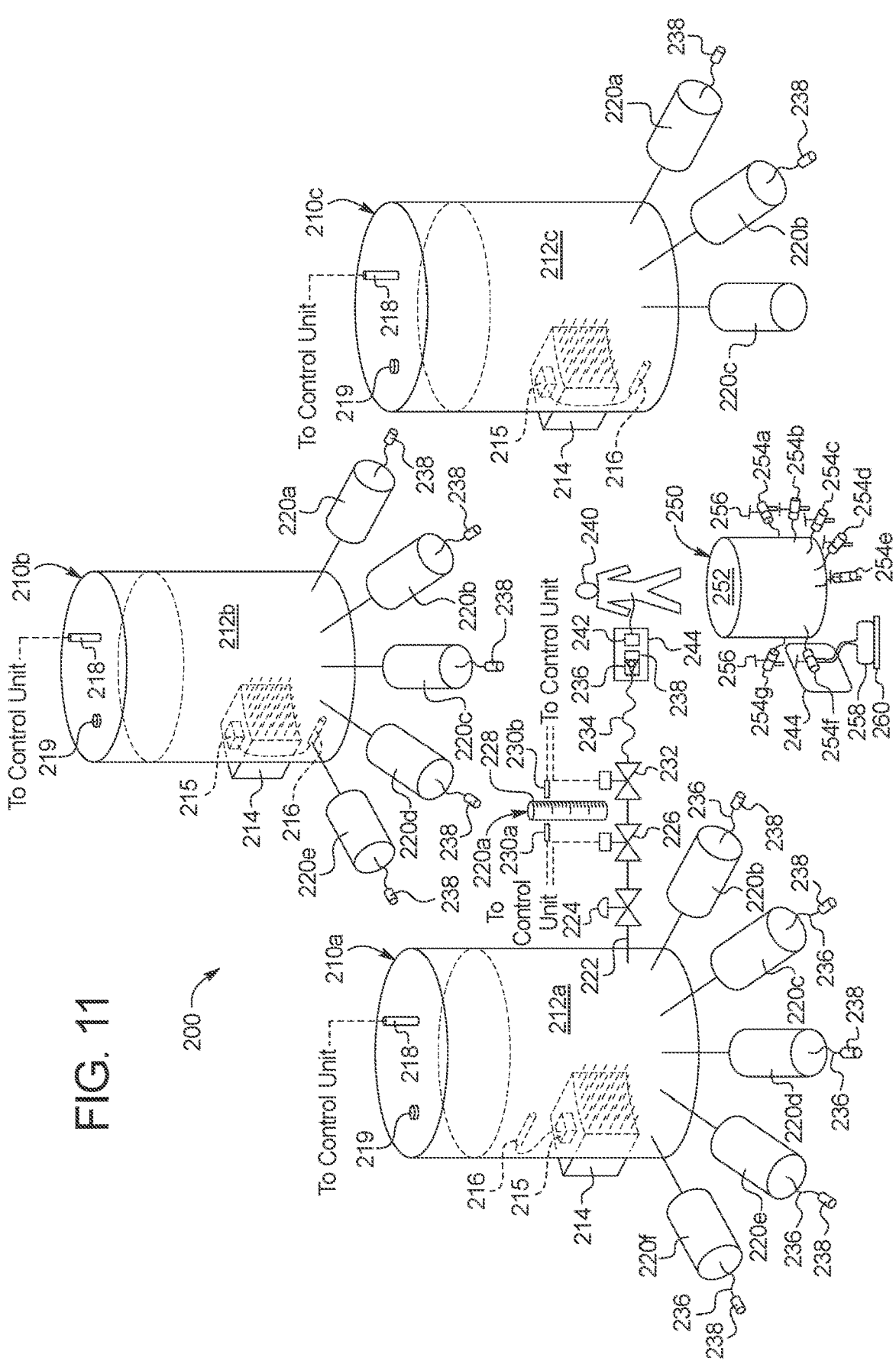
FIG. 11 is a perspective view for one embodiment of a batch peritoneal dialysis treatment area of a peritoneal dialysis exchange facility according to the present disclosure.

In the illustrated embodiment, each patient 16 at one of the patient stations 30*a* to 30*d* receives PD treatment fluid from larger dialysis solution tank 210 via a patient line 50. FIGS. 10 and 11 discuss in detail how PD treatment fluid can be metered through a dispenser 220*a*, 220*b*, etc., which acts as or replaces patient line 50 in FIG. 4. FIGS. 10 and 11 also discuss various ways in which patient 16 receiving treatment via larger dialysis solution tank 210 can drain effluent dialysate before a first PD exchange or between multiple PD exchanges.

Figure 5:
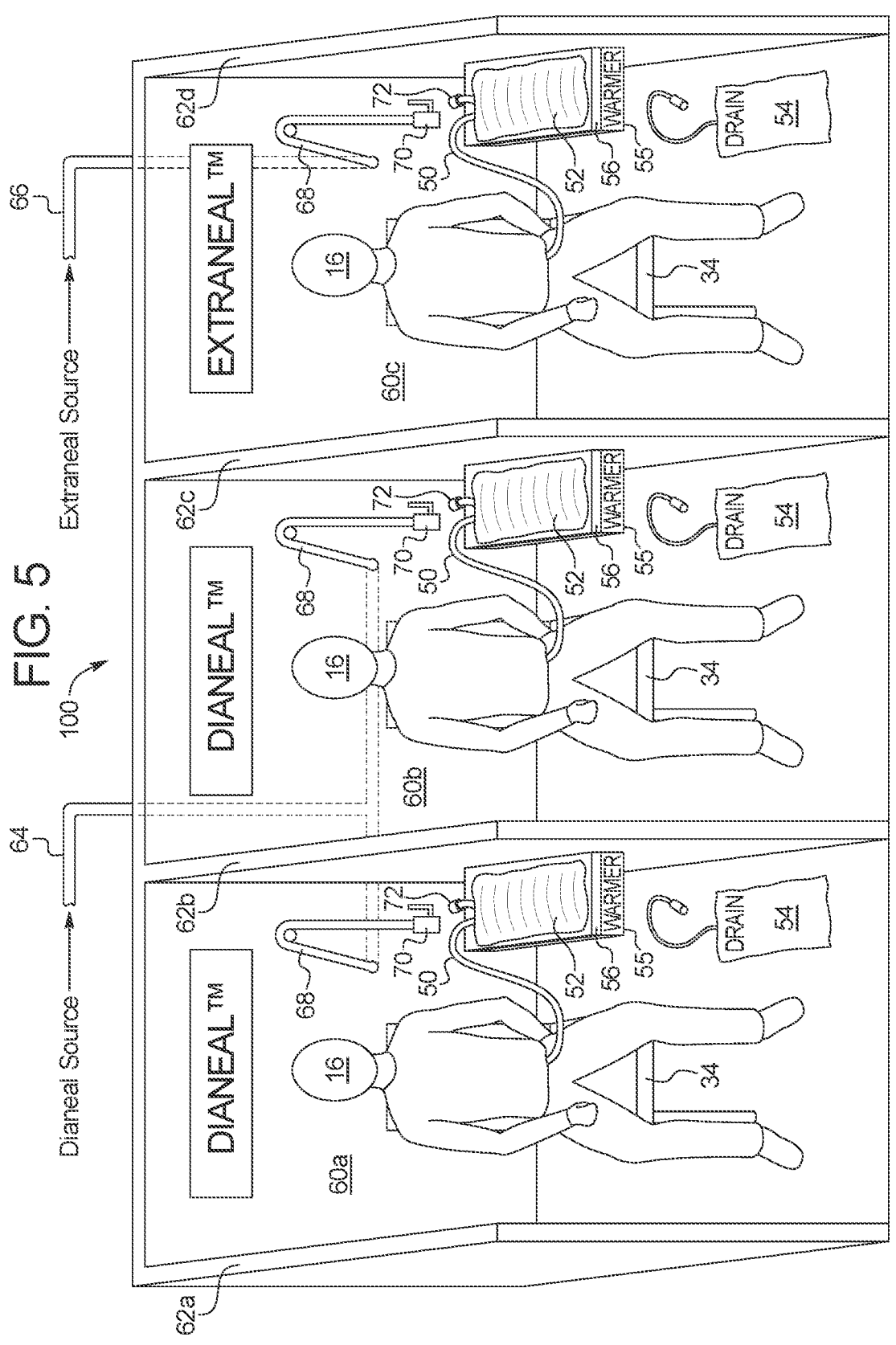
FIG. 5 is a perspective view of one embodiment for structuring a batch or a continuous ambulatory peritoneal dialysis ("CAPD") treatment area of an exchange facility of the present disclosure.

Referring now to FIG. 5, one bagged CAPD embodiment is illustrated. Once patient 16 is authorized or verified at desk 104, patient 16 is allowed to proceed to an alternative treatment facility 100, in which PD treatment fluid is fed initially to a patient bag 52 and then from patient bag 52, through patient line 50, to patient 16. In FIG. 5, alternative patient stations 60*a* to 60*c* (any number of which can be provided), divided by walls 62*a* to 62*d*, are horizontally juxtaposed as opposed to being laid out in a circular manner as is illustrated in FIG. 5. Any of the horizontal, circular or other geometrical patient station arrangements discussed herein can be used with any type of the PD fluid delivery mechanism (e.g., bagged, batch or online) discussed herein and/or with any type of effluent PD fluid draining mechanism (e.g., bagged or community drain) discussed herein.

Horizontally juxtaposed patient stations 60*a* to 60*c* can have any one, or more, or all of chair, sofa, bed, or the like 34, television 36, remote control 38, desk or table 40, and/or alternating current wall outlet 42 discussed above in connection with FIG. 4. Stations 60*a* to 60*c* can likewise be closed by a curtain, wall and/or door.

In the PD exchange embodiment of FIG. 5, patients 16 each drain to their own drain bag 54, e.g., to begin a first PD solution exchange or between multiple patient fills performed at facility 100. As discussed herein, patient drains may be to individual bags, such as bags 54, or to a common drain. Patient bags 52 are placed on a warmer 55, which may also be provided with a weigh scale 56 to weigh any one, or more, or all of fresh PD fluid delivered to patient 16, spent PD fluid removed from patient 16, and additional ultrafiltrate ("UF") fluid removed from the patient. UF can be determined for example by subtracting the total weight of fresh fluid delivered to patient 16 from the total weight of spent fluid removed from patient 16.

FIG. 5 introduces another feature of the present disclosure discussed in detail below, namely, that facility 100 can provide different types of dialysates for different patients 16 or for different times during a particular treatment. In FIG. 4, for example, different larger dialysis solution tanks 210 can hold dialysates of different dextrose or glucose levels. Likewise in FIG. 5, patient stations 60*a* and 60*b* are dedicated to patients receiving DIANEAL™ PD solution, while patient station 60*c* is dedicated to patients receiving EXTRANEAL™ PD solution. DIANEAL™ PD solution and EXTRANEAL™ PD solution are both marketed by the assignee of the present disclosure.

FIG. 5 illustrates that a manifold line 64 runs behind patient stations 60*a* to 60*d*, from a DIANEAL™ PD solution source, such as a larger dialysis solution tank 210, to solution lines 68 located inside patient stations 60*a* and 60*b*. A second manifold line 66 runs behind patient stations 60*a* to 60*c*, from an EXTRANEAL™ solution source, such as a larger dialysis solution tank 210, to a solution line 68 located inside patient station 60*c*. Patients 16 or a facility professionals 18 (FIG. 3) can connect solution lines 68 to fill ports 72 on patient bags 52 using valved connectors 70 when patient 16 first arrives at one of patient stations 60*a* to 60*c*. Once bags 52 are filled, valved connectors 70 are removed from fill ports 72 on patient bags 52. Patients 16 can then fill themselves from bags 52 whenever they are ready, e.g., by using a valve on the patient's transfer set, a valve on the patient end of patient line 50, and or by opening one or more pinch clamp (not illustrated) placed on patient line 50.

Please note that patient line 50, patient bag 52 and drain bag 54 form a structure similar to a continuous ambulatory peritoneal dialysis ("CAPD") disposable set 412 discussed below in connection with FIGS. 10 and 13. Indeed, CAPD could be performed using sets 412 in the patient stations 60*a* to 60*c* of FIG. 5 instead of the illustrated batch dialysis, which uses manifold lines 64 and 66.

As long as valved connectors 70 can be repeatedly aseptically connected to fill ports 72 on the patient bags 52, the patient bags can be used multiple times during a visit by patient 16. Patient 16 may accordingly fill multiple drain bags 54. In an embodiment, patient 16 or facility professional 18 (FIG. 3) removes patient bag 52 from scale 56 at the end of the patient's exchanges and places the one or more drain bag 54 sequentially or in combination on weigh scale 56 to record the patient's total drain weight. The patient's total fill weight is recorded prior to removing patient bag 52. The patient's in-session UF can thus be calculated by subtracting total fill weight from total drain weight. Different ways for recording and monitoring patient data produced at facilities 100 is discussed below.

Figure 6A:
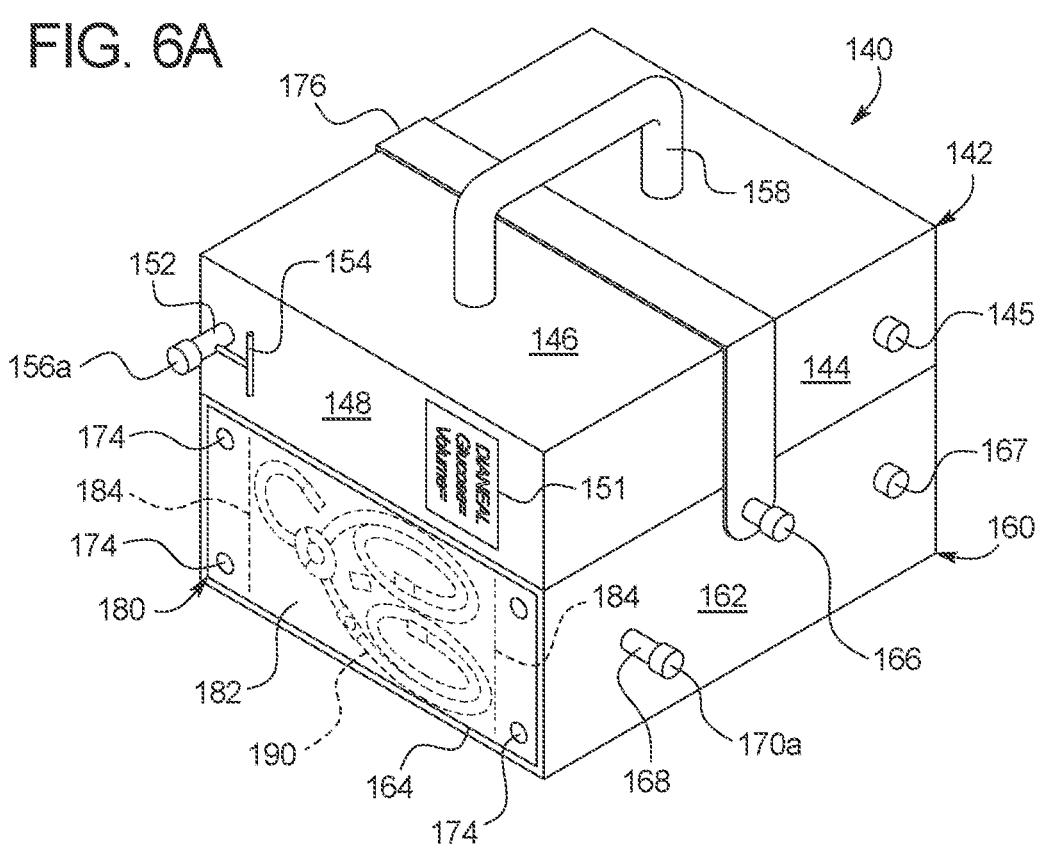
FIG. 6A is a perspective view of one embodiment for structuring a reusable supply and drain container system for a CAPD treatment area of an exchange facility of the present disclosure.

Referring now to FIG. 6A, a CAPD embodiment using a CAPD unit 140 that eliminates disposables is illustrated. In certain countries, patients are not reimbursed for dialysis treatments. It is especially important in such cases to keep costs low. One way of doing so is to reduce or eliminate disposable waste. Reusing and re-sterilizing components saves material costs and any costs associated with having to dispose of a potential biohazard. CAPD unit 140 is shown in an assembled form, which can be easily transported. CAPD unit 140 includes a reusable fill container 142 and a reusable drain container 160. Reusable fill container 142 and reusable drain container 160 can be made of the same or different materials and are made of a semi-rigid or rigid plastic in one embodiment.

In one embodiment, fill container 142 and drain container 160 are plastic, such as polypropylene ("PP"), high density polyethylene ("HDPE"), low density Polyethylene ("LDPE"), polycarbonate ("PC"), glycol-modified polyethylene terephthalate ("PET-G"), polyvinyl chloride ("PVC"), and combinations thereof. Fill container can alternatively or additionally be stainless steel, such as 316 stainless steel. Drain container 160a can alternatively or additionally be stainless steel or aluminum. Containers 142 and 160 in various embodiments have wall thicknesses, which are generally uniform, and which can be from about 1 mm to about 7 mm, e.g., about 4 mm. Containers 142 and 160 define internal volumes that are sized for single exchange operation in one embodiment, e.g., can therefore be configured to hold from about one to about three liters of fresh PD dialysate or patient effluent fluid.

Reusable fill container 142 is in one embodiment made of a material that can be re-sterilized via a suitable process, such as, ultraviolet ("UV") energy, hydrogen peroxide vapor, gamma irradiation, peracetic acid, ethylene oxide, ethanol, formalin, glutaraldehyde, low energy electron beam and/or any combination of same. Although reusable drain container 160 can likewise be sterilized, it may be sufficient to merely disinfect rather than sterilize reusable drain container 160, e.g., via hot water or steam disinfection.

Reusable fill container 142 in the illustrated embodiment includes a top wall 144, a bottom wall (not visible), sidewalls 146, a front wall 148 and a back wall (not visible). For transportation, as illustrated in FIG. 6A, reusable fill container 142 is laid on its side. Reusable fill container 142 can have a generally rectangular, six-sided shape as illustrated, or have rounded sides, oblong sides and more or less than six sides or surfaces. Front wall 148 is provided with a label 151, which can be a separate label or be molded permanently into front wall. Label 151 includes information such as solution type (e.g., tradename), solution volume, and solution composition, e.g., dextrose level, glucose level, bicarbonate and/or electrolyte level.

Front wall 148 also includes a filling spout 152, which has a manual on/off valve 154 and is fitted with a cap 156a. Cap 156a can be a threaded cap, e.g., luer cap, that threads onto a threaded end of spout 152. Cap 156a is not required to seal the entire weight of the PD solution, however, because valve 154 when in the closed state prevents PD solution from flowing out of reusable fill container 142. Cap 156a does however prevent a free-flow situation if valve 154 is opened inadvertently. Cap 156a also maintains the threaded end of spout 152 in a sterilized condition.

Filling spout 152 can also be provided with a one-way check valve (not illustrated), such as a duck-billed check valve, to prevent PD solution that has left reusable fill container 142 from returning to the container. The check valve can have a small cracking pressure, such as 0.5 psig or less. Although not viewable in FIG. 6A, reusable fill container 142, e.g., at its rear or top wall or surface, can be provided with a drain port that is selectively opened to better allow any residual PD solution to be poured from the container, and/or to allow a sterilizing fluid or substance to be flushed through fill container 142. Or, as illustrated, top wall 144 can be provided with a hydrophobic vent 145. Vent 145 helps reusable fill container 142 to be filled, e.g., with a sterilizing agent or a fresh PD solution. Vent 145 also helps reusable fill container 142 to gravity feed fresh PD solution to patient 16 smoothly, while allowing and purifying air into fill container 142 to displace the gravity fed fluid.

Sidewall 146 includes or is provided with a handle 158, which can be a hinged handle that is pulled up from sidewall 146 when desired so that a user, e.g., the patient or facility professional, can lift the entire unit 140, e.g., to a room or cubicle for use. In the illustrated embodiment, reusable fill container 142 is filled with PD solution and laid on its side for mating with drain container 160. Other fill and drain container configuration combinations are possible, however, the illustrated configuration combination advantageously distributes the liquid weight evenly over the entire footprint of CAPD unit 140. Assuming reusable fill container 142 to be reasonably full of fluid when transported, fluid should not splash around too much. Handle 158 can be located alternatively on top surface 144 of reusable fill container 142 or on the top surface of drain container 160, so that CAPD unit 140 hangs more vertically when carried.

Reusable drain container 160 in the illustrated embodiment includes a top wall 162, a bottom wall (not visible), sidewalls (not visible), a front wall 164 and a back wall (not visible). For transportation as illustrated in FIG. 6A, reusable drain container 160 is likewise laid on its side. Reusable drain container 160 can have a generally rectangular, six-sided shape as illustrated, or have rounded sides, oblong sides and more or less than six sides or surfaces.

Top wall 162 includes a drain fluid inlet 168, which is fitted with a cap 170a. Cap 170a can likewise be a threaded cap, e.g., luer cap, which threads onto a threaded end of drain fluid inlet 168. Cap 170a maintains the threaded end of drain inlet 168 in a disinfected or sterilized condition. Top wall 162 and bottom wall (not visible) of drain container 160 each include (e.g., are molded with) or are provided with a mounting peg 166 that removably accepts an end of a stretchable strap 176, which the user (patient or facility professional) applies to hold CAPD unit 140 together, or removes to pull fill container 142 and drain container 160 apart. Stretchable strap 176 can be made of a stretchable nylon or bungee cord material. Strap 176 in the illustrated embodiment is thin so that it can fit easily beneath handle 158 of reusable fill container 142. Strap 176 compresses to form fit to reusable drain container 160 when fill container 142 is removed so that the strap stays connected to and does not become lost from drain container 160 for storage.

Top wall 162, like top wall 144 of reusable fill container 142, can be provided with a hydrophobic vent 167. Vent 167 helps reusable drain container 160 to be filled, e.g., with a disinfectant or sterilizing agent or with used effluent from the patient. Vent 167 helps reusable drain container 160 to be gravity fed with effluent solution smoothly, allowing air to be displaced from container 160.

Front wall 164 of reusable drain container 160 in the illustrated embodiment includes (e.g., is molded with) or is provided with four mounting pegs 174 that removably accept one corner each of a flexible CAPD set pouch 180. Pouch 180 in the illustrated embodiment includes an inner chamber that is sealed at edges 184 to form outer tabs that define the mounting holes for fitting removably over the mounting pegs 174 of reusable drain container 160. In one embodiment, one of the edges 184 is configured to be opened for treatment and then resealed after pouch 180 and its enclosed CAPD set 190 are cleaned and re-sterilized for another treatment. Resealable edge 184 can be of a tongue-and-groove type or include a zipper that closes two flaps together sealingly when zipped closed to provide a robust, sealed and selectively openable closure for pouch 180. In an embodiment, all materials for pouch 180, including any zipper or tongue-and-groove material are capable of withstanding at least one of the sterilization procedures discussed herein.

Resealable pouch 180 holds a reusable CAPD set 190 discussed in more detail below. Pouch 180 is provided with and carried by reusable drain container 160. When patient 16 proceeds with unit 140 to an area designated within facility 100 for treatment, the patient removes stretchable strap 176, so that fill container 142 can be lifted off of drain container 160. Pouch 180 is then pulled off of drain container 160 and opened to allow CAPD set 190 to be removed for use. Connecting stretchable strap 176 and resealable pouch 180 to drain container 160 enables each fill container 142 to be stored neatly and without appended structures, along with other fill containers 142, in a heated environment. The PD solution should be heated to body temperature or about 37° C. (98° F.) before delivery to the patient. It is contemplated therefore to provide one or more larger heated and insulated storage area or tank within facility 100, e.g., in backroom 150, which heat(s) and maintain(s) the fill containers 142 to and at a desired temperature. Structuring fill containers 142 to be neat or devoid of appended structures also aids in the overall heating efficiency of facility 100.

Figure 6B:
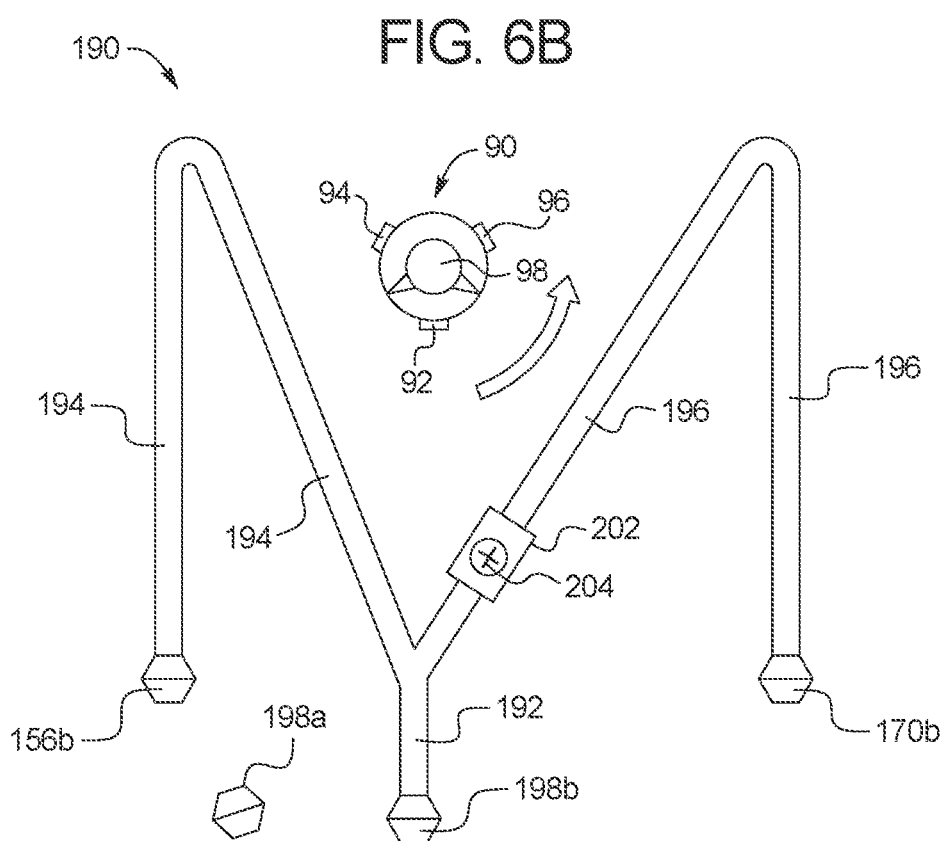
FIG. 6B is a plan view of one embodiment of a CAPD set useable with the reusable supply and drain container system of FIG. 6A.

Referring now to FIG. 6B, set 190 illustrates one embodiment for a CAPD set of the present disclosure. CAPD set 190 includes a patient line 192, a fill line 194 and a drain line 196. Patient line 192 is capped by a removable cap 198*b*, which when removed allows patient line 192 to be connected to the patient's transfer set after the patient has removed a cap 198*a* from his/her transfer set. Fill line 194 is capped by a removable cap 156*b*, which when removed allows fill line 194 to be connected to fill spout 152 of fill container 142 after the patient has removed cap 156*a* from fill spout 152. Drain line 196 is capped by a removable cap 170*b*, which when removed allows drain line 196 to be connected to drain inlet 168 of drain container 160 after the patient has removed cap 170*a* from drain inlet 168.

FIG. 6B also illustrates that drain line 196 includes a sample port 202. Sample port includes a pierceable septum 204, through which the patient can insert a syringe or needle, e.g., after being disinfected with rubbing alcohol, to draw a patient effluent sample while the patient is draining. The syringe can be held in the patient's possession or be provided by and returned to treatment facility 100.

It is contemplated to modify CAPD set 190 so that it is more easily washed, disinfected and re-sterilized between treatments. For example, it is contemplated to make one or more or all of patient line 192, fill line 194 and drain line 196 have a larger inner diameter, e.g., to be 0.375 inch (9.5 millimeter) outer diameter, so that a mechanical brush or pipe cleaner type device can be inserted into the lines and moved back and forth to remove any fibrin or other materials left after an exchange. The inner walls of one or more or all of patient line 192, fill line 194 and drain line 196 can alternatively or additionally be coated with a physiologically safe, non-friction material. Or, lines 192, 194 and 196 can be made of a low friction or slick material or version of a material to reduce the amount of trapped fibrin or other residual materials. Alternatively or additionally, the wall of one or more or all of patient line 192, fill line 194 and drain line 196 can be made thicker so that CAPD set 190 can be subjected to higher pressures during cleaning with a pressurized water or detergent. Further alternatively or additionally, one or more or all of patient line 192, fill line 194 and drain line 196 can be made of or coated with an especially chemically inert material, so that CAPD set 190 can be subjected to harsher detergents or other cleaning agents, such as ozone, or any of the sterilization agents or treatments listed above. Still further alternatively or additionally, one or more or all of patient line 192, fill line 194 and drain line 196 can be made of a high temperature resistance material, so that CAPD set 190 can be subjected to prolonged high temperature or steam disinfection. Materials and tubes sizes used for CAPD set 190 are selected so that they can be readily sanitized, e.g., disinfected and sterilized, and to remove any residual body proteins or other materials left within the set.

FIG. 6B further illustrates that CAPD set 190 also includes an extra fresh transfer set cap 198*a*. When patient 16 has completed a PD exchange using CAPD unit 140, the user places fresh transfer set cap 198*a* onto the patient's transfer set, which maintains the transfer set in a clean and protected state until it is time for the next exchange. The patient places the old transfer set cap 198*a* into pouch 180 along with the other used caps 198*b*, 156*a*/156*b* and 170*a*/170*b* and the used tubing for re-sterilization.

FIG. 6B also illustrates that as part of CAPD set 190, or used in combination with CAPD set 190, the patient can manipulate a flow control device 90 to select a desired flow path or a no-flow condition. Various embodiments for flow control device 90 are disclosed in U.S. Patent Publication No. 2009/0143723, filed Nov. 29, 2007, entitled, "Flow Control Device For Peritoneal Dialysis", the entire contents of which are hereby incorporated by reference and relied upon. For ease of illustration, flow control device 90 as illustrated includes a patient port 92, a fill port 94, a drain port 96 and a dial 98. In an embodiment, patient line 192 "Y's" or "T's" into fill line 194 and drain line 196. The "Y" or "T" tubing connector can be placed within flow control device 90, so that patient line 192 extends through patient port 92, fill line 194 extends through fill port 94, and drain line 196 extends through drain port 96.

In the example of FIG. 6B, when dial 98 is turned so that the arrows extending from dial 98 do not point towards any of the ports 92, 94 or 96, flow control device 90 is in a no-flow condition, in which all lines 192, 194 and 196 beneath the device 90 are occluded. When the patient rotates dial 98 counterclockwise (as indicated by the arrow in FIG. 6B), so that the arrows point towards patient port 92 and drain port 96, as the patient is instructed to do initially, patient line 192 and drain line 196 open, allowing the patient to drain. When the patient rotates dial 98 further counterclockwise, so that the arrows point towards fill port 94 and drain port 96, as the patient is instructed to do secondly, fill line 194 and drain line 196 open, allowing fill line 194 to prime and flush air to drain. When the patient rotates dial 98 still further counterclockwise, so that the arrows point towards patient port 92 and fill port 94, as the patient is instructed to do thirdly, patient line 192 and fill line 194 open, allowing patient 16 to be filled with fresh PD solution. When dial 98 is rotated between any of the drain, flush, or fill settings, control device 90 enters a no-flow condition, so that patient 16 can pause between the drain, flush and fill sequences.

Flow control device 90, like the syringe for sample port 102, can be the property of the patient or be provided alternatively by or returned to treatment facility 100. In the illustrated embodiment, it is assumed that flow control device 90 does not actually contact any fluid, fresh or effluent, and therefore does not need to be re-sterilized. In an alternative embodiment, in which any one or more of patient line 192, fill line 194 or drain line 196 is connected fluidly to patient port 92, fill port 94 or drain port 96 (as opposed to running through the ports), so that alternative device 90 does contact fluid, flow control device 90 is supplied via pouch 180 and placed within pouch 180 at the end of treatment for re-sterilization. To be clear, however, pouch 180 can also store, supply and transport flow control device 90 even if the flow control device does not contact fluid.

Figure 6C:
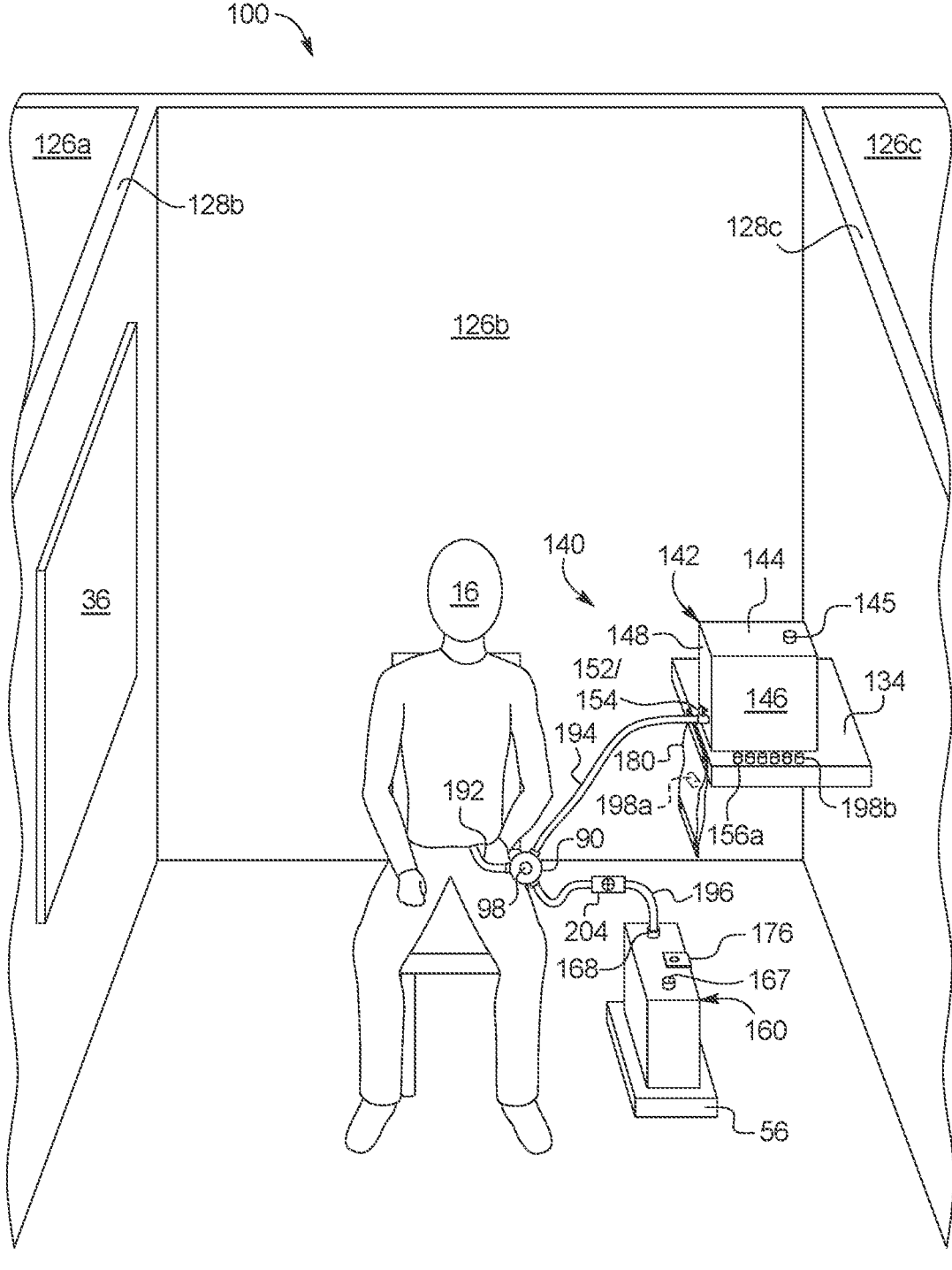
FIG. 6C is a perspective view of the system of FIG. 6A shown in use at one embodiment of a CAPD treatment area of an exchange facility of the present disclosure.

Referring now to FIG. 6C, treatment facility 100 putting CAPD unit 140 into action is illustrated. For ease of illustration, only a single patient station 126b is fully illustrated. But just like with the embodiments of FIGS. 4 and 5, it is contemplated for treatment facility 100 of FIG. 6B to have multiple patient stations 126a, 126b, 126c . . . 126n, separated by respective walls or partitions 128b, 128c . . . 128n. Patient stations 126a to 126n can have any one, or more, or all of chair, sofa, bed, or the like 34, television 36, remote control 38, desk or table 40, and/or alternating current wall outlet 42 discussed above in connection with FIG. 4. Stations 126a to 126c can likewise be closed by a curtain, wall and/or door.

FIG. 6C illustrates that patient 16 has been given a CAPD unit 140 in the form shown in FIGS. 6A and 6B and has transported the unit to a designated patient station 126b. Patient 16 has removed stretchable strap 176, allowing reusable fill container 142 to be removed from reusable drain container 160. Patient 16 has also reconnected stretchable strap 176 so that it is now connected only to reusable drain container 160. In an embodiment weigh scale 56 is provided at patient station 126b. Patient 16 first places preheated, reusable fill container 142 onto scale 56 and records (e.g., manually onto a piece of paper or entry into smart phone or tablet) or has recorded (e.g., wireless signal from weigh scale 56 to one of facility computers 106a to 106f) the weight of fresh dialysate located within reusable fill container 142. The weight of reusable fill container 142 is generally known and can be subtracted from the weight recorded by weigh scale 56 or be assumed to be canceled out by the weight of reusable drain container 160 when the full drain container is weighed at the end of the exchange, wherein a difference between the drained effluent weight and the fresh dialysate fill weight is recorded (manually or automatically as described above) as the patient's amount of ultrafiltration ("UF") removed via the exchange.

Patient 16 next lifts preheated, reusable fill container 142 from weigh scale 56 and places the fill container on a ledge, shelf, table or pedestal 134, which is set at, or has an adjustable height so as to be set at, an elevation that allows fresh, heated dialysate to flow at a proper gravity fed pressure that is safe for patient 16 (e.g., two psig). Such height can be for example about two feet (0.60 meter). Patient 16 then places reusable drain container 160 onto the weigh scale 56 next to his/her chair. It should be appreciated that weigh scale 56 is not mandatory and that without it, patient 16 could instead first place reusable drain container 160 onto the ground next to his/her chair and then place reusable fill container 142 onto ledge, shelf, table or pedestal 134. It should be appreciated that patient stations 126a to 126n and the corresponding facility 100 employing same are relatively simple structurally. Facility 100 only needs front desk 104, a fill container warmer and patient stations 126a to 126n. Patient stations 126a to 126n in turn only need the chair, weigh scale 56, ledge, shelf, table or pedestal 134, and whatever other incidentals are needed for patient comfort.

Patient 16 then connects CAPD set 190 to himself/herself, to reusable fill container 142, and to reusable drain container 160. To minimize potential contamination, patient 16 removes the caps from a line and then connects that line as soon as possible to its destination. For example, patient 16 can first remove cap 170a from drain fluid inlet 168 and cap 170b from drain line 196, and then immediately connect drain line 196 to drain fluid inlet 168. Next, patient 16 can remove cap 156a from filling spout 152 and cap 156b from fill line 194, and then immediately connect fill line 194 to filling spout 152. Then, patient 16 can remove transfer set cap 198a from his/her transfer set and cap 198b from patient line 192, and then immediately connect patient line 192 to the patient's transfer set (not illustrated). Fill line 194 and drain line 196 and possibly even patient line 192 are occluded during the above connections via manual clamps, e.g., Halkey Roberts™ clamps, via flow control device 90, or possibly using both manual clamps and flow control device 90.

In the illustrated example, the six removed caps 156a, 156b, 170a, 170b, 198a and 198b are placed onto ledge, shelf, table or pedestal 134 for safekeeping. In FIG. 6C, pouch 180 is shown holding an extra sterilized transfer set cap 198a, which patient 16 will remove from pouch at the end of the PD exchange to cap off the patient's transfer set. Sterilized transfer set cap 198a can be fitted with a small enclosed antiseptic pocket prior to sterilization. The pocket is broken, spreading antiseptic over the tip of the patient's transfer set when patient 16 places cap 198a onto the patient's transfer set at the end of an exchange. The antiseptic helps to maintain the patient's transfer set in a sterilized state between exchanges. One suitable cap having integral disinfectant is set forth in U.S. Pat. No. 7,198,611, entitled, "Dialysis Connector And Cap Having An Integral Disinfectant", assigned to the assignee of the present disclosure, the entire con tents of which are incorporated herein by reference and relied upon.

Patient 16 then either manipulates manual clamps, e.g., Halkey Roberts™ clamps or flow control device 90 to perform the exchange. Again, manual clamps (not illustrated) and/or flow control device 90 can be the property of patient 16 or alternatively be loaned to the patient by facility 100. If the components are the property of facility 100, patient 16 can return manual clamps (not illustrated) and/or flow control device 90 to front desk 104 at the end of treatment, e.g., by placing same into pouch 180 for refurbishing if needed and repacking.

Regardless of whether patient 16 uses manual clamps (not illustrated) and/or flow control device 90 with CAPD set 190, the drain, flush and fill routine is as described above. Patient 16 first removes clamps and/or sets flow control device 90 so that fill line 194 is closed, while patient line 192 and drain line 196 are opened to allow patient 16 to drain effluent to reusable drain container 160. The drain fluid pushes air out of container 160, through hydrophobic filtered vent 167, so that container 160 does not push air elsewhere within from CAPD set 190, and so that drain fluid flow is smooth.

In an embodiment, patient 16 sets the "Y" or "T" tubing connector of CAPD set 190 so as to be roughly in a horizontal plane and/or monitors the amount of drain fluid that has entered reusable drain container 160 (e.g., by watching how full the container is or by watching weigh scale 56) and/or knows intuitively when drain is about to end, so that the patient can end the drain phase of the exchange with effluent (but still sterile) fluid remaining within patient line 192, preventing air from entering same. To this end, it is typical for PD patients to drain the majority (e.g., eighty percent) of the effluent quickly and then hit an efficient flow wall, where the effluent flowrate drops significantly. During the low flow drain period, patient 16 can move around or stand up to reposition his or her indwelling catheter in an attempt to drain the last percentage (e.g., twenty percent) of effluent. It is during this time that patient 16 can be cognizant of patient line 192 so as to end the drain phase with patient line 192 full. But even if patient line 192 becomes partially or fully filled with air, (i) patient line 192 is small so that there is only a small amount of air and (ii) the air either comes from the patient himself/herself or from disinfected or sterilized reusable drain container 160, so that the air should not carry contamination. At the end of drain, patient 16 removes drain line 196 from container 160 and places drain cap 170a back onto drain fluid inlet 168, so that a now full drain container 160 can be tipped and transported.

At the end of the drain phase, or when patient 16 is not initially full with fluid, patient 16 sets manual clamps and/or sets flow control device 90 so that patient line 192 is closed, while fill line 194 and drain line 196 are opened to allow patient 16 to prime and flush fill line 194, pushing air from line 194 to reusable fill or drain container 142, 160. Patient 16 watches fill line 194 fill with fluid. When fill line 194 is completely full, patient 16 ends the fill line flush using manual clamps and/or flow control device 90. The fresh fluid level drop within reusable fill container 142 pulls and purifies air through hydrophobic filtered vent 145, so that container 142 does not seek displacement air elsewhere from within from CAPD set 190, and so that fluid flow during flush is smooth.

At the end of the prime and flushing phases, patient 16 sets manual clamps and/or sets flow control device 90 so that patient line 192 and fill line 194 are opened, while drain line 196 is closed to allow patient 16 to gravity fill (at the desired head height pressure) with fresh fluid from container 142. The fresh fluid level drop within reusable fill container 142 again pulls and purifies air through hydrophobic filtered vent 145, so that container 142 does not seek displacement air elsewhere from within from CAPD set 190, and so that fresh PD filling fluid flow to patient 16 is smooth.

Once the patient fill and thus the PD exchange has been completed, patient 16 can pack-up and proceed with his/her day or evening. It is contemplated however that patient 16 could remain within facility 100 for a predetermined dwell time and repeat the above procedure one or more times, in which case patient 16 is given multiple CAPD units 140 for use at patient station 126b. Patient stations 126a to 126n can be provided with warmers or insulated boxes (not illustrated) for storing one or more preheated reusable fill container 142. Or, patient 16 can return to front desk 104 each time, dropping off the old CAPD unit 140 and receiving a new CAPD unit for the second, third, etc. exchange. In such case, warmers or insulated boxes are not needed at patient stations 126a to 126n.

Before patient 16 returns to front desk 104, the patient removes sterile cap 198a from pouch 180, disconnects patient line 192 from his/her transfer set and places, e.g., threads, new sterile cap 198a onto the transfer set. Again, sterile cap 198a can be loaded with disinfectant to kill any bugs that may appear due to the time that cap 198a resides within pouch 180 or from the removal of patient line 192 from the transfer set.

Patient 16 then collects CAPD set 190, the remaining five caps (drain cap 170a has been placed back onto drain fluid inlet 168) from ledge, shelf, table or pedestal 134 and possibly flow control device 90 and/or manual clamps, and places same into pouch 180. The patient disconnects strap 176 from one of the mounting pegs 166 of drain container 160, places fill container 142 onto drain container 160, and reconnects strap 176 to the peg 166 of the drain container. Patient 16 presses pouch 180 onto mounting pegs 174 to reconstruct a used CAPD set 190 in the form illustrated in FIG. 6A. Patient 16 then uses handle 158 of fill container 142 to return used CAPD set 190 to front desk 104. It is contemplated to have patient 16 pay a deposit upon receiving fresh CAPD set 190, and for facility 100 to return the deposit to patient 16 only if pouch 180 is returned with all necessary reusable items, e.g., all caps, used CAPD set 190, possibly flow control device 90, and/or manual clamps.

It should be appreciated that the above exchange produces no waste, eliminating disposable cost. The cost of the "reusables" is the cost of transporting CAPD sets 190 and fluid containers to and from the place of refurbishment, the refurbishment itself, and the subsequent storage and heating at treatment facility 100.

Figure 6D:
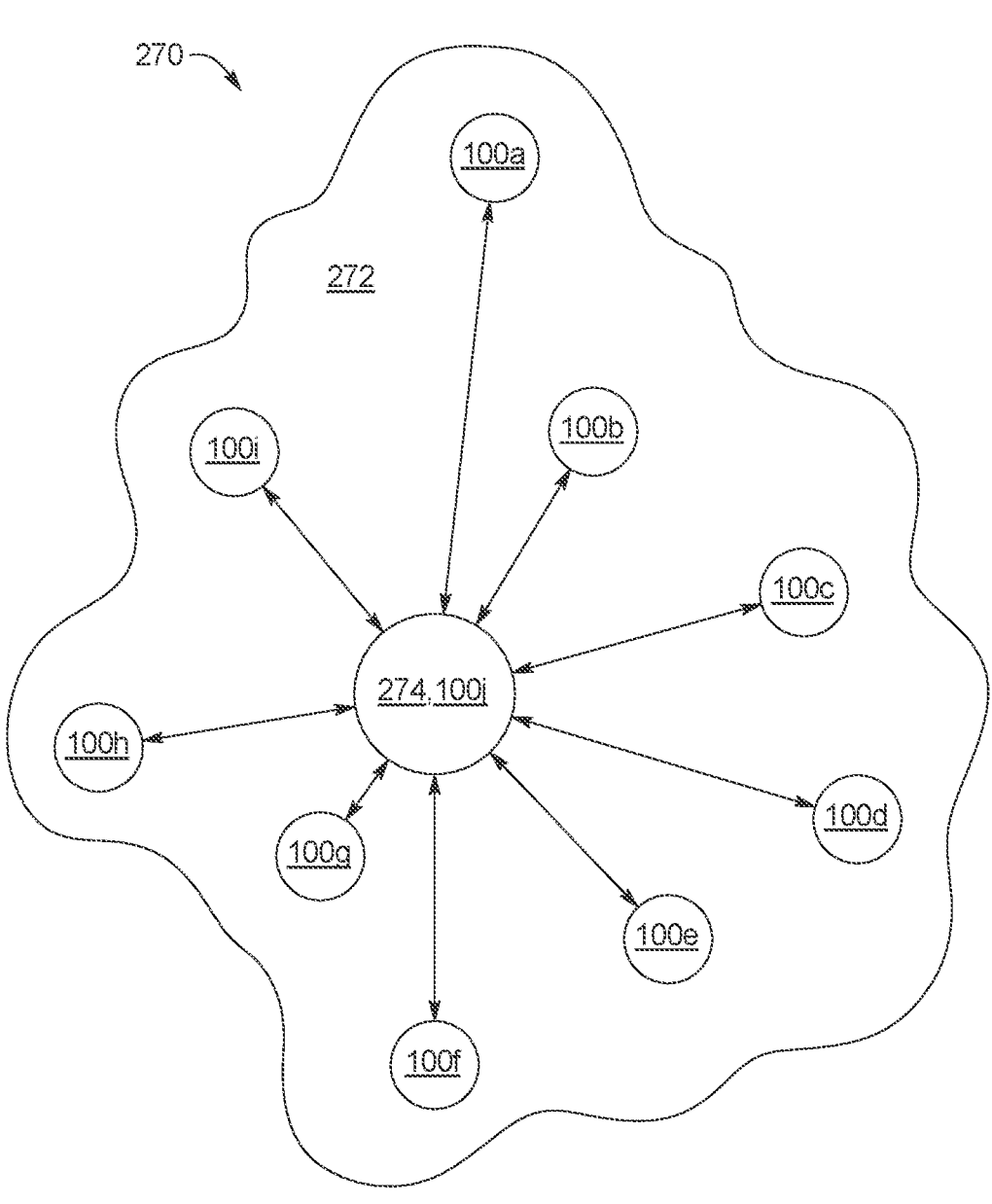
FIG. 6D is a schematic view illustrating one embodiment for cleaning and refurbishing the reusable supply and drain container system and the CAPD set of FIGS. 6A and 6B using a hub and spoke facility arrangement.

Referring now to FIG. 6D, one operational flow system 270 for the CAPD units 140 of FIGS. 6A to 6C is illustrated. System 270 is implemented for a geographical area 272, which can for example be a densely populated city in a country currently having little or no dialysis or kidney failure treatment reimbursement. Example system 270 includes nine satellite treatment facilities 100a to 100i. System 270 includes a central refurbishing center 274, which can also serve as a tenth treatment facility 100j. The double arrows indicate two-way shipping between treatment facilities 100a to 100i and refurbishing center 274/facility 100j.

In one embodiment, used CAPD units 140 brought by patient 16 to front desk 104 are drained and then shipped as-is to refurbishing center 274/facility 100j for re-sterilization, disinfection and refilling. Refurbishing center 274/facility 100j includes the equipment and chemicals needed (if necessary) to mechanically, chemically and/or heat sterilize reusable fill container 142, CAPD set 190, caps 156a, 156b, 170a, 170b, 198a and 198b, and possibly reusable drain container 160. Transfer set cap 198a is fitted with a new disinfectant pouch in one embodiment. In an alternative embodiment, reusable drain container 160 is disinfected, e.g., with hot water or steam, but is not subjected to a sterilizing process.

In a further alternative embodiment, reusable drain container 160 is so disinfected, but is disinfected at its satellite treatment facility 100a to 100i. Here, shipping costs are reduced but each satellite treatment facility 100a to 100i is then required to have a disinfecting, e.g., hot water bath or steam cleaning system. Also, if pouch 180 with the used caps and CAPD sets 190 is to remain with reusable drain container 160, then each satellite treatment facility 100a to 100i will need to have a way to sterilize CAPD set 190, caps 156a, 156b, 170a, 170b, 198a and 198b, and to reload transfer set cap 198a with a disinfecting pocket. In such a case, it is contemplated that each patient 16 purchase a number of CAPD sets 190, which are coded, e.g., barcoded, numbered, or otherwise specified for use only with that patient. This may provide an advantage however in that it may be permissible to leave a biofilm on the insides of CAPD sets 190 because the biofilm would be the patient's own film. Thus, used CAPD sets 190 and caps may only need mechanical cleaning and then hot water or steam disinfection before being placed in a pouch, which is then subjected to a sterilization process, e.g., UV radiation, to sterilize the insides of the pouches and the outsides of CAPD sets 190. When patient 16 enters treatment facility 100, the patient here receives one of his/her own sets. Having two or more sets enables patient 16 to come to facility 100 every day and receive a refurbished set, while the second or third set is being refurbished for the next day's exchange.

In still another alternative embodiment, if it is determined that it is too difficult to clean CAPD sets 190, then the sets and likely the caps can be discarded after each use. Flow control device 90 and/or manual clamps can be reused. It is contemplated here to make the disposable clean CAPD sets 190 as cost effective as possible to make the PD exchanges as affordable as possible for the patient.

Figure 7A:
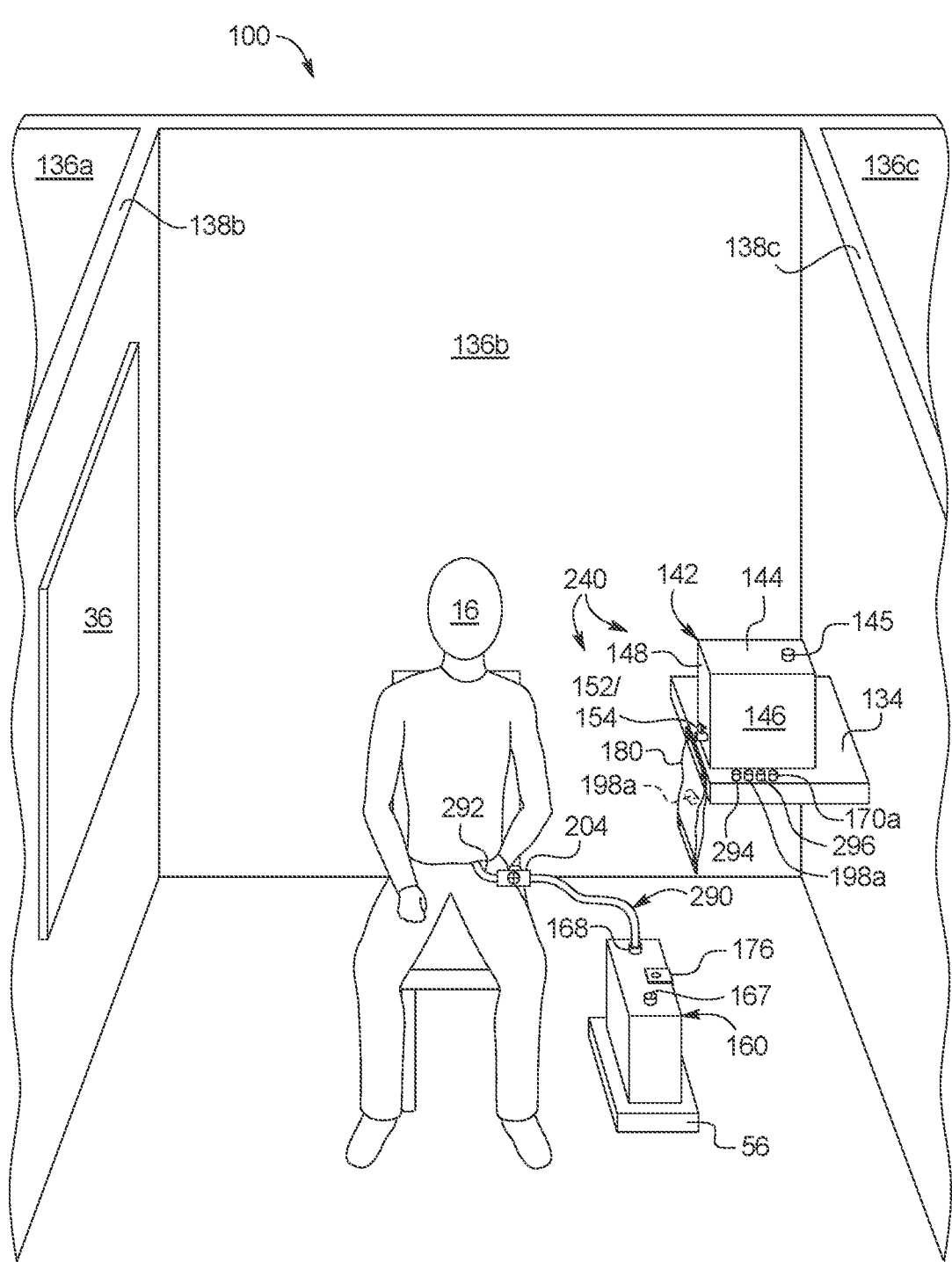
FIG. 7A is a perspective view of one embodiment of a CAPD treatment area of an exchange facility of the present disclosure undergoing a patient drain procedure using the reusable supply and drain container system of FIG. 6A with an alternative two-way CAPD set.
Figure 7B:
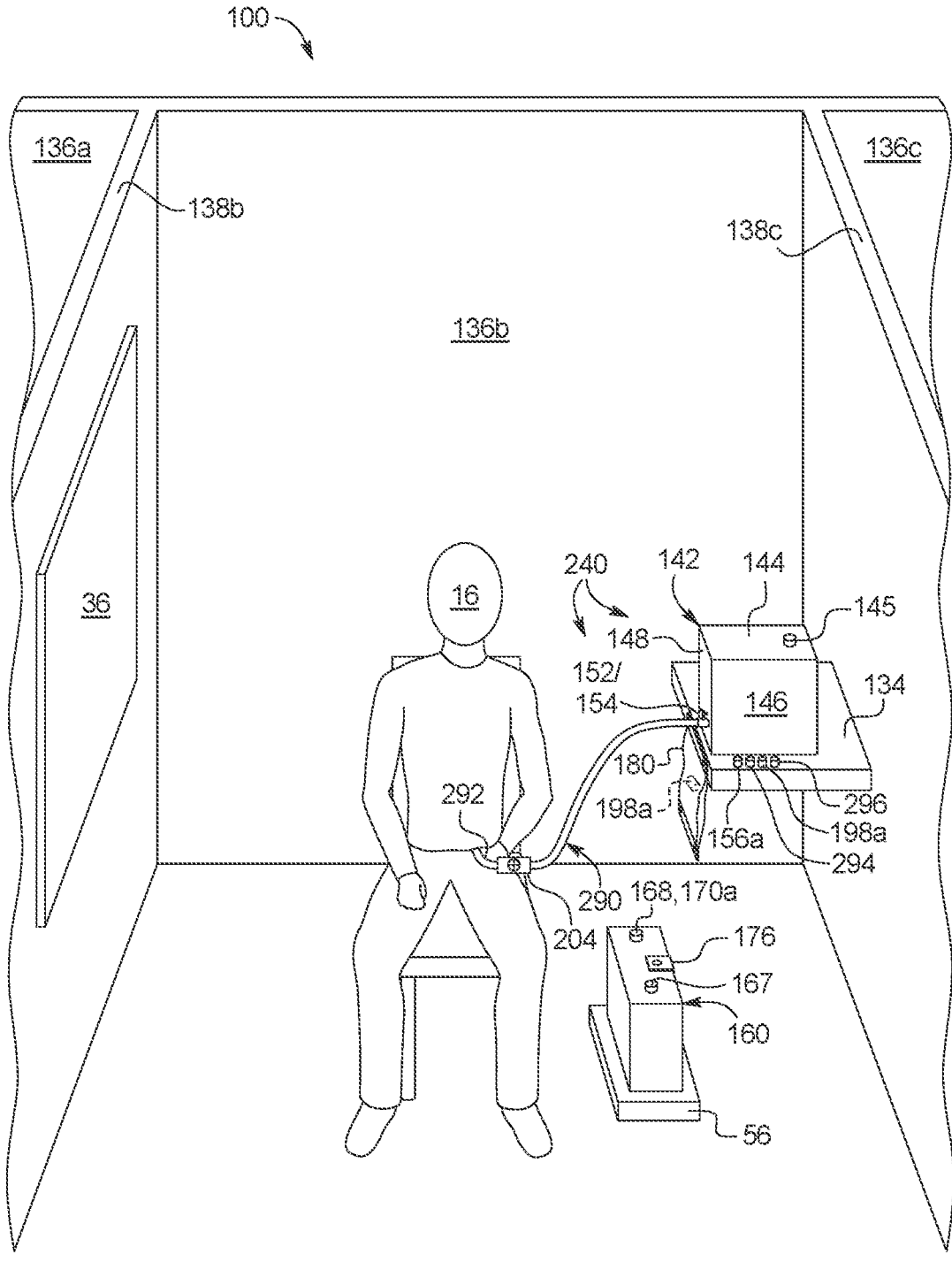
FIG. 7B is a perspective view of one embodiment of a CAPD treatment area of an exchange facility of the present disclosure undergoing a patient fill procedure using the reusable supply and drain container system of FIG. 6A with an alternative two-way CAPD set.

Referring now to FIGS. 7A and 7B, an alternative treatment facility 100 using an alternative CAPD unit 240 is illustrated. Again for ease of illustration, only a single patient station 136b is fully illustrated. But just like with the embodiments of FIGS. 4 and 5, it is contemplated for treatment facility 100 of FIGS. 7A and 7B to have multiple patient stations 136a, 136b, 136c . . . 136n, separated by respective walls or partitions 138b, 138c . . . 138n. Patient stations 136a to 136c can have any one, or more, or all of chair, sofa, bed, or the like 34, television 36, remote control 38, desk or table 40, and/or alternating current wall outlet 42 discussed above in connection with FIG. 4. Stations 136a to 136c can likewise be closed by a curtain, wall and/or door.

CAPD unit 240 includes reusable fill container 142 and reusable drain container 160 as they have been described above, including all associated structure and alternatives. The primary difference between alternative CAPD unit 240 and CAPD unit 140 discussed above is that CAPD set 140 has been replaced with a simplified CAPD set 290. Simplified CAPD set 290 includes a single line or tube 292 capped at each end by a patient cap 294 and a drain/fill container cap 296. Line or tube 292 can be made of any of the materials and have any of the diameters, lengths and wall thicknesses discussed above for CAPD set 190. As illustrated in FIGS. 7A and 7B, line or tube 292 is long enough to reach both reusable fill container 142 and reusable drain container 160.

CAPD set 290, like CAPD set 190, also includes a pierceable septum 204, through which the patient can insert a syringe or needle, e.g., after being disinfected with rubbing alcohol, to draw a patient effluent sample while the patient is draining. Again, the syringe can be owned by the patient or be provided by and returned to treatment facility 100.

FIG. 7A illustrates that patient 16 has been given a CAPD unit 240 and has transported the unit to a designated patient station 136b. Patient 16 has removed stretchable strap 176, allowing reusable fill container 142 to be removed from reusable drain container 160. Patient 16 has also reconnected stretchable strap 176 so that it is now connected only to reusable drain container 160. Patient 16 then places preheated, reusable fill container 142 onto scale 56 and records (e.g., manually on a piece of paper or via entry into smart phone or tablet) or has recorded (e.g., via a wireless signal from weigh scale 56 to one of facility computers 106a to 106) the weight of fluid within reusable fill container 142.

Patient 16 next lifts preheated, reusable fill container 142 from weigh scale 56 and places the fill container on a ledge, shelf, table or pedestal 134, which is set at, or has an adjustable height so as to be set at, an elevation that allows fresh, heated dialysate to flow at a gravity fed pressure that is safe for patient 16. Patient 16 then places reusable drain container 160 onto the weigh scale 56 next to his/her chair. Again, weigh scale 56 is not mandatory and that without it, patient 16 can instead first place reusable drain container 160 onto the ground next to his/her chair and then place reusable fill container 142 onto ledge, shelf, table or pedestal 134.

FIG. 7A illustrates a drain procedure using CAPD unit 240. Here, with both ends of line or tube 292 clamped via mechanical clamps (no need for flow control device 90 here), patient 16 removes cap 170a from drain fluid inlet 168 and drain/fill container cap 296 from the distal end of line or tube 292 and sets caps 170a and 296 onto ledge, shelf, table or pedestal 134. The patient then connects the distal end of line or tube 292 to drain fluid inlet 168 of drain container 160. Patient 16 then removes patient cap 198a from the patient's transfer set and patient cap 294 from the proximal end of line or tube 292 and sets caps 198a and 294 onto ledge, shelf, table or pedestal 134. The patient then connects the proximal end of line or tube 292 to the patient's transfer set. The patient is now set to drain.

To drain as illustrated in FIG. 7A, patient 16 removes the manual, e.g., Halkey Roberts™, clamps from line or tube 292, allowing effluent fluid to gravity flow from the patient's peritoneum to drain container 160. Hydrophobic cap 167 of drain container 160 allows air to vent while effluent fluid fills the container, enabling the effluent fluid to flow smoothly from the patient's peritoneum to the drain container. Again, patient 16 will drain quickly at first and then hit a low flowrate stage. At the low flowrate stage, patient 16 can stand up or maneuver himself/herself to help drain the last portion of the patient's effluent from the patient's peritoneum. Patient 16 can draw a drain sample from pierceable septum 204 at any time during drain. When patient 16 is near the end of the drain phase (as determined by the patient using weigh scale 56, level of drain fluid within container 160, or through acquired knowledge), the patient clamps the distal end of line or tube 292 and removes the distal end of the line from drain fluid inlet 168 of drain container 160, attempting to leave fluid in tube 292, so that the line remains primed. Patient 16 then places drain cap 170a back onto drain fluid inlet 168, so that a now full drain container 160 can be tipped and transported.

To fill with fresh fluid as illustrated in FIG. 7B, patient 16 removes cap 156a from fill container filling spout 152, and sets cap 156a onto ledge, shelf, table or pedestal 134. Patient 16 moves the distal end of line or tube 292 from fluid inlet 168 of drain container 160 to filling spout 152 of reusable fill container 142 and connects the distal end to the filling spout 152. Patient 16 then removes the manual clamp from the distal end of line or tube 292 and opens manual on/off valve 154 of reusable fill container 142. If for some reason line 292 is not primed or not fully primed, patient 16 can close a clamp at the proximal end of line or tube 292, e.g., between the patient and pierceable septum 204. Fresh fluid from fill container should gravity feed line or tube 292, pushing the air up the line, into fill container 142 and out hydrophobic vent 145 of the container. If needed, a hydrophobic vent (not illustrated) can be incorporated into pierceable septum 204 of reusable line or tube 292, so that fresh fluid from fill container 142 gravity feeding line or tube 292, can push air out of the hydrophobic vent (not illustrated) in a sterile manner. The hydrophobic vent may obviate the need to leave line 292 primed after the drain phase. When priming is completed, the manual clamp at the proximal end of line or tube 292 can be removed.

Fresh fluid from fill container 142 then fills the patient's peritoneum. When the fresh fluid fill is completed, the patient packs CAPD unit 240 up in a similar manner discussed above for CAPD unit 140. In particular, before patient 16 returns to front desk 104, the patient removes a new sterile cap 198a from pouch 180, disconnects line or tube 292 from his/her transfer set and places, e.g., threads, new sterile cap 198a onto the transfer set. As before, sterile cap 198a can be loaded with disinfectant to kill any bugs that may appear due to the time that cap 198a resides within pouch or from the removal of patient line 292 from the transfer set. Patient 16 then collects the remaining three caps 198a, 294 and 296 (drain cap 170a has been placed back onto drain fluid inlet 168) from ledge, shelf, table or pedestal 134 and possibly manual clamps, and places same into pouch 180. The patient disconnects strap 176 from one of the mounting pegs 166 of drain container 160, places fill container 142 onto drain container 160, and reconnects strap 176 to the peg 166 of the drain container. Patient 16 then presses pouch 180 onto mounting pegs 174 to reconstruct a used CAPD unit 240 in a form illustrated in FIG. 6A. Patient 16 then uses handle 158 of fill container 142 to return the used CAPD unit 240 to front desk 104. It is again contemplated to have patient 16 pay a deposit upon receiving the fresh CAPD set 240, and for facility 100 to return the deposit to patient 16 only if pouch 180 is returned with all necessary reusable items, e.g., all caps, used CAPD unit 240, and possibly manual clamps.

It should be appreciated that the above exchange likewise produces little or no waste, greatly reducing or eliminating disposable cost. The cost of the "reusables" is the cost of transporting CAPD sets 290 and the containers to and from the place of refurbishment, the refurbishment itself, and the subsequent storage and heating at treatment facility 100.

The operational flow system 270 of FIG. 6D is equally applicable to CAPD sets 290 and units 240 of FIGS. 7A and 7B. In one embodiment, used CAPD sets 290 and units 240 brought by patient 16 to front desk 104 are drained and then shipped as-is to refurbishing center 274/facility 100j for re-sterilization, disinfection and refilling. Refurbishing center 274/facility 100j includes the equipment and chemicals needed (if necessary) to mechanically, chemically and/or heat sterilize reusable fill container 142, CAPD set 190, caps 170a, 198a, 292 and 294, and possibly reusable drain container 160. Transfer set cap 198a is fitted with a new disinfectant pouch in one embodiment. In an alternative embodiment, reusable drain container 160 is disinfected, e.g., with hot water or steam, but is not subjected to a sterilizing process.

Like before, reusable drain container 160 can be disinfected at its satellite treatment facility 100a to 100i. Here, shipping costs are reduced but each satellite treatment facility 100a to 100i is then required to have a disinfecting, e.g., hot water bath or steam cleaning system. Also, if pouch 180 with the used caps and CAPD sets 290 is to remain with reusable drain container 160, then each satellite treatment facility 100a to 100i will need to have a way to sterilize CAPD set 290 and caps 170a, 198a, 294 and 296, and to reload transfer set cap 198a with a disinfecting pocket. In such a case, it is contemplated that each patient 16 purchase a number of CAPD sets 290, which are coded, e.g., bar-coded, numbered, or otherwise specified for use only with that patient. This may provide the advantages discussed above for CAPD set 190.

In still another alternative embodiment, if it is determined that it is too difficult to clean CAPD sets 290, then the sets and likely the caps can be discarded after each use. It is contemplated here to make clean CAPD sets 290 as cost effective as possible to make the PD exchanges as affordable as possible for the patient. It should be appreciated however that straight line CAPD sets 290 should be easier to clean, disinfect and sterilize than CAPD sets 190 discussed above.

Referring now to FIGS. 8A to 8G, an alternative treatment facility 100 using an alternative filling system is illustrated. Again for ease of illustration, only a single patient station 186b is fully illustrated. But just like with the embodiments of FIGS. 4 and 5, it is contemplated for treatment facility 100 of FIGS. 8A to 8F to have multiple patient stations 186a, 186b, 186c . . . 186n, separated by respective walls or partitions 188b, 188c . . . 188n. Patient stations 186a to 186n can have any one, or more, or all of chair, sofa, bed, or the like 34, television 36, remote control 38, desk or table 40, and/or alternating current wall outlet 42 discussed above in connection with FIG. 4. Stations 136a to 136n can likewise be closed by a curtain, wall and/or door.

The system of FIGS. 8A to 8G can use either CAPD set 190 or 290 discussed above (illustrated here using set 190). CAPD set 190 or 290 can again be provided in CAPD set pouch 180. It is contemplated to eliminate the caps used with CAPD set 190 or 290 and instead have pouch 180 provide only a new patient transfer set cap 198a, which can be fitted with a disinfecting breakable pouch as has been described above. In a further alternative embodiment, pouch 180 is also eliminated and new transfer set cap 198a is placed instead onto the end of patient tube 192. If cap 198a is provided with disinfectant, cap 198a can be threaded loosely onto patient tube 80 so that the disinfectant is not disbursed.

Also, CAPD set 190 or 290 is in one embodiment not fully sterilized when given to patient 16. Instead, in between treatments, CAPD set 190 or 290 is hot water disinfected to mechanically flush any residual fibrin or particulates from the sets, so that the sets are free of any patient matter. The hot water also partially sterilizes CAPD set 190 or 290. If desired, a mild sterilizing agent can be added to the hot water disinfection, e.g., an organic solvent. If so, hot water is used at the end of the disinfecting process to flush the mild sterilizing agent from CAPD set 190 or 290.

Figure 8A:
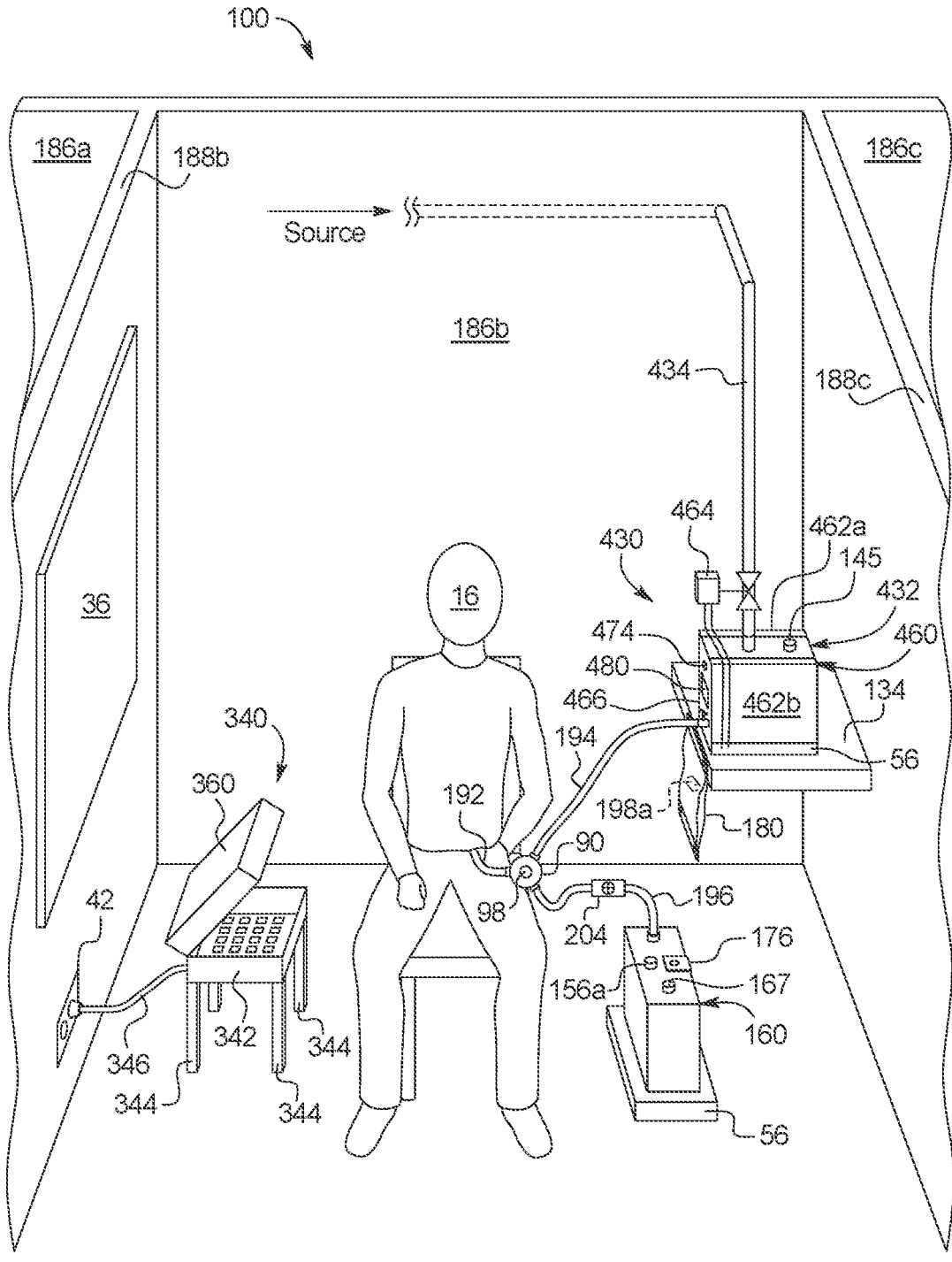
FIG. 8A is a perspective view of a CAPD treatment area of an exchange facility of the present disclosure using one embodiment of a permanent or semi-permanent filling system.

The final sterilization of CAPD set 190 or 290 takes places at patient station 186b using sterilizing unit 340 in various embodiments. In FIGS. 8A and 8F, sterilizing unit 340 includes a base 342 and a lid 360 hingedly connected to base 342. Base 342 and lid 360 can be configured to set on a table or ledge (FIG. 8F), such as ledge 134. In the embodiment illustrated in FIG. 8A, base 342 is alternatively provided with its own set of legs 344 to prop base 342 and lid 360 up from the ground. The inner surfaces of base 342 and lid 360 are in one embodiment made of or coated with a ultraviolet ("UV") light-reflective material for reasons discussed below. Patient 16 places CAPD set 190 or 290 and transfer set cap 198a into the clamshell between base 342 and lid 360 and closes the clamshell. Sterilizing unit 340 then energizes the upper and lower arrays of UV lights or UV-LED's for a time sufficient to bring disinfected CAPD set 190 or 290 and transfer set cap 198a to a properly sterilized condition.

A power cord 346 runs from base 342 or lid 360 to power outlet 42. Power outlet 42 powers a plurality of UV lights 348, such as UV light-emitting diodes (UV-LED's) provided in both base 342 and lid 360. The UV lights 348 can alternatively be UV lamps. The UV lights 348 are connected in series or parallel via one or more wire or printed circuit board trace 350 (FIG. 8F). It is contemplated in one embodiment for the inner surfaces of base 342 and lid 360 to be ceramic or FR-4 printed circuit boards upon which one or more copper trace 350 is formed. The UV lights 348 are surface mounted to the trace wires 350, e.g., either in series or parallel as desired. Alternatively, wires 350 form a mesh to which the UV lights 348 are hard-wired, soldered or are otherwise connected electrically. Still further alternatively, UV lights 348 are UV bulbs that thread or plug into sockets provided by the inside surfaces of base 342 and lid 360. The UV bulbs can likewise be wired together in a series or parallel relationship.

Power cord 346 plugs into a socket 352 located in base 342 in the illustrated embodiment. Power runs from socket 352 to a manual on/off switch 354. It is contemplated to place switch in series electrical combination with a second, mechanical switch (not illustrated) that is closed when lid 360 is closed onto base 342. In this manner, lid 360 must be closed before switch 354 is turned on for UV lights 348 to receive power, preventing UV light energy from being emitted when unit 340 is open, which could harm or disturb an outside entity. Switch 354 can be located along any surface of sterilizing unit 340 for convenient reach and activation. In the illustrated embodiment, switch 354 is in electrical communication with electronics 356. Electronics 356 can include one or more electrical component and perform one or more function, such as, conditioning and/or regulating incoming AC power into a desired voltage and/or type (e.g., DC).

Electronics 356 can also include a timer that is preset to allow UV lights 348 to be powered for a prescribed amount of sterilization time after patient 16 places CAPD set 190 or 290 and transfer set cap 198a onto base 342, closes lid 360, and presses switch 354 (e.g., a momentary, self-resetting switch). When the prescribed amount of time has elapsed according to the timer, power to UV lights 348 is removed automatically and a ready light and/or sound maker (not illustrated) is/are activated. Patient 16 can then remove CAPD set 190 or 290 from sterilizing unit 340 for use. Transfer set cap 198a can remain inside sterilizing unit 340 until the PD exchange is completed and patient 16 needs a clean transfer set cap. The total disinfecting power from the cumulative light emitted by each of the UV lights 348 of base 342 and lid 360 is enough by an engineering factor to sterilize CAPD set 190 or 290 within a reasonable period of time, e.g., two to ten minutes.

One advantage of performing the final sterilization of CAPD set 190 or 290 at patient station 186b is that the patient immediately thereafter connects CAPD set 190 or 290 to the drain and/or fill containers, so that CAPD set 190 or 290 does not have to be capped. Also, CAPD set pouch 180 may be eliminated altogether. Further still, new transfer set cap 198a can be eliminated in an embodiment in which patient 16 sterilized the existing cap 198a using unit 340, e.g., while the patient is draining and filling. Patient 16 at the end of the exchange here replaces his/her own resterilized transfer set cap 198a onto his/her transfer set and takes used CAPD set 190 or 290 only up to front desk 104 for deposit redemption. Treatment facility 100 later that day or that night collects all of the used and returned CAPD sets 190 and/or 290 and possibly caps 198a, places them in a hot water sterilizing bath or unit, the bath or unit circulates and flushes hot water through the insides of CAPD sets 190 and/or 290, and filters the circulated water to capture particulate and debris removed from the insides of CAPD sets 190 and/or 290, removing such particulate and debris from the hot water loop. The disinfected CAPD sets 190 and/or 290 are then dried and stored for use later the same day or the next day.

It is expressly contemplated that sterilizing unit 340, and the use thereof to eliminate CAPD pouch 180, in combination with the hot water disinfection just described, can be used with any of the treatment facility embodiments described herein including those of FIGS. 6A to 6D and FIGS. 7A and 7B. Regarding FIG. 6D, it is noted that the elimination of CAPD set pouch 180 and the caps associated with CAPD sets 190 and 290, as well as the in-facility 100 re-sterilization of the CAPD sets, reduces largely the amount of, and possible eliminates components needing to be delivered to and from refurbishing center 274/treatment facility 100j.

Reusable drain container 160 including all of its associated structure and alternatives can be used again with treatment facility 100 of FIGS. 8A to 8G. Cap 156a is again provided with drain container 160 and is removed as illustrated in FIG. 8A for connection to CAPD set 190 or 290. It is contemplated to flush reusable drain container 160 with hot water at treatment facility 100, as discussed above for CAPD sets 190 and 290, and to reuse caps 156a, further eliminating the components that have to be delivered to and from refurbishing center 274/treatment facility 100j. Because container 160 is a drain container, it does not need to be completely re-sterilized. It is contemplated however to disinfect drain container 160 between uses, e.g., via hot water disinfection or a mild detergent, such as bleach.

Figure 8B:
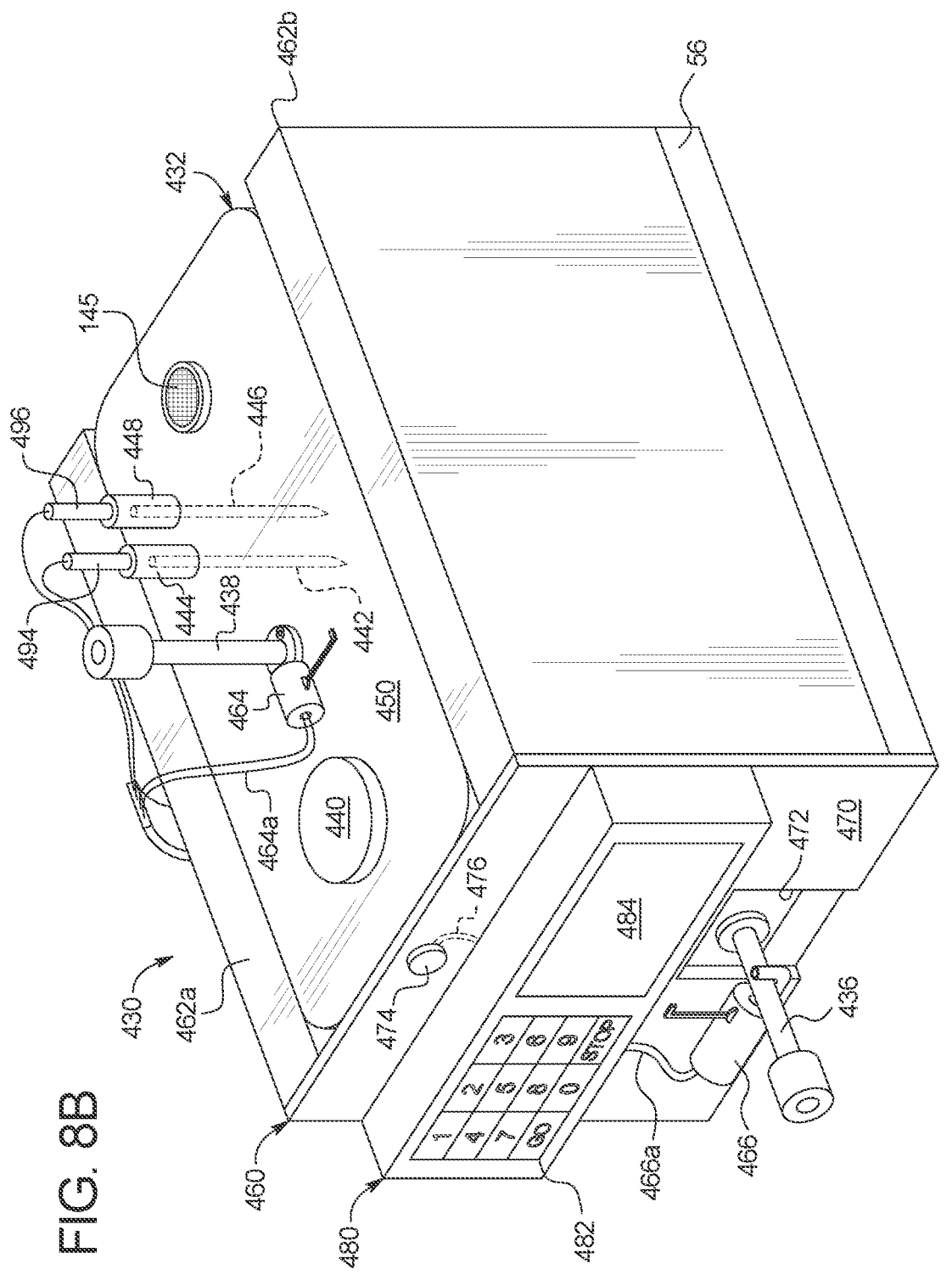
FIG. 8B is a perspective view of one embodiment of a permanent or semi-permanent filling system useable in the system of FIG. 8A.

FIGS. 8A and 8B illustrate that reusable fill container 142 discussed above has been replaced with a permanent or semi-permanent filling system 430. In general, filling system includes a fill container 432 that is removably coupled to an energizing unit 460. Energizing unit 460 remains in place, e.g., can be bolted to, ledge, shelf, table or pedestal 134 and is not transported back and forth by patient 16. FIG. 8A illustrates that energizing unit 460 operates with a weigh scale 56 in one embodiment, which can be separate from or made part of unit 460. Energizing unit 460 includes a pair of sterilizing panels 462a/462b, a control unit 480, a ready light 474, an electrically actuated fill valve 464, and an electrically actuated dispense valve 466, among other items.

Figure 8C:
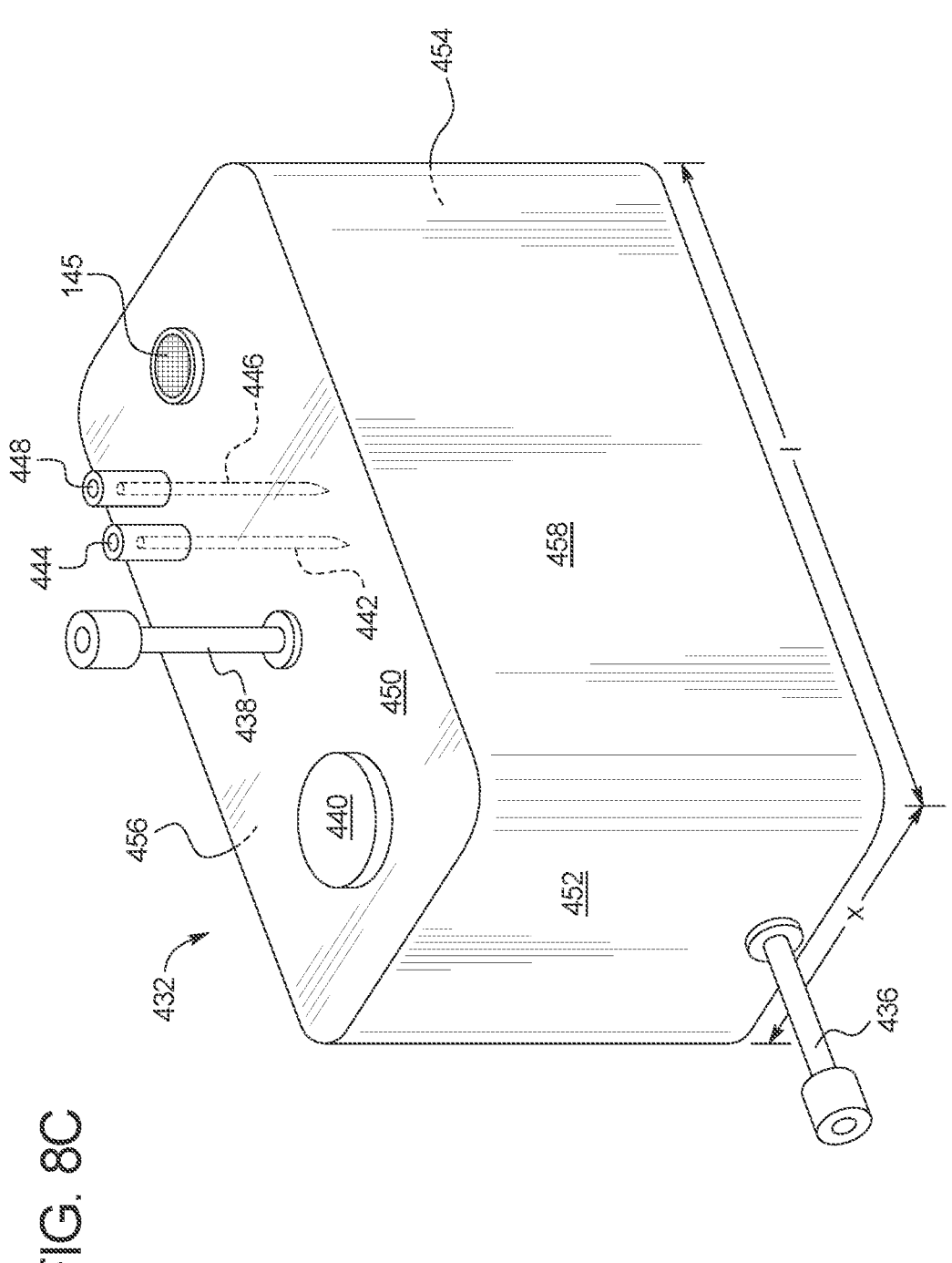
FIG. 8C is a perspective view of one embodiment of a fill container useable with the permanent or semi-permanent filling system of FIGS. 8A and 8B.

It is contemplated that fill container 432 remain at least semi-permanently coupled to energizing unit 460, e.g., over multiple treatments for multiple patients, over multiple days or even multiple weeks. Fill container 432 can be removed however for intermittent cleaning, repair or replacement. FIGS. 8A and 8C illustrate that fill container 432 can include a hydrophobic vent 145, just as with reusable fill container 142. Semi-permanent fill container 432 in FIGS. 8A and 8C receives fresh, but not necessarily sterile, water or peritoneal dialysis solution via a fill line 434 and electrically actuated fill valve 464 of energizing unit 460. Scale 56 of energizing unit 460 operates with control unit 480 and electrically actuated fill valve 464 to weigh the fresh fluid as it enters semi-permanent fill container 432. When the actual weight of the fresh fluid reaches the patient's prescribed fill weight, control unit 480 causes fill valve 464 to close, leaving a prescribed amount of fresh fluid within fill container 432. When control unit 480 determines that the dialysate is (i) properly sterilized, (ii) at a proper chemical composition, and (iii) at a proper temperature, control unit 480 causes a ready light 474 to illuminate, enabling patient 16 to press a "GO" or "START" button on control unit 480, which in turn causes outlet valve 464 to open and the filling of the patient to begin.

As illustrated below in FIG. 8E, scale 56 is in one embodiment combined with a heater 490 to heat fresh fluid within fill container 432. In an alternative embodiment, the fresh fluid is heated to the proper temperature prior to flowing through fill line 434 to fill container 432. Alternatively or additionally, sterilizing panels 462a/462b heat, or top off the needed heating, of fresh fluid residing within the fill container. Semi-permanent fill container 432 in combination with the hot water disinfection and the in-facility sterilization of CAPD sets 190 and 290 described above with FIG. 8A eliminate the need for refurbishing center 274 altogether. Treatment facilities 100a to 100j can accordingly operate self-sufficiently and independent of one another.

Referring now to FIGS. 8B to 8E, various embodiments of semi-permanent filling system 430, fill container 432, and energizing unit 460 are illustrated in more detail. As discussed above, fill container 432 can be removed from energizing unit 460 in certain instances as illustrated in FIG. 8C. Normally, however, fill container 432 sits within, and is acted upon by, energizing unit 460, as illustrated in FIG. 8B. To facilitate easy removal of fill container 432 from energizing unit 460, energizing unit 460 is generally three-sided, with sterilizing panels 462a/462b providing two sides and a front panel 470 connected to the sterilizing panels 462a/462b providing the third side. Fill container 432 is slid into and out from energizing unit 460 though the open back and/or top of unit 460. As illustrated, the top of energizing unit 460 is alternatively or additionally left open so that fill container 432 can be slid into and out from energizing unit 460 though the open top of the unit. The open top also allows for various structures to be mounted to the top of fill container 432. A notch 472 in front panel 470 allows an outlet pigtail 436 of fill container 432 to extend outside of the front panel 470 and unit 460.

Sterilizing panels 462a/462b and front panel 470 of energizing unit 460 can be made of metal, e.g., stainless steel or aluminum. Fill container 432 can be made of any of the plastic materials discussed above, such as polypropylene ("PP"), high density polyethylene ("HDPE"), low density Polyethylene ("LDPE"), polycarbonate ("PC"), glycol-modified polyethylene terephthalate ("PET-G"), polyvinyl chloride ("PVC"), and combinations thereof. In one preferred embodiment, fill container 432 is made of an ultraviolet ("UV") light transmissive material.

In the illustrated embodiment, ready light 474, e.g., a green light, is mounted to front panel 470 and powered via wires 476 running to control unit 480. Control unit 480 can be an off-the-shelf programmable logic controller ("PLC"), which accepts AC power from a source 42, accepts analogue and/or digital inputs from various external sensors, and sends analogue and/or digital outputs to external devices, such as, electrically actuated valves 464 and 466, sterilizing panels 462a/462b, and one or more heating element if provided. Control unit 480 can also power the sensors used with semi-permanent filling system 430, such as a temperature sensor 494, conductivity sensor 494/496, glucose sensor and/or one or more load cell for weigh scale 56.

Figure 8D:
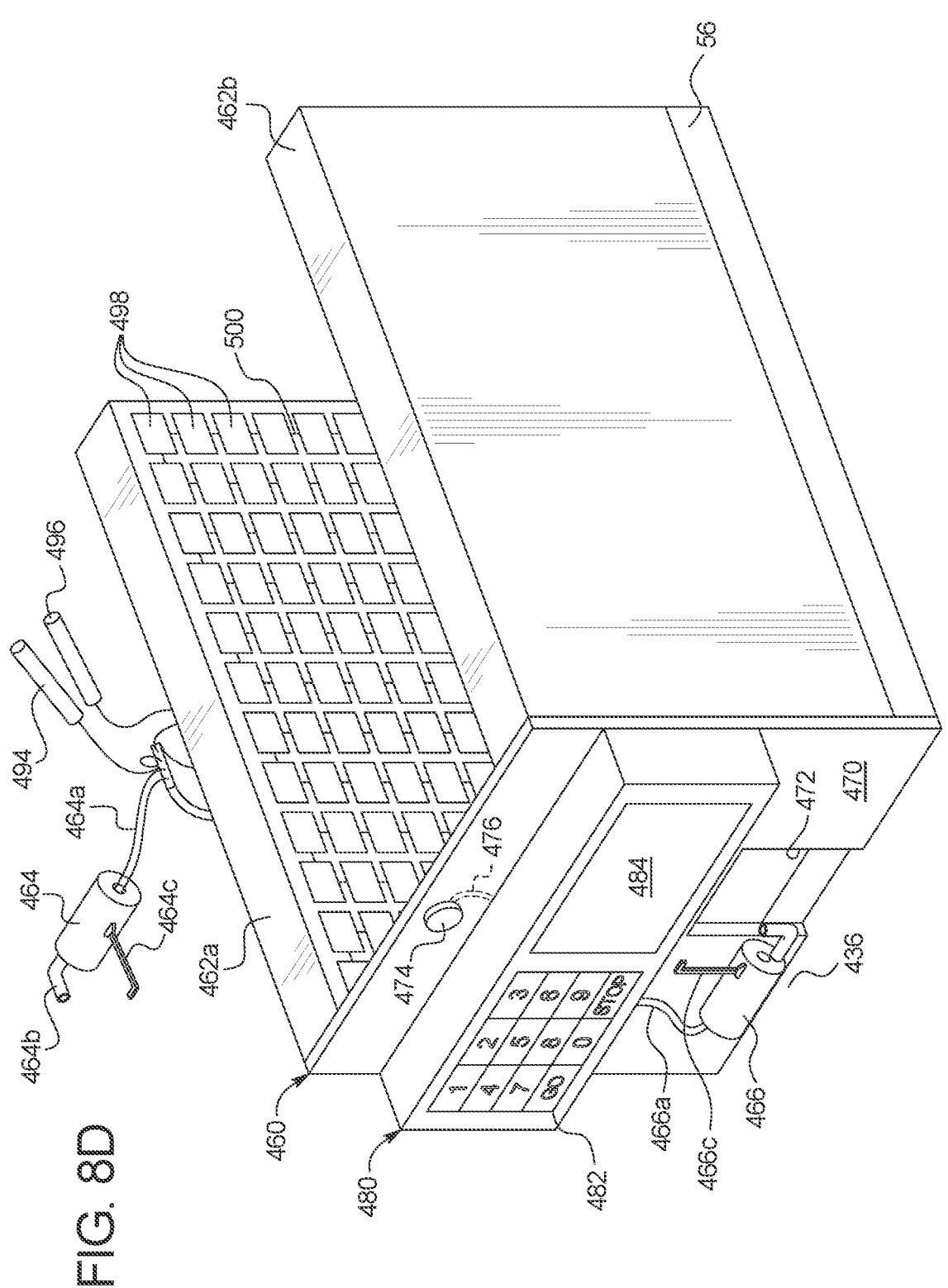
FIG. 8D is a perspective view of one embodiment of an energizing unit useable with the permanent or semi-permanent filling system of FIGS. 8A and 8B.

FIGS. 8B and 8D illustrate that control unit 480 can additionally include a touch panel keypad 482 for a user to enter values into the memory of control unit 480 and/or to initiate a command, such as "GO" and "STOP". Keypad 482 can for example be an electromechanical membrane switch keypad or a touch screen keypad. One or more memory within control unit 480 operates with one or more microprocessor of unit 480 to accept user and sensor inputs, employ algorithms that interrogate such inputs, and execute outputs to electrically actuate valves 464 and 466, sterilizing panels 462a/462b, one or more heating element 490, and the sensors 494 and 496. The one or more memory and processor also operate to display data as programmed on a display panel or device 484, such as a liquid crystal display ("LCD") panel or a light emitting diode ("LED") panel.

Ready light 474 or a similar marking or indicium can be displayed instead on display panel 484. Display panel 484 alternatively or additionally provides an indication of what percentage of a start-up (e.g., sterilization, and/or warming) procedure has transpired. Display panel 484 alternatively or additionally provides an indication of what percentage of a container 432 filling or emptying procedure has transpired. Display panel 484 alternatively or additionally walks patient 16 through the PD treatment setup steps and asks patient 16 to press "GO" when a step is completed, after which control unit 480 displays the next treatment step to be performed or begins treatment if setup has been completed.

Display panel 484 in an embodiment displays the numerals 0 to 9 that patient 16 presses to enter parameter valves using keypad 482. For example, one treatment setup step may be for the patient to enter the patient's prescribed fill volume. Display panel 484 prompts patient 16 to do so. Patient 16 uses keypad 482 to enter the volume (e.g., in liters). Display panel 484 displays the inputted volume back to patient 16. Patient 16 then presses the confirm or "GO" button. Control unit 480 converts the patient's volume or liter input to grams, so that the output of weigh scale 56 can be compared against the inputted weight. If patient 16 enters a fill volume that is greater than the capacity of container 432, display panel 484 can display an error message and prompt patient 16 to enter a different amount.

Alternatively, patient 16 uses keypad 482 to enter a patient identification ("ID") code. Control unit 480 is connected to a network linking all facility 100 computers 106a to 106f to 100n to all of the control units 480 located within facility 100. A storage or memory in communication with the network stores the patient's ID code along with treatment prescription information, such as fill volume and solution type. In one embodiment, once patient 16 enters his/her code, the storage or memory for the network recalls the patient's profile and sends a confirmation prompt to display panel 484, such as, "please confirm that you are Jane Doe". The patient confirms their identity, e.g., via pressing the "GO" button, or indicates that there is an identity mismatch, e.g., via pressing the "STOP" button. If an identity mismatch occurs, the network can display a message on display panel 484 requesting the patient to reenter their ID code and then repeat the confirmation process. If the identity mismatch continues, a facility professional 18 can be summoned. Once patient 16 confirms that the network has properly identified the patient, the network knowing the patient's profile automatically instructs control unit 480 to cause the proper fill volume to be filled into container 432 and prompts patient 16 to cause the proper type of dialysate to be made and/or delivered. Using the patient ID prevents patient 16 from entering a fill volume different than the patient's prescribed fill volume. The patient's ID and profile can be stored on the one or more memory device of control unit 480 alternatively or additionally to that of the facility network.

Further alternatively, patient 16 is provided with an identification ("ID") tag in the form of a card, wristband, keychain tag, necklace tag or the like. The tag includes a barcode, radio frequency tag ("RFID tag") or other readable structure, energy type or indicia. Energizing unit 460 is in turn provided with a corresponding reader, e.g., barcode, RFID or other reader (not illustrated) that is in data flow communication with control unit 480. Patient 16 in one embodiment scans his/her tag across the reader. The scanned information is delivered from control unit 480 to the network where the patient's profile is pulled. The network knowing the patient's profile automatically again instructs control unit 480 to cause the proper fill volume to be filled in container 432 and causes or prompts patient 16 to cause the proper type of dialysate to be made and/or delivered. Using the patient ID tag likewise prevents patient 16 from entering a fill volume different than the patient's prescribed fill volume and also prevents the patient from having to remember an ID code. The patient's ID profile can again be stored on the one or more memory device of control unit 480 alternatively or additionally to that of the facility network.

Both the ID code and ID tag embodiments can also require that a patient password be entered to prevent someone who improperly uses someone else's ID code or ID tag from receiving a treatment.

Once the proper fill volume is confirmed via any of the techniques discussed above, control unit 480 proceeds to cause energizing unit 460 to open fill valve 464, while keeping dispense valve 466 closed. Referring to FIGS. 8B and 8D, in the illustrated embodiment fill valve 464 and dispense valve 466 are spring-closed, energized-open, electrically actuated solenoid pinch valves. Valves 464 and 466 are accordingly fail safe because they will close automatically when power is removed or lost, placing semi-permanent filling system 430 into a no-flow state. Valves 464 and 466 are connected to control unit 480 and thus energizing unit 460 by electrical cabling 464a and 466a, respectively. Electrical cabling 464a and 466a enables control unit 480 to selectively power valves 464 and 466. The electrical cabling also provides a flexible connection of valves 464 and 466 to energizing unit 460, so that the valves can be lifted away from fill container 432 for its removal (FIG. 8D), while still remaining attached to energizing unit 460.

Valves 464 and 466 include a press-bar 464b and 466b, respectively, which are each mechanically attached to the body of the respective valve. Pigtail tubes 436 and 438 of fill container 432 become compressed between the valve plungers and the press-bars 464b and 466b when power is removed from the valves. Valves 464 and 466 each also include a locking pin 464c and 466c, respectively, which connect hingedly in one embodiment to the body of the valves and rotatably snap-fit into place onto their respective press-bars 464b and 466b. When snap-fitted into place, locking pins 464c and 466c prevent valves 464 and 466 from coming free from pigtails 436, 438 even when the valves are energized, pulling valve plungers free from press-bars 464b and 466b. When a facility professional 18 wishes to remove valves 464 and 466 from their respective tubes, e.g., to remove container 432 from energizing unit 460, facility professional 18 unlocks locking pins 464c and 466c, rotates the pins away from press-bars 464b and 466b, respectively, energizes valves 464 and 466 so that the valve plungers no longer pinch tubes 436, 438, and pulls valves 464 and 466 away from the tubes. With valves 464 and 466 removed, container 432 is free to be pulled away from energizing unit 460.

To manually energize valves 464 and 466 in one embodiment, e.g., for valve placement and removal, valve testing, or other reason, it is contemplated to allow facility professional 18 to enter a service mode via control unit 480. Each energizing unit 460 can have a service mode code that is entered via keypad 482. When the proper code is entered, energizing unit 460 enters a service mode and displays a number of service mode options to facility professional 18 on display panel 484. One such option could be to toggle or energize valves 464 and 466. A touchable button could be displayed on display device 484 for each valve 464 and 466. Or an instruction, such as "Touch 1 to open the fill valve", "Touch 2 to open the dispense valve", can be displayed on display device 484 so that keypad 482 can be used to toggle the valves. In any case, it is contemplated that when facility professional 18 selects a display or keypad button to open one of valves 464 or 466, that control unit 480 control unit maintain the valve in an open state for a predefined period of time without further button pressing from facility professional 18, so that the facility professional can have free hands to either apply valves 464 and 466 to tubes 436 and 438 or remove the valves from respective tubes.

When control unit 480 opens fill valve 464 and inlet pigtail 438, while keeping dispense valve 466 and outlet pigtail 436 closed, fill container 432 begins to fill with liquid, e.g., purified or sterilized water or purified or sterilized dialysate as discussed in more detail below. As liquid fills within fill container 432, hydrophobic vent 145 enables displaced air to escape. Also, weigh scale 56 measures the weight of the entering fluid. Weigh scale or load cell 56 is illustrated in FIGS. 8A, 8B, 8D and 8E. The top view of energizing unit 460 in FIG. 8E shows that weigh scale 56 can include a single sensor, e.g., a load cell or strain gauge. Alternatively, weigh scale 56 can include multiple sensors whose outputs are combined to produce a single accurate weight reading.

As alluded to above, the reading from weigh scale 56 is received by control unit 480 and compared against the commanded fill volume or weight. Once the actual volume or weight of liquid inside fill container 432 reaches the commanded volume or weight, control unit 480 closes fill valve 464 and inlet Pigtail 438. During the fill, it is contemplated to show patient 16 at display device 484 how much of the fill has transpired in relation to how much more filling needs to take place. The dynamic fill display can be shown as an ever-increasing instantaneous percentage number, as a character or shape that becomes increasingly colored with a fill color, and/or with an ever-increasing actual instantaneous volume number or weight number of the current fill. The fill display allows the patient to ascertain how much more filling time is needed. It is contemplated that patient 16 perform any needed draining while fill container 432 is filling. Patient 16 drains into reusable drain container 160 according to any of methods and alternatives and using any of the structure discussed above.

Once filling is completed, the next step depends upon the type of liquid and the state of the liquid that has been delivered to fill container 432. The present disclosure contemplates at least eight scenarios: (i) fill container 432 has been filled with unheated, purified dialysate, (ii) fill container 432 has been filled with heated, purified dialysate, (iii) fill container 432 has been filled with unheated, sterilized dialysate; (iv) fill container 432 has been filled with heated, sterilized dialysate, (v) fill container 432 has been filled with unheated, purified water, (vi) fill container 432 has been filled with heated, purified water, (vii) fill container 432 has been filled with unheated, sterilized water, and (viii) fill container 432 has been filled with heated, sterilized water.

Only under scenario (iv), where fill container 432 has been filled with heated, sterilized dialysate, can control unit 480 proceed to open dispense valve 466 and outlet pigtail 436, while keeping fill valve 464 and inlet pigtail 438 closed, to empty fill container 432 and fill patient 16. Each of the other scenarios (i) to (iii) and (v) to (viii) requires additional input from energizing unit 460. In particular, scenario (i) requires heat and sterilization, scenario (ii) requires sterilization, scenario (iii) requires heat, scenario (v) requires heat, sterilization, and dialysate additives, scenario (vi) requires sterilization and dialysate additives, scenario (vii) requires heat and dialysate additives, and scenario (viii) requires dialysate additives.

Regarding scenarios (i), (iii), (v) and (vii) that require heating of the liquid, it is contemplated to heat the liquid (a) prior to being delivered through fill line 434 to fill container 432, (b) while being delivered through fill line 434 to fill container 432, (c) while residing within fill container 432, and (d) any combination thereof. The liquid (water or dialysate) should be heated to about 37° C. (98° F.) or body temperature before being delivered to patient 16. Thus if facility 100 is located in a hot climate, the water or dialysate may be able to be stored in a non air-conditioned room and then heated the extra degrees to the desired temperature at fill container 432. Alternatively or additionally, the water or dialysate could be heated in a larger storage tank in a back room, e.g., in storeroom 150 discussed below in connection with FIG. 10, prior to delivery to fill container 432. Further alternatively or additionally, heating coils, e.g., heated to about 37° C. (98° F.), could be wrapped around fill line 434 to heat the fluid residing within the fill line. In either of the final two scenarios, heating at fill container 432 may not be required as specified in scenarios (ii), (iv), (vi) and (viii). However, for scenarios (i), (iii), (v) and (vii), heating at fill container 432 could be provided additionally, so that if needed, heating a couple extra degrees to reach 37° C. (98° F.) can be performed.

Figure 8E:
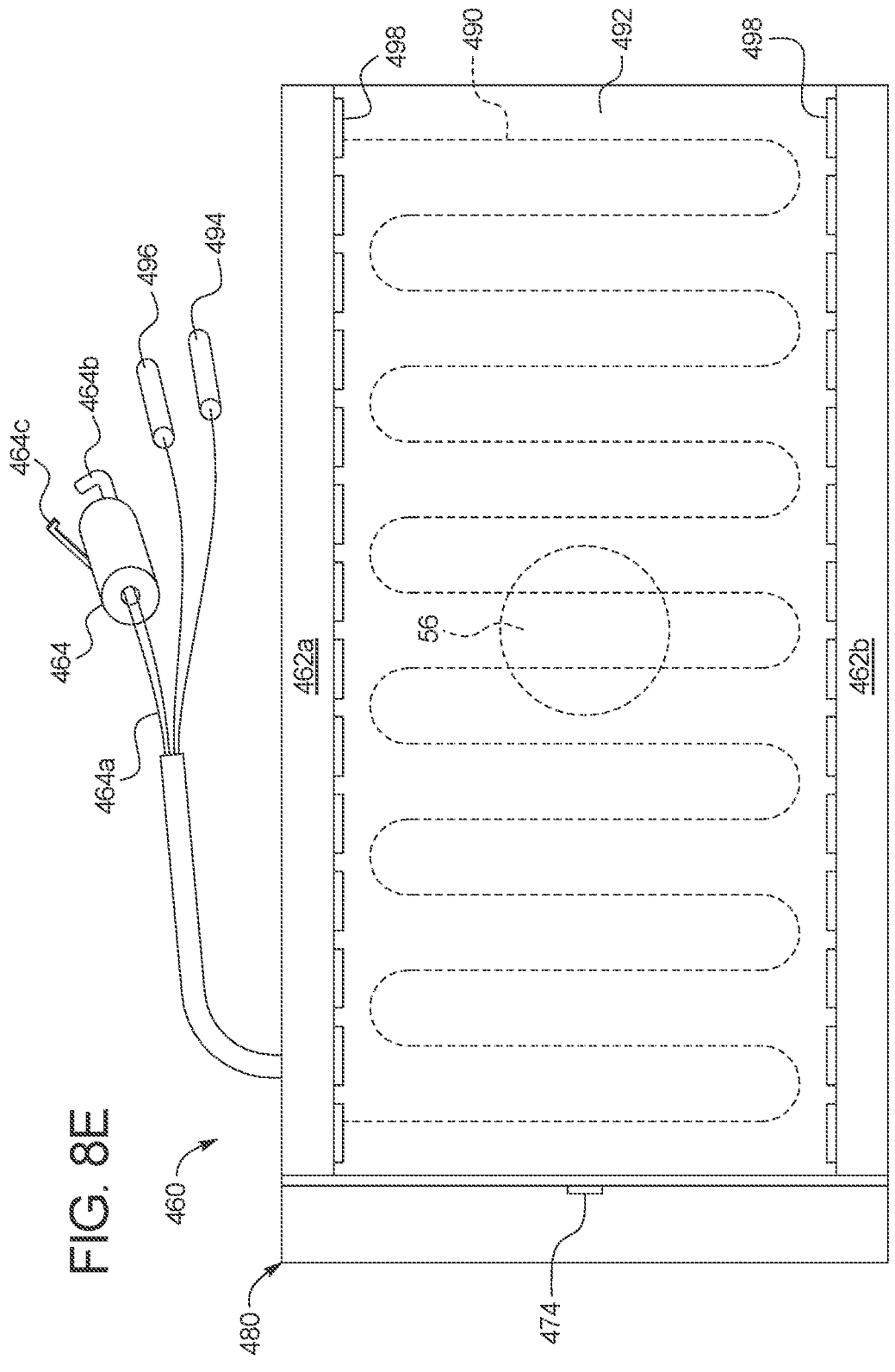
FIG. 8E is a top plan view of one embodiment of an energizing unit useable with the permanent or semi-permanent filling system of FIGS. 8A and 8B.
Figure 8F:
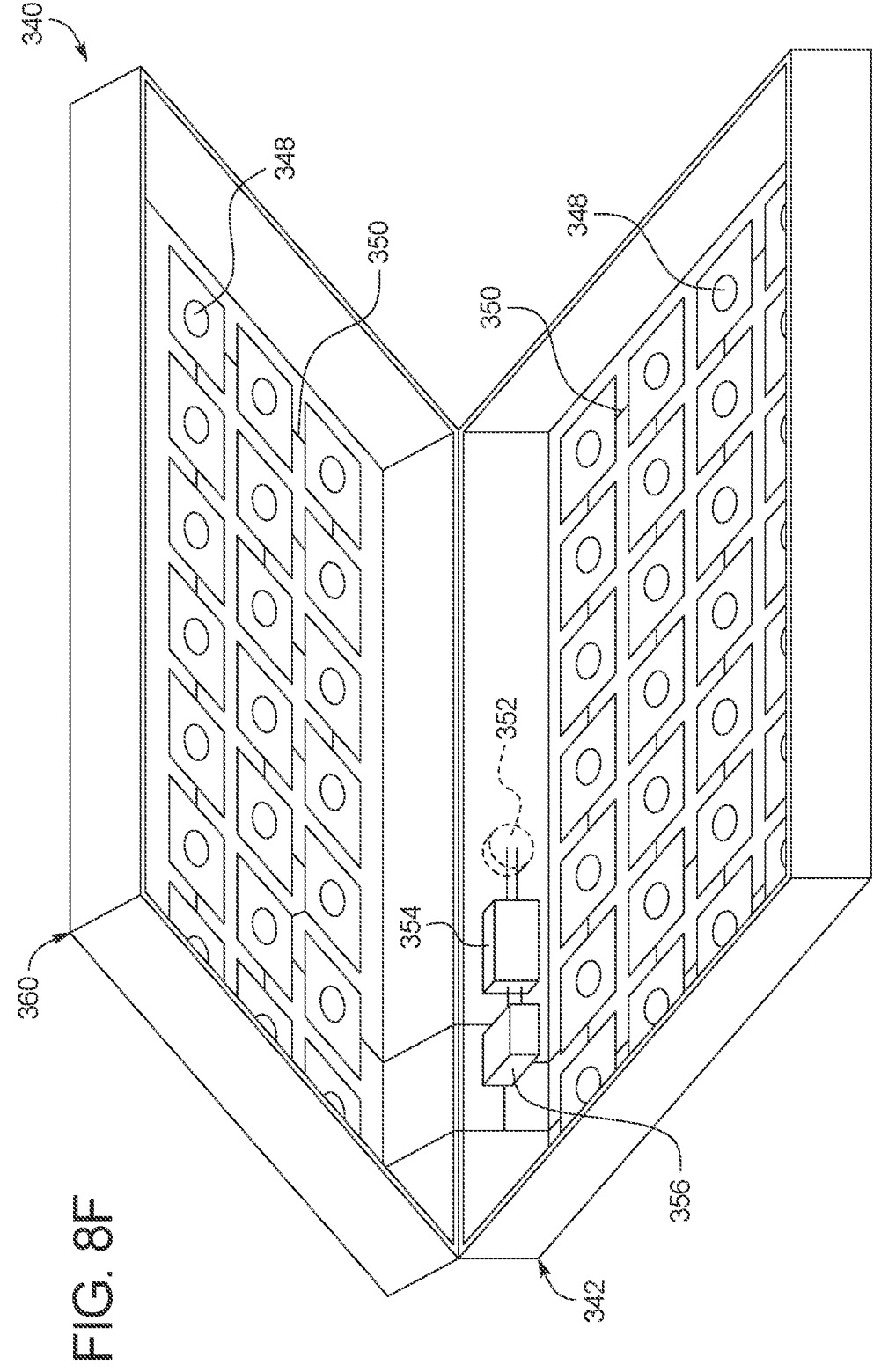
FIG. 8F is a perspective view of one embodiment of a sterilizing unit useable with the permanent or semi-permanent filling system of FIGS. 8A and 8B and any of the of the other system embodiments discussed herein.

In any of the heating scenarios just described that involve heating at fill container 432, it is contemplated to provide one or more resistive heating coil or element 490 as illustrated in FIG. 8E. In the illustrated embodiment, heating coil or element 490 resides within a heating plate 492 upon which fill container 432 sits. Heating plate 492 can in turn sit on top of the one or more sensor (e.g., load cell or strain gauge) of weigh scale 56. The constant weight of the heating plate 492, heating coil or element 490 and empty fill container 432 is zeroed out before weigh scale 56 reads the weight of fluid within fill container 432 or is subtracted from the detected weight of the combined empty fill container 432, heating plate 492, heating coil or element 490 and fill fluid.

Control unit 480 in one embodiment controls a power duty cycle (percentage on versus off or percentage of full power) to heating coil or element 490, so as to heat the water or dialysate as quickly and safely as possible to about 37° C. (98° F.). In one embodiment, two heating coils or elements 490 of the same overall resistance are provided, which combined extend to as to canvas the entire area of heating plate 492. A voltage detection circuit (not illustrated) is provided with control unit 480. The voltage detection circuit detects the incoming line voltage and relays same to the processing and memory of control unit 480. Control unit 480 also includes switching circuitry, such that if a higher line voltage is detected, e.g., 190 to 250 VAC, control unit 480 commands the switching circuitry to cause the dual, equal resistance heating coils or elements 490 to be powered in series. If a lower line voltage is detected, e.g., 80 to 140 VAC, control unit 480 commands the switching circuitry to cause the dual, equal resistance heating coils or elements 490 to be powered in parallel. The result is that coils or elements 490 output roughly the same amount of heating power or wattage regardless of the incoming line voltage. Filling system 430 can accordingly be used in different countries having different incoming line voltages and nevertheless use the same heating algorithm.

The duty cycle control algorithm that control unit 480 uses to heat water or dialysate uses temperature feedback from one or more temperature sensor 494 in one embodiment. Temperature sensor 494 is illustrated in FIGS. 8B, 8D and 8E and can be a thermistor or thermocouple in various embodiments. As illustrated in FIGS. 8B and 8C, to help maintain a sterile environment within fill container 432, a permanent metal, e.g., stainless steel, probe 442 extends down into the fill container. Probe 442 contacts the water or dialysate when fill container 432 is filling. Heat from the water or dialysate conducts up metal probe 442, which extends partly out of the top surface 450 of fill container 432. The portion of metal probe 442 extending out the top surface 450 of fill container 432 extends partway into a coupler 444, which is in one embodiment molded with fill container 432. Coupler 444 leaves room for temperature sensor 494 to be inserted into and held press-fittingly in place by the coupler as illustrated in FIG. 8B. Temperature sensor 494 dead ends against metal probe 442, so that heat from the water or dialysate can further conduct from probe 442 to temperature sensor 494, which generates a corresponding signal that is sent back to control unit 480.

FIGS. 8C and 8D illustrate that temperature sensor 494 can be pulled from coupler 444 of fill container 432 to remove fill container 432 from energizing unit 460, e.g., to replace temperature sensor 494, or for any other desired reason. Probe 442 can extend any desired distance into fill container 432 including down towards the bottom of the container.

Control unit 480 in one embodiment uses the signal from one or more temperature sensor 494 as feedback in its control algorithm. Generally speaking, the further away actual liquid temperature as sensed by one or more temperature sensor 494 is below the commanded temperature, e.g., about 37° C. (98° F.), the higher the heating duty cycle applied to coils or elements 490. It is contemplated for control unit 480 to store and use proportional, integral and derivative ("PID") control to heat the water or liquid to the commanded temperature quickly and with little temperature overshoot.

In the above scenarios (iii), (iv), (vii) and (viii) not requiring sterilization at fill container 432, sterilization is performed in backroom 150 or at an off sight, e.g., central, location after which the sterilized fluid is shipped to facility 100. Sterilization performed locally in backroom 150 is done, e.g., in a large vessel, via any technique listed herein, such as, through the use of hydrogen peroxide vapor, gamma irradiation, peracetic acid, ethylene oxide, ethanol, formalin, glutaraldehyde, low energy electron beam and/or any other sterilization method known in the art. Performing certain of these methods in backroom 150, away from patient 16, is preferred for safety reasons.

Regarding scenarios (i), (ii), (v) and (vi) above requiring final sterilization at fill container 432, FIGS. 8D and 8E illustrate that sterilizing panels 462a and 462b are provided with energizing unit 460 in one embodiment. Sterilizing panels 462a and 462b in the illustrated embodiment each supply a plurality of plurality of ultraviolet ("UV") lights 498, such as UV light-emitting diodes (UV-LED's) or UV lamps. The UV lights 498 are connected in series in one embodiment via one or more wire or printed circuit board trace 500. It is contemplated in one embodiment for the inner surfaces of sterilizing panels 462a and 462b to be ceramic or FR-4 printed circuit boards upon which one or more copper trace 500 is formed. The UV lights 498 are surface mounted to the trace wires 500, e.g., either in series or parallel as desired. Alternatively, wires 500 form a mesh to which the UV lights 498 are hard-wired, soldered or are otherwise connected electrically. Still further alternatively, UV lights 498 are UV bulbs that thread or plug into sockets provided by or at the inside surfaces of sterilizing panels 462a and 462b. The UV bulbs can likewise be wired together in a series or parallel relationship.

To aid in the sterilization of liquid within fill container 432, and to increase energy efficiency, it is contemplated to form or coat top surface 450, front surface 452, rear surface 454, and if needed the bottom surface of fill container 432 (see FIG. 8C) with a UV light reflective material. Side surfaces 456 and 458 of fill container 432 located directly adjacent to sterilizing panels 462a and 462b, respectively, are made of a UV light transmissive material. As illustrated in FIG. 8C, it is also contemplated to make side surfaces 456 and 458 of fill container 432 relatively broad and front surface 452 and rear surfaces 454 relatively narrow, so that the depth of UV light penetration needed is lessened For example, the horizontal length of side surfaces 456 and 458 can be three or four times as long as the horizontal length X of front and back surfaces 452 and 454.

The total disinfecting power from the cumulative light emitted by each of the UV lights 498 of sterilizing panels 462a and 462b is enough by an engineering factor to sterilize the water or dialysate within a reasonable period of time, e.g., five to ten minutes, or the time duration needed to also heat the water or dialysate. It is believed that UV disinfection is more effective when treating highly purified water, e.g., reverse osmosis or distilled water. Suspended particles can become a UV sterilization problem because microorganisms buried within particles are shielded from the UV light. It is contemplated however to purify the water or dialysate prior to reaching fill container 432 via any of the purification systems discussed herein. The purification system can for example be located in backroom 150 to pre-filter and remove larger organisms before they reach fill container 432. The pure or ultrapure water or dialysate received in fill container 432 also clarifies the liquid to improve light transmittance and therefore UV dose throughout the container 432. Also, because the water or dialysate is trapped within container 432, and sterilized on a batch basis, the UV light should have the time and opportunity to impinge any remaining particles or microorganisms trapped within the liquid.

It is further contemplated to rely upon any heat delivered by UV lights 498 to the water or dialysate in the overall heating of same. Thus it is contemplated that a combination of ambient pre-heating, heating from coils or elements 490, and heating from UV lights 498 is sufficient to heat the water or dialysate to body temperature within a reasonable period of time, e.g., the time needed for the patient to drain and/or the time needed for proper UV sterilization.

In the illustrated embodiment, there is no feedback sensor for sterilization. Adequate sterilization time is determined empirically base upon certain factors, such as, facility water supply quality, type and amount of pre-filtering, sterilization volume within fill container 432, and power output from sterilizing panels 462a and 462b. Thus the sterilization time can be seen as a benchmark. If ambient pre-heating, heating from coils or elements 490, and heating from UV lights 498 can be effectively accomplished at fill container 432 within or around the time needed for UV sterilization, then such heating may be preferred so that separate large batch heating in backroom 150 is not needed and is instead done on an on-demand basis at fill container 432. In such a case, backroom 150 may only need a water or dialysate purification unit, which purifies the liquid needed for each of the patient stations 186a to 186n. It is further contemplated to insulate each of the lines, e.g., fill line 434, leading to patient stations 186a to 186n to lessen heat loss during fluid travel.

It is contemplated to automate the heating and/or sterilization associated with energizing unit 460 so that patient 16 does not have to commence those processes. To do so, control unit 480 in one embodiment waits until a certain amount of fill liquid is introduced into fill container 432 before firing heating elements or coils 490 and/or sterilization panels 462a and 462b. Once weigh scale 56 signals that a predefined amount of fill liquid is present (e.g., ⅛th full), control unit 480 actuates heating elements or coils 490 and/or sterilization panels 462a and 462b. Heating elements or coils 490 can be actuated before or after sterilization panels 462a and 462b. In an embodiment, control unit 480 requires both the predefined weight signal from scale 56 and knowledge that valves 464 and 466 are in their fill state to actuate heating elements or coils 490 and/or sterilization panels 462a and 462b. The combination requirement prevents a false weight signal (e.g., item placed on fill container 432) from inadvertently activating the heaters and sterilizing panels when no fill is taking place.

Figure 8G:
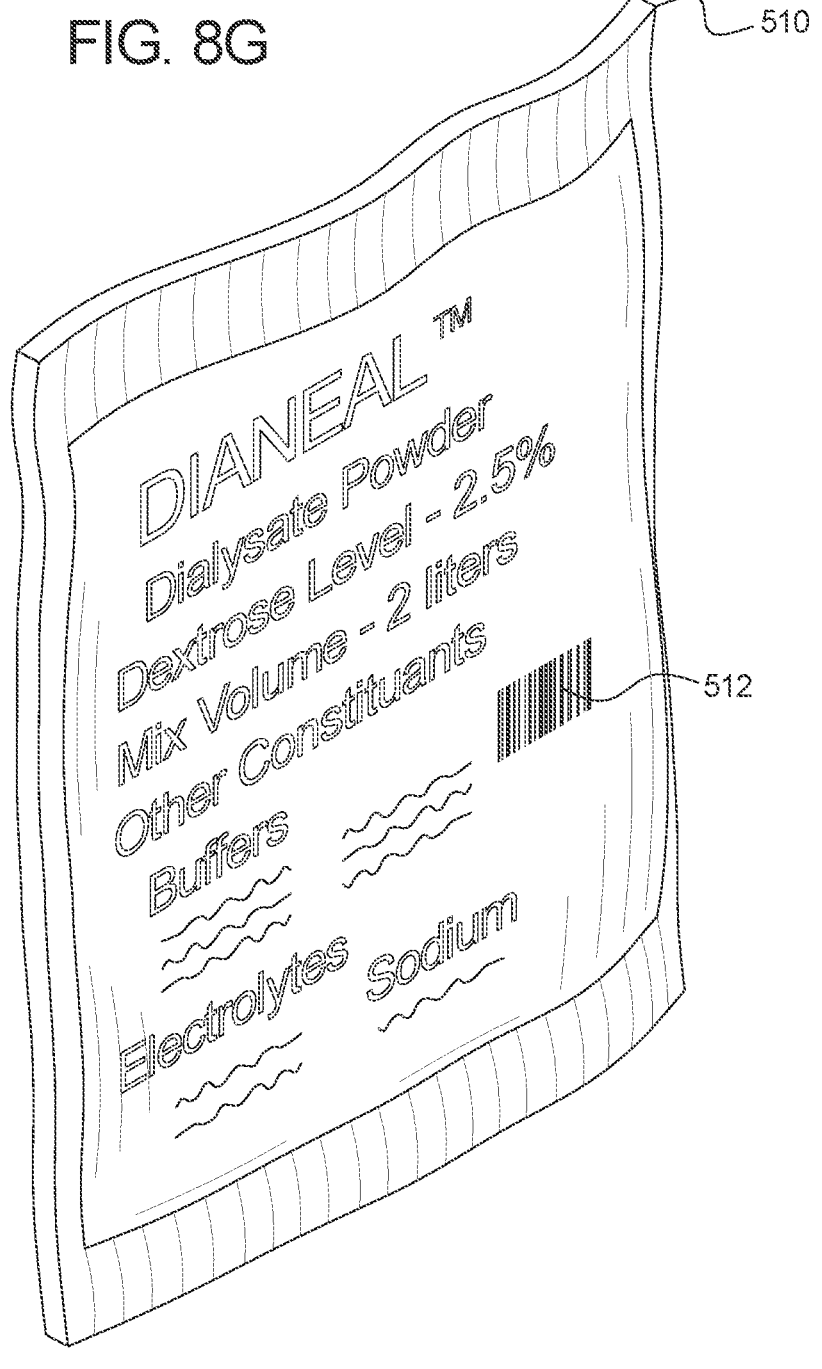
FIG. 8G is a perspective view of one embodiment for a packet containing dialysate additives, which when mixed with a defined volume of water produce chemically balanced dialysate.

Referring now to FIG. 8G, for any of the scenarios (v) to (viii) listed above in which additives need to be mixed with purified water to produce dialysate, it is contemplated to provide a sterilized packet 510 that contains powdered additives, which when mixed with the proper volume of purified or disinfected water form a correctly formulated prescribed dialysate. In an embodiment, patient 16 receives a prescribed sterilized packet 510 from facility professional 18 upon approaching front desk 104 (FIG. 3). In an alternative embodiment, patient 16 pre-purchases multiple packets 510 and brings one or more packet 510 to facility 100 each visit for use. Patient 16 can be provided with packets 510 of varying formulations that allow the patient to tailor the treatment based upon what is needed that day. For example, if patient 16 feels heavy and overhydrated on a particular day, the patient could choose a packet 510 prescribed by a doctor for removing extra ultrafiltration ("UF"). Or if patient 16 has had UF removed in a previous exchange but wants more clearance, the patient could choose a prescribed low UF removed packet.

Packets 510 in the embodiment illustrated in FIG. 8G provide certain information such as dialysate type, e.g., by tradename, such as DIANEAL™ or EXTRANEAL™ PD solution. The illustrated packet 510 also specifies dialysate additive constituents, such as, osmotic agents (e.g., glucose level, dextrose level and/or other high and low molecular weight agent levels), buffers (e.g., lactate level, acetate level, and/or bicarbonate level), and/or electrolytes (e.g., sodium level, calcium level, magnesium level, and/or potassium level). The illustrated packet 510 further specifies the purified water volume that needs to be mixed with the additives, e.g., two liters. It is expressly contemplated to provide one or more electrolyte, e.g., sodium, in a concentration that is higher than what is normal for a peritoneal dialysis solution. The reason for this is to raise the conductivity of the dialysate mixed from purified or sterilized water and additives to a level that can be sensed by sensors 494 and 496 as discussed below. Any one or more electrolyte could be raised as needed for such purpose but to a level that is still physiologically safe for patient 16.

Packets 510 can be sterilized then sealed, e.g., vacuum sealed, or sealed, e.g., vacuum sealed, then sterilized. Sterilization can be performed via any of the methods discussed herein. Packets 510 can be configured to be torn open at a break point, cut open near a seam or be provided with a tear-away tab. In an embodiment, packets 510 are also provided with readable indicia 512, such as a barcode, that is read by a suitable reader (not illustrated) located at filling system 430. Readable indicia 512 provides information to control unit 480, such as solution type, water mix volume needed, and/or expiration date. It is therefore expressly contemplated to let packet 510 tell control unit 480 how much purified water to allow into fill container 432, under the assumption that the patient 16 has been provided with the correct type of packet 510. The patient identity checks discussed above may accordingly not be needed or may be performed in addition to, or as a check upon, the information provided by packet 510. Control unit 480 can also maintain an internal clock of date and time, so that if control unit 480 detects that packet 510 has expired, control unit 480 sounds an alarm, prevents filling, and/or notifies a facility professional 18.

FIGS. 8B and 8C illustrate that fill container 432 is provided in one embodiment with a removable, e.g., threaded cap 440. Control unit 480 via display device 484 in an embodiment prompts patient 16 to remove cap 440, open packet 510, and pour the contents of packet 510 into an unfilled fill container 432. Control unit 480 via display device 484 can then display a selectable "PACKET EMP-TIED" button or display a message such as "Touch GO when packet is completely empty". Once patient 16 has confirmed that packet 510 has been emptied into container 432, subject to any identity verification requirement, control unit 480 commands fill valve 464 to open to being filling. The turbulence of purified water entering fill container 432 thoroughly dissolves and mixes the granulated additives of packet 510.

FIGS. 8B to 8E illustrate that energizing unit 460 in an embodiment also provides a conductivity sensor 496. Conductivity sensor 496 operates alongside temperature sensor 494 to form a conductivity sensor pair. Control unit 480 uses the signal from temperature sensor 494 to compensate for temperature and the signal from conductivity sensor pair 494 and 496 to produce an accurate conductivity reading. As illustrated in FIGS. 8B and 8C, to help maintain a sterile environment within fill container 432, a permanent metal, e.g., stainless steel, probe 446 extends down into the fill container as far as is needed. Probe 446 contacts the water or dialysate when fill container 432 is filling. Electricity flows through conductivity sensor 496, probe 446, the dialysate, probe 442, and sensor 494 to and from a sensing circuit located within control unit 480. The higher the conductivity of the dialysate, the higher the current sensed at the sensing circuit.

The portion of metal probe 446 extending out the top surface 450 of fill container 432 extends partway into a coupler 448, which is in one embodiment molded with fill container 432. Coupler 448 leaves room for conductivity sensor 496 to be press-fittingly inserted into and held in place by the coupler as illustrated in FIG. 8B. Conductivity sensor 496 dead ends against metal probe 446, so that electricity from the dialysate can further conduct from probe 446 to temperature sensor 496, back to control unit 480. FIGS. 8C and 8D also illustrate that conductivity sensor 496 can be pulled from coupler 448 of fill container 432 to remove fill container 432 from energizing unit 460, to replace conductivity sensor 496, or for any other desired reason. Probe 448 can extend any desired distance into fill container 432, including down towards the bottom of the container.

Control unit 480 in one embodiment uses the signal from conductivity sensor pair 494 and 496 as confirmation that the dialysate has been mixed with the proper volume of purified water. The primary mixing control is to fill container 432 to the prescribed amount. If that is done, the dialysate should be mixed properly. The conductivity reading can be used as a confirmation that the dialysate is properly mixed. When the powdered additives of packet 510 are dissolved in only a small amount of purified water, the conductivity level should be higher than when the additives are dissolved in the prescribed volume. Control unit 480 monitors the dropping conductivity level as filling occurs and either confirms that the actual final dialysate conductivity is within an acceptable prescribed range or alarms and/or notifies facility professional 18 when the final conductivity level is outside of (higher or lower) the accepted conductivity range.

Based on the foregoing description of FIGS. 8A to 8G, in one scenario in which all three of heating, sterilization and dialysate mixing is taking place at permanent or semi-permanent filling system 430, the sequence of events in one example proceeds as follows (steps do not have to follow in the stated order):

(i) 192 patient 16 arrives at patient station 186b with a dialysate additive packet 510 brought from home or obtained at front desk 104, along with a reusable drain container 160, CAPD set 190 or 290 and a new patient transfer set cap 198a;

(ii) 193 patient 16 places CAPD set 190 or 290 and new patient transfer set cap 198a into sterilizing unit 340 and commences final sterilization of the set and cap;

(iii) 194 patient 16 opens packet 510, empties its contents into empty fill container 432, and closes the container;

(iv) 195 patient 16 enters a volume directly, enters a patient ID, scans an ID tag or scans packet 510 to load a fill volume into control unit 480, and upon patient and volume verification, filling system 430 begins a filling procedure that includes filling container 432 with water and activating fluid heating and final fluid disinfection automatically at some point during filling;

(v) 19 during filling, patient 16 removes existing patient transfer set cap 198a, connects CAPD set 190 or 290 to the patient's transfer set, reusable drain container 160, and fill container pigtail 436 (CAPD set 190) or just to the patient's transfer set and reusable drain container 160 (CAPD set 290), and commences a patient drain;

(vi) when the drain is complete, and when ready light 474 is lit indicating that dialysate volume, sterility, temperature and composition are satisfactory for patient delivery, patient 16 either (a) commences a flush sequence from fill container 432 to reusable drain container 160, followed by a dispense to patient sequence from fill container 432 to the patient 16 using GO and STOP buttons, flow control device 90 and CAPD set 190, or (b) removes the distal end of CAPD set 290 from reusable drain container 160, connects same to fill container pigtail 436, and commences a dispense to patient sequence from fill container 432 to the patient 16 using GO and button and perhaps a pinch clamp if CAPD set 290 requires priming;

(vii) when the dispense to patient or patient fill sequence is complete, the difference between drain fluid weight and patient fill fluid weight is recorded manually or electronically as ultrafiltration ("UF") removed, which can be logged by patient 16 and/or reported to facility professional 18 for storage at treatment facility 100;

(viii) patient collects used CAPD set 190 or 290, used patient transfer set cap 198a, and loaded reusable drain container 160, returns same to front desk 104, and collects a deposit if posted; and (ix) used CAPD set 190 or 290, used patient transfer set cap 198a, and loaded reusable drain container 160 are emptied if needed and disinfected later that day or overnight.

It should be appreciated that in the above scenario, treatment facility 100 is completely self-sufficient, requiring no deliveries of pick-ups. The facility need only provide one or more water purification unit, one or more disposable disinfection unit (e.g., hot water circulation unit), and possibly one or more fill water pre-heating unit. The only waste produced is the wrapper for packet 510.

Figure 9:
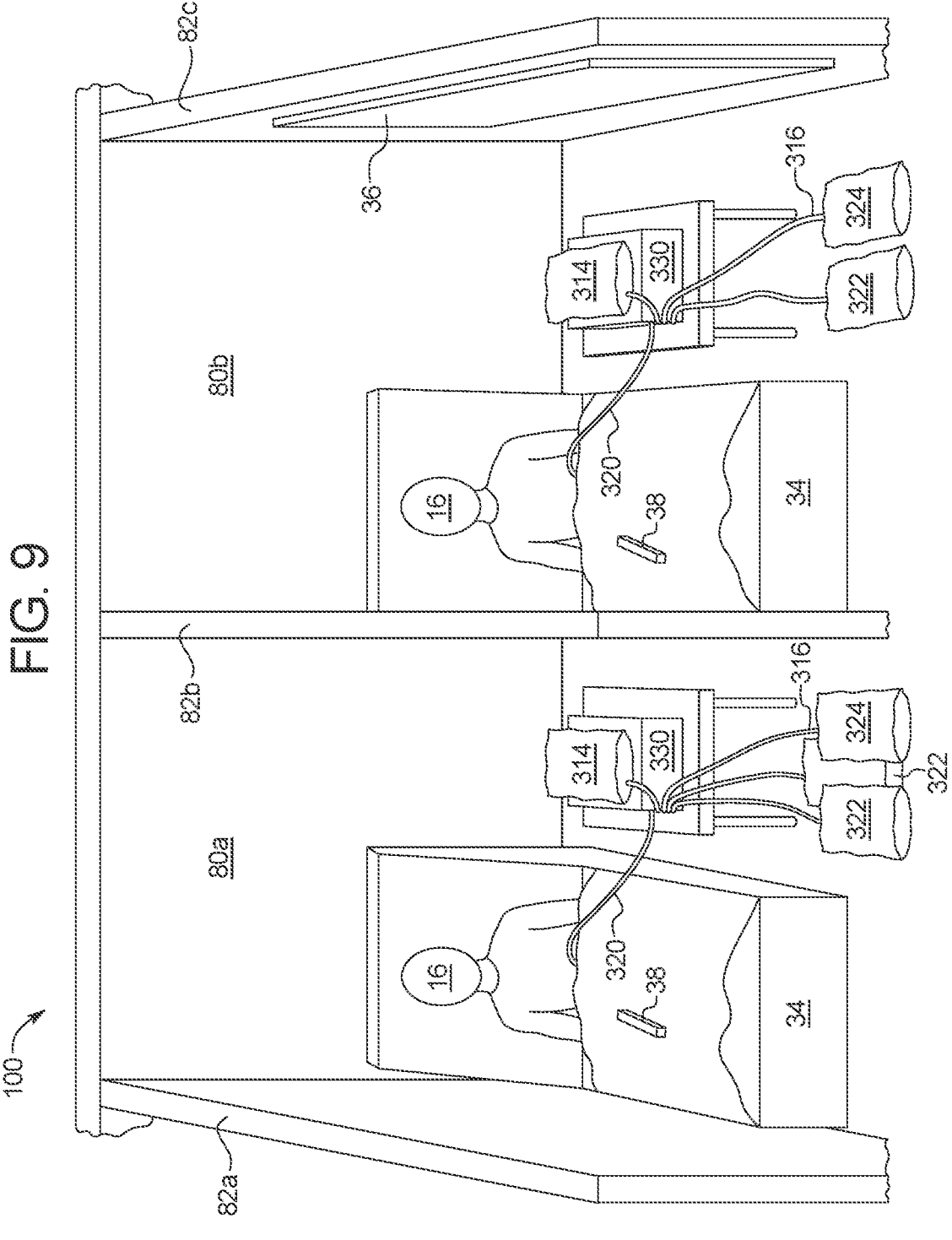
FIG. 9 is a perspective view of one embodiment for structuring an automated peritoneal dialysis ("APD") treatment area of an exchange facility of the present disclosure.

Referring now to FIG. 9, an alternative automated peritoneal dialysis ("APD") machine embodiment is illustrated. Here, once patient 16 is authorized or verified at desk 104, patient 16 is allowed to proceed to a further alternative treatment facility 100, in which an APD machine 330 is used. APD machines 330 are discussed in detail below in connection with FIGS. 10 and 12. In FIG. 9, alternative patient stations 80a and 80b (any number of which could be provided), divided by walls 82a to 82c are horizontally juxtaposed as opposed to being laid out in a circular manner as is illustrated in FIG. 4. Horizontally juxtaposed APD patient stations 80a and 80b can have any one, or more, or all of chair, sofa, bed, or the like 34, television 36, remote control 38, desk or table 40, and/or alternating current wall outlet 42 discussed above in connection with FIG. 4. Station's 80a and 80c can be closed using a curtain, wall, and/or door, for example. In the illustrated embodiment, APD patients 16 are provided with beds 34. APD machines 330 are placed adjacent to the beds 34, so that a patient line 320 can extend from a heater or fill bag 314 bag to patient 16.

The APD treatment is discussed below in connection with FIG. 12. One point worth noting here is that APD machines 330 can operate with multiple supply bags 322. Supply bags 322 may all contain the same kind of dialysate, e.g., DIANEAL™ PD solution. Alternatively, to tailor a PD treatment, supply bags 322 may contain different kinds of dialysate, e.g., two bags having DIANEAL™ PD solution and a single final bag having EXTRANEAL™ PD solution. It should also be appreciated that APD treatments using APD machines 330 with the facilities 100 of the present disclosure can use only a single supply bag 322 to perform only a single exchange, and wherein the single supply bag 322 may be placed atop machine 330 for heating. In FIG. 9, a heater bag 314, which can be used with multiple supply bags, is placed atop a heater pan located at the top of APD machine 330.

APD patients using machine 330 drain from a cassette, through a drain line 316, to a drain bag 324. APD patients using machine 330 fill from a supply bag 332 into heater bag 314, in which the PD solution is heated, e.g., to thirty-seven ° C., and then from heater bag 314 to the patient's peritoneum.

Referring now to FIG. 10, a top plan view shows one possible layout for a facility 100 used in any of the scenarios and settings discussed above in FIGS. 1 to 6. As discussed above in connection with FIGS. 1 and 2, facility 100 can be located in any suitable type of building, such as a standalone building, building along a busy city street, building in a mall, building as part of a larger building, transportation stations and the like. Facility 100 can also be located at a worksite or within a housing unit, so that patients can conveniently receive treatment before, during or after work to disrupt their work or home schedules as little as possible. Facility 100 can further alternatively be located within or nearby a housing unit, hostel or other temporary dwelling location, to allow residents of the unit or dwelling to receive convenient treatment without having to own their own dialysis equipment. Such a facility is especially useful in developing countries in which many or most residents do not have access to or the means to have dedicated home dialysis equipment. Also, certain countries provide temporary dwelling locations near work, so that employees can live near work during the week and return home on the weekend. The facilities of the present disclosure can be located at or near any such temporary dwelling location.

Facilities 100 allow the patient to perform exchanges before, during and/or after work as desired. The patient can for example perform a first exchange at a facility 100 located between home and work, perform a second exchange at a second facility 100 nearer to or at work during work, and perform a third exchange returning home from work at the original facility 100. System hub 520 of systems 10 and 110, discussed below in connection with FIGS. 14 and 15, enables patient data from multiple facilities 100 to be collected and analyzed together as if the patient had used only one facility 100.

As illustrated in FIG. 10 and above in connection with FIGS. 1 to 3, facility 100 includes a door 102 through which patients 16 enter. Once patients 16 enter through door 102, the patients approach a desk 104 (also illustrated in FIG. 3) to speak with facility professionals manning computers 106a to 106f. While facility 100 in FIG. 10 shows room for six facility professionals 18 (FIG. 3) manning six computers 106a to 106f, facility 100 can instead have any desired number of computers 106 (referring generally to any of computers 106a to 106f) and/or facility professionals. For example, in a smaller community setting, facility 100 may have only a single computer or professional. Computers 106 can be desktop computers, laptop computers, tablets or hybrid computers/tablets. Mobile laptop computers, tablets and hybrid computers/tablets enable facility professionals 18 to move about facility 100 and perform multiple functions, such as oversee duties at front desk 104, work the desks in the different rooms of facility 100, provide care or instructions to the patients, and/or operate a supply room. In the illustrated embodiment, computers 106 communicate with a web portal 524 or 560 (illustrated below in FIGS. 14 and 15) wirelessly via wireless transceiver 108.

Once the patient is verified according to any of the methods or procedures discussed herein, the patient enters a hallway via door 110 and proceeds through the hallway until reaching an appropriate, clearly marked exchange room door 112, 114 or 116. The exchange room accessed via door 112 is a batch peritoneal dialysis treatment area 200, in which multiple peritoneal dialysis patients can be filled off of a same large batch of a specified type of solution, and which is discussed in detail in connection with FIG. 11. The exchange room accessed via door 114 is an automated peritoneal dialysis ("APD") machine treatment area 300, in which multiple patients each use an in-center APD machine, and which is discussed in detail in connection with FIG. 12. The exchange room accessed via door 116 is a continuous ambulatory peritoneal dialysis ("CAPD") treatment area 400, in which multiple patients each use CAPD exchange equipment, and which is discussed in detail in connection with FIG. 13. Facility 100 may have one, or more, or all of batch peritoneal dialysis treatment area 200, APD machine treatment area 300, and/or CAPD treatment area 400. The treatment area(s) of facility 100 may further alternatively be a mixture of any combination of treatment areas 200, 300 and 400.

FIG. 10 illustrates that batch peritoneal dialysis treatment area 200 includes a plurality of larger dialysis solution tanks 210*a*, 210*b*, 210*c* and 210*d*, which can each hold different dextrose or glucose level dialysates. Alternatively, the dialysate solution tanks 210*a* to 210*d* can hold dialysates that are formulated at low levels of dextrose or glucose or without dextrose or glucose. For example, dialysates without glucose are marketed by the assignee of the present disclosure under the tradenames EXTRANEAL™ and NUTRINEAL™. Known and approved dextrose levels are, e.g., 0% to 4.25%, and known and approved glucose levels are, e.g., 0% to 3.86%.

Batch peritoneal dialysis treatment area 200 also includes a plurality of common drain areas 250. Alternatively, the patient inside batch peritoneal dialysis treatment area 200 drains to a drain bag or individual drain. A plurality of sterilizing units 244, such as ultraviolet ("UV") sterilizers, are provided at dialysis solution tanks 210*a*, 210*b*, 210*c* and 210*d* and common drain areas 250 to allow the patient to connect and disconnect from each in a sterile manner. Batch peritoneal dialysis treatment area 200 may or may not require a patient disposable but in any case should produce less disposable waste than APD machine treatment area 300, and/or CAPD treatment area 400.

Because facility 100 can use hundreds of disposable sets in a single day, it is desirable to recycle and/or reuse as much of the disposable set as possible. Some portions of the set and/or packaging remain dry and can simply be re-sterilized for reuse. Such disposable portions include, for example, plastic portions that do not contact the effluent dialysate, e.g., caps, plastic bags, paper and cardboard from the packaging. Any tubing and pumping sections associated with a disposable set that come into contact with fluid however become a biohazard after use and are dealt with more carefully. The wet disposable portions can be collected in a sealed container so as not to contact outside materials, preventing the spread of the biohazard. The container is transported to a place in which the wet disposable portion is disinfected with a chemical sterilizing solution (or other as listed above) and recycled or reused. The disinfection here takes place in a biohazard environment because there is the potential for exposure to human blood which may be infected, for example, by hepatitis or Acquired Immune Deficiency Syndrome ("AIDS"). If the tubing cannot be disinfected for recycling or reuse, it is instead packaged, labeled as a biohazard and given to a licensed biohazardous waste hauler.

Likewise, any used dialysate or fluid that cannot be recycled or reused is also disposed as a biohazard. CAPD patients often dispose of effluent dialysate by pouring the fluid into a sewage system. Facility 100 however may disinfect the used dialysate before discarding it because the facility may be disposing of hundreds of liters of used dialysate every day. Particular care is taken to ensure that the disposal of any biohazard materials complies with Control of Substances Hazardous to Heath ("COSHH"), Occupational Safety and Health Administration ("OSHA") and Environmental Protection Agency ("EPA") regulations.

When the patient enters batch peritoneal dialysis treatment area 200, the patient approaches desk 120*a* and hands an attendant an order received from one of the computers 106 at front desk 104. Or, the order is sent from one of the front desk computers 106*a* to 106*f* to treatment area 200 computer 106*g*. Further alternatively, facility professional 18 walks the patient from the front desk area to batch peritoneal dialysis treatment area 200 and enters the patient's order, e.g., via the professional's mobile laptop computer, tablet or hybrid computer/tablet. In any case, the order is entered for billing purposes at this time. The patient may or may not be charged a co-pay amount at front desk 104. If there is any disposable that is needed for the treatment at batch peritoneal dialysis treatment area 200, a facility professional 18 pulls the disposable from behind treatment area desk 120*a* or enters a storeroom 150 through door 122 to obtain the disposable. Again the patient at batch peritoneal dialysis treatment area 200 may not need any disposable.

If the patient in batch peritoneal dialysis treatment area 200 is currently full of used dialysis fluid, the patient connects to one of common drain areas 250 via the patient's transfer set. Such connection can be made with sterilizing unit 244 and/or with a cleaning agent such as rubbing alcohol. The patient then drains the used fluid, e.g., in a sitting position, to allow for as complete a drain as possible. After drain, the patient proceeds to a designated dialysis solution tank 210*a*, 210*b*, 210*c* or 210*d* for filling. The patient again connects his or her transfer set to the designated solution tank, e.g., using sterilizing unit 244 and/or with a cleaning agent such as rubbing alcohol. The patient then performs a peritoneal dialysis fill procedure, which is explained in more detail in connection with FIG. 11.

Figure 14:
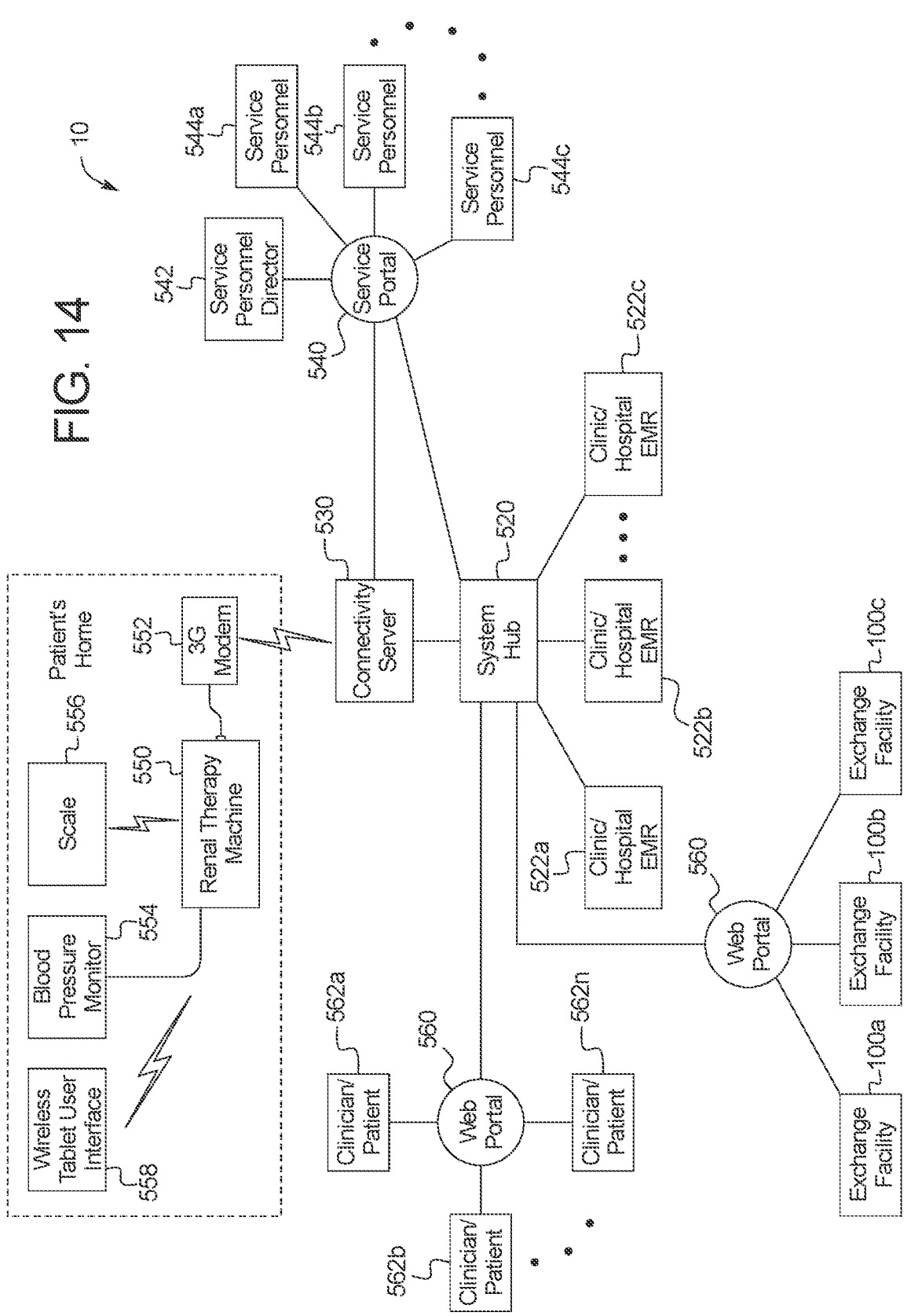
FIG. 14 is a schematic block diagram of one embodiment for a system according to the present disclosure.
Figure 15:
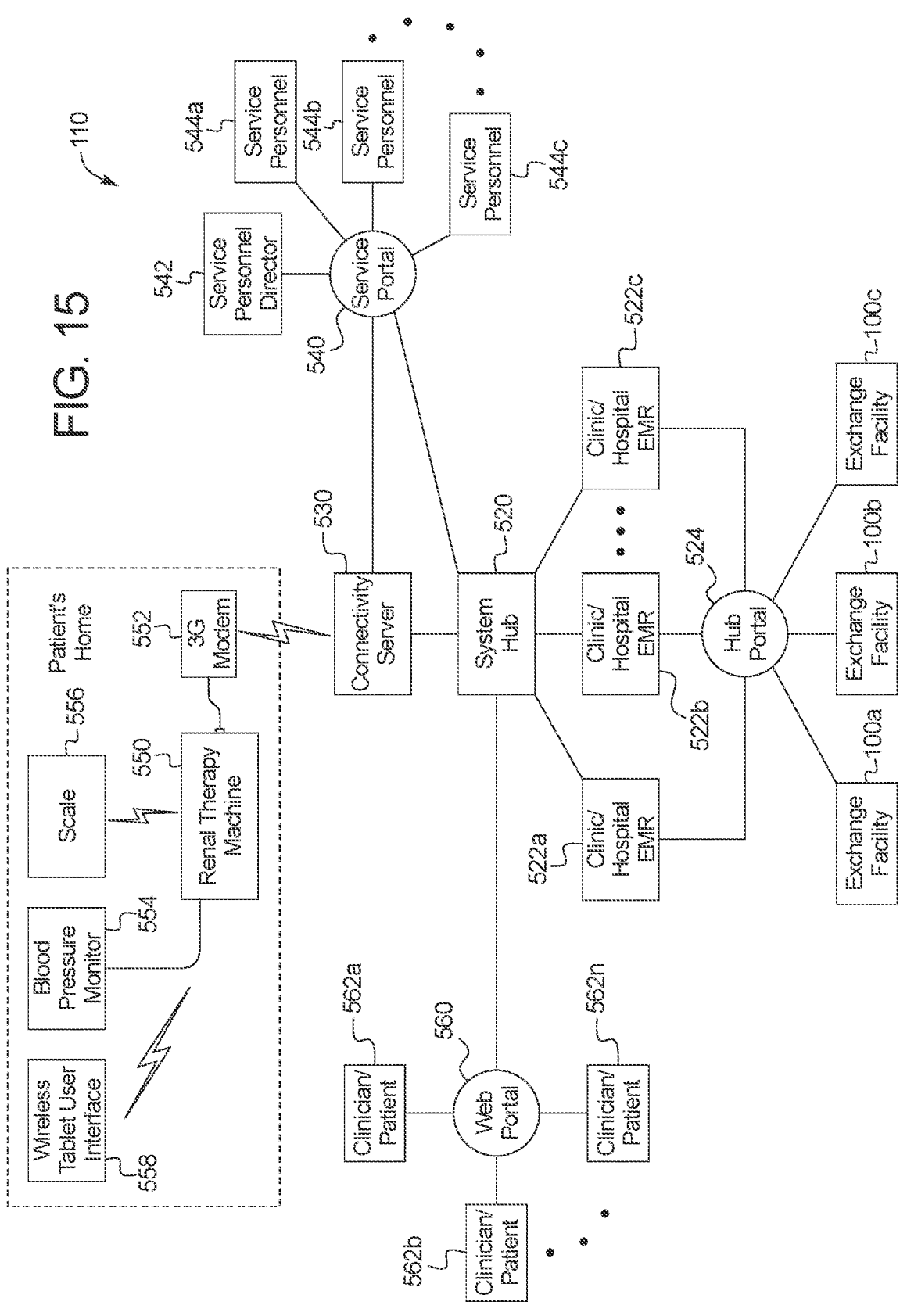
FIG. 15 is a schematic block diagram of another embodiment for a system according to the present disclosure.

The patient can wait for a dwell period and perform the above exchange again, and if desired do so multiple times. Or, the patient may do the single exchange and then leave facility 100. While in batch peritoneal dialysis treatment area 200, the patient can watch television, e.g., via television 118*a*, work on the patient's computer, read, or connect to the Internet via wireless transceiver 108. It is contemplated for the patient to weigh himself or herself at a weigh scale 130 and to take his or her blood pressure at blood pressure cuff 132, e.g., with the assistance of a facility professional 18. Either or both patient weight and blood pressure may be recorded before drain, and/or after drain, and/or after fill. The same recording can be done for glucose monitoring of the patient. The patient may record the readings and give them to the professional, the professional may record the readings, or the readings may be sent wirelessly from weigh scale 130 and/or pressure cuff 132 to treatment area computer 106*g* or to a front desk computer. All treatment data, such as patient weight, blood pressure, glucose level, drain amount(s) and fill amount(s), is recorded and logged. The patient data can be sent to the patient's clinic or hospital 522*a*, 522*b* or 522*c* (FIGS. 14 and 15). One clinician system for receiving and tracking peritoneal dialysis patient data is illustrated and described in U.S. patent application Ser. No. 13/828,900, entitled, "Home Medical Device Systems And Methods For Therapy Prescription And Tracking, Servicing And Inventory", filed, Mar. 14, 2013, the entire contents of which are incorporated herein by reference and relied upon.

It is contemplated that larger dialysis solution tanks 210*a*, 210*b*, 210*c* and 210*d* be tanks of sterilized fluid, e.g., rigid plastic or stainless steel tanks, which are removed through storeroom 150 via door 122 when the tanks are empty and replaced with a full tank 210 storing a dialysate of the same dextrose or glucose level from storeroom 150. The empty tanks 210 are shipped to the factory, sterilized for example using ethylene oxide while empty, and then are filled under a controlled and sterile manner with sterilized dialysis fluid of a desired dextrose or glucose level, after which the refilled tanks 210 can be shipped back to a facility 100. In an alternative embodiment, larger dialysis solution tanks 210a, 210b, 210c and 210d are left in place inside batch peritoneal dialysis treatment area 200, sterilized when emptied, e.g., via ethylene oxide, and then refilled onsite in a sterilized manner with sterilized dialysis fluid of a desired dextrose or glucose level. The tanks 210 inside storeroom 150 can therefore be even larger sterile tanks for refilling tanks 210a, 210b, 210c and 210d located within batch peritoneal dialysis treatment area 200.

It is also contemplated that a facility 100 can include an onsite sorbent system for regenerating effluent dialysate into useable dialysate. Such a sorbent system removes undesirable components in the effluent dialysate that have been obtained from the patient (e.g., toxins, fibrin and metabolic wastes). The sorbent system can also add desirable components (e.g., dextrose, glucose) and electrolytes (e.g., potassium, calcium) to reconstitute the dialysate and maintain a desired osmotic gradient for the removal of ultrafiltration from the patient. One known sorbent system uses a sorbent cartridge that absorbs uremic toxins such as urea, creatinine, uric acid and other metabolism by-products. As the effluent dialysate passes through the sorbent cartridge, undesirable components are removed from the dialysate and the dialysate emerges useable for additional treatment. Infusate is then pumped into the cleansed dialysate to add salts and/or sugars as needed. Suitable sorbent systems and corresponding methods are set forth in U.S. Pat. No. 7,208,092, entitled, "Systems and Methods for Peritoneal Dialysis"; U.S. Pat. No. 7,867,214, entitled, "Systems and Methods for Performing Peritoneal Dialysis"; and U.S. Pat. No. 7,922,686, entitled, "Systems and Methods for Performing Peritoneal Dialysis", the entire contents of each of which are incorporated herein by reference and relied upon.

The sorbent system can be installed at facility 100, so that a large batch of effluent dialysis fluid removed from multiple patients is regenerated at one time. Alternatively, the sorbent system is configured so that the effluent dialysate is regenerated immediately and individually as it is removed from each patient. Using a sorbent system to regenerate effluent dialysate collected by the facility 100 reduces the amount of fresh dialysate that needs to be shipped to and stored by facility 100. The use of such a sorbent system also reduces the amount of waste fluid that facility 100 needs to address and discard as has been discussed above.

Alternatively or in addition to sorbent regeneration, facility 100 can provide other forms of effluent cleaning for regeneration, such as any one or more of electrodialysis ("ED"), electrodialysis reversal ("EDR"), electrodeionization ("EDI"), ultrafiltration, reverse osmosis filtering, ultraviolet radiation, or ozone. Ozone can be created online by subjecting oxygen to ultraviolet light. The ozone can then be drawn into the effluent dialysate stream, e.g., via a venture pump. Ozone tends not to store well under positive pressure.

It is further contemplated that a facility 100 can include a water purification system to reuse at least a portion of the water separated from the effluent dialysate. Even if the effluent dialysate is not regenerated into useable dialysate, removing and purifying water from the effluent dialysate can reduce the volume of waste fluid requiring disposal. Additionally, the purified water can be used for other applications at facility 100, including the preparation of fresh dialysate made online or at the time of use. In addition to purifying water separated from effluent dialysate, the water purification system can be installed so as to receive tap water, purify the tap water, and use the purified tap water to prepare dialysate online using either fresh concentrates or in combination with the sorbent system described above. One suitable water purification system is set forth in U.S. Patent Publication No. 2011/0197971, entitled, "Water Purification System and Method", filed Apr. 25, 2011, the entire contents of which are incorporated herein by reference and relied upon. In one embodiment, the purification system includes filters to purify tap water (e.g., remove pathogens and ions such as chlorine) so that the water is preferably below 0.03 endotoxin units/ml ("EU/ml") and below 0.1 colony forming units/ml ("CFU/ml").

Referring again to FIG. 10, when the patient enters APD machine treatment area 300, the patient approaches desk 120b and hands an attendant an order received from one of the computers 106 at front desk 104. Or, the order is sent from one of the front desk computers 106a to 106f to treatment area 300 computer 106h. Further alternatively, facility professional 18 walks the patient from the front desk area to APD machine treatment area 300 and enters the patient's order, e.g., via the professional's mobile laptop computer, tablet or hybrid computer/tablet. In any case, the order is entered for billing purposes at this time, which again may include a co-pay amount at front desk 104. APD machine treatment stations 310a to 310j of APD machine treatment area 300 each use a disposable set 312 operable with an APD machine 330, which is illustrated in detail below in connection with FIG. 12. The facility professional pulls the disposable set 312 from behind treatment area desk 120b or enters storeroom 150 through door 124 to obtain disposable set 312. One suitable APD machine is the HomeChoice™ or HomeChoicePro™ machine provided by the assignee of the present disclosure.

If the patient in APD machine treatment area 300 is currently full of used dialysis fluid, the patient connects to one of common drain areas 250 via the patient's transfer set, which as before can be made with a sterilizing unit 244 and/or with a cleaning agent such as rubbing alcohol. The patient then drains the used fluid, e.g., in a sitting position, to allow for as complete a drain as possible. A drain can alternatively be done automatically, in which APD machine 330 pumps spent fluid from the patient to a drain bag provided as part of disposable set 312. After drain, the patient proceeds to (or is already at) a designated APD machine treatment station 310a to 310j for filling. Unlike with batch peritoneal dialysis treatment area 200, the disposable set 312 will be provided with a fill bag(s) having the patient's prescribed dextrose or glucose level dialysate and the prescribed fill volume. Thus, the particular APD machine treatment station 310a to 310j upon which the patient runs treatment may not be important as long as the machine can accept and operate the disposable cassette 312 given to the patient. There may be different versions of machines 330 at stations 310a to 310j, and the patient may prefer a particular version or machine 330 for programming or user interface reasons, for example. The patient connects his or her transfer set to disposable set 312 in a sterile manner, e.g., using a sterilizing unit 244 and/or with a cleaning agent such as rubbing alcohol. The patient can be allowed to load the disposable set 312 into the APD machine 330, program treatment, and execute treatment. In the alternative, one of the facility professionals may assist the patient with any one, or more, or all of loading the disposable set 312, programming treatment, and/or executing treatment. Once disposable set 312 is loaded into APD machine 330, the machine 330 then performs an automated peritoneal dialysis fill procedure, which is explained in more detail below.

As with the batch treatment, the patient in APD treatment area 300 can wait for a dwell period and perform the above exchange again, and if desired do so multiple times. Or, the patient may do the single exchange and then leave facility 100. While on a machine 330, the patient can watch television, e.g., via television 118*b*, work on the patient's computer, read, or connect to the Internet via wireless transceiver 108. As before, it is contemplated for the patient to weigh himself or herself at a weigh scale 130 and/or to take his or her blood pressure at blood pressure cuff 132, e.g., with the assistance of a facility professional 18. Either or both patient weight and blood pressure may be recorded before drain, and/or after drain, and/or after fill. The same recording can be done for glucose monitoring of the patient. All treatment data, such as patient weight, blood pressure, glucose level, drain amount(s) and fill amount(s) can again be recorded, logged and sent to the patient's clinic or hospital 22*a*, 22*b* or 22*c*.

Storeroom 150 includes spare APD machines 330 and disposable sets 312. Storeroom 150 also stocks spare disposable sets 412 for the stations 410*a* to 410*l* of continuous ambulatory peritoneal dialysis ("CAPD") treatment area 400 discussed next. And for any of the treatment areas 200, 300 and 400, storeroom 150 stocks spare sterilizing units 244, weight scales 130, blood pressure cuffs 132, glucose monitors (not illustrated) and other desired equipment. Suitable sterilizing units are described in U.S. patent application Ser. No. 11/773,623, entitled, "Peritoneal Dialysis Patient Connection System", filed Jul. 5, 2007, and U.S. patent application Ser. No. 11/773,824, entitled, "Peritoneal Dialysis Patient Connection System Using Ultraviolet Light Emitting Diodes", filed Jul. 5, 2007, the entire contents of each of which are incorporated herein by reference and relied upon.

When the patient instead enters CAPD treatment area 400, the patient approaches desk 120*c* and hands an attendant an order received from one of the computers 106 at front desk 104. Or, the order is sent from one of the front desk computers 106*a* to 106*f* to treatment area 400 computer 106*i*. Further alternatively, the facility professional walks the patient from the front desk area to APD machine treatment area 400 and enters the patient's order, e.g., via the professional's mobile laptop computer, tablet or hybrid computer/tablet. In any case, the order is entered for billing purposes at this time, which again may include a co-pay amount at front desk 104. CAPD treatment stations 410*a* to 410*l* of CAPD treatment area 400 each use a disposable set 412, which is operated manually by a patient. The facility professional pulls a disposable set 412 from behind treatment area desk 120*c* or enters storeroom 150 through door 124 to obtain disposable set 412.

If the patient in CAPD treatment area 400 is currently full of used dialysis fluid, the patient can connect to one of common drain areas 250 via the patient's transfer set, which as before can be made with a sterilizing unit 244 and/or with a cleaning agent such as rubbing alcohol. A drain can alternatively be done manually, in which the patient gravity feeds spent fluid from the patient to a drain bag provided as part of disposable set 412. The patient then drains the used fluid, e.g., in a sitting position, to allow for as complete a drain as possible. After drain, the patient proceeds to (or is already at) a designated CAPD treatment station 410*a* to 410*l* for filling. Unlike with batch peritoneal dialysis treatment area 200, the disposable set 412, like disposable set 312, will be provided with a fill bag(s) having the patient's prescribed dextrose or glucose level dialysate and the prescribed fill volume. Thus, the particular CAPD treatment station 410*a* to 410*l* at which the patient runs treatment is not important. The patient likely connects himself or herself to disposable set 412 for treatment. In the alternative, one of the facility professionals may assist the patient with connecting to disposable set 412. The patient connects his or her transfer set to disposable set 412 in a sterile manner, e.g., using a sterilizing unit 244 and/or with a cleaning agent such as rubbing alcohol. The patient then performs a manual peritoneal dialysis fill procedure, which is explained in more detail below.

As an alternative to storing dialysate with predetermined levels of glucose and dextrose, a proportioned solution may be produced on demand at the facility. In one embodiment, facility 100 can include separate containers of fresh dialysate, water and other concentrates or solutions containing desirable components in liquid form, such as glucose, dextrose and electrolytes. Alternatively, the use of dry chemicals or concentrated chemical reagents as an alternative to liquid concentrates can be used and reduce the space necessary for storing the concentrates. Facility 100 mixes the dialysate, water, salt, concentrates and/or other chemicals and solutions on demand based on each patient's prescription. For example, one method of producing fresh dialysate is by mixing an acid concentrate with a bicarbonate concentrate and then diluting the resulting mixture with water. In this example, the acid concentrates can be stored in separate ionic concentrations, and the bicarbonate concentrates can be stored as sodium bicarbonate and/or sodium bicarbonate mixed with sodium chloride. The concentrates can then be mixed onsite to prepare fresh dialysate according to a patient's specific prescription. Mixing the dialysate onsite allows facility 100 to reduce the amount of disposable packaging that is consumed via the use of premixed dialysates. Instead, dialysate can be prepared as needed using larger containers of concentrate liquids and/or chemicals for preparing dialysate online. One suitable system and method for mixing peritoneal dialysis solutions is set forth in U.S. Pat. No. 5,925,011, entitled, "System and Method for Providing Sterile Fluids for Admixed Solutions in Automated Peritoneal Dialysis", the entire contents of which are incorporated herein by reference and relied upon. The mixed dialysate solution can be provided to the patient, for example by dispensing the liquid into a heating/weighing bag provided to the patient for dialysis treatment.

As with the treatments of areas 200 and 300, the patient in CAPD treatment area 400 can wait for a dwell period and perform the above exchange again, and if desired do so multiple times. Or, the patient may do the single exchange and then leave facility 100. While at a treatment station 410*a* to 410*l*, the patient can watch television, e.g., via television 118*c*, work on the patient's computer, read, or connect to the Internet via wireless transceiver 108. As before, it is contemplated for the patient to weigh himself or herself at a weigh scale 130 and to take his or her blood pressure at blood pressure cuff 132, e.g., with the assistance of a facility professional 18. Either or both patient weight and blood pressure may be recorded before drain, and/or after drain, and/or after fill. The same can be done for glucose monitoring of the patient. All treatment data, such as patient weight, blood pressure, glucose level, drain amount(s) and fill amount(s) can again be recorded and logged and sent to the patient's clinic or hospital 22*a*, 22*b* or 22*c*.

Facility Treatment Areas

Referring now to FIG. 11, one embodiment for batch peritoneal dialysis treatment area 200 discussed above is illustrated. Batch peritoneal dialysis treatment area 200 dispenses specific amounts of a prescribed type of dialysis solution. Batch peritoneal dialysis treatment area 200 can be a portion of a treatment facility 100 discussed above and includes larger dialysis solution tanks 210*a*, 210*b*, 210*c* . . . 210*n*, which are multi-treatment containers of different, select peritoneal dialysis solutions, such as ones having the glucose or dextrose levels listed above. For example, each tank 210a, 210b and 210c can contain a different dialysis solution 212a, 212b and 212c, e.g., having a different dextrose level, e.g., 1.5%, 2.5% and 4.25% dextrose or glucose level, e.g., 1.36%, 2.27% and 3.86% glucose, which are known and approved levels.

Tanks 210a to 210c can be stainless steel or plastic and in an embodiment are capable of being sterilized, e.g., via ethylene oxide sterilization. Tanks 210a to 210c can have integrated castors for transport or can be tilted for loading onto and off of a rolling pallet or forklift for transport. Tanks 210a to 210c in the illustrated embodiment are each provided with a heater 214, such as a radiant infrared or ultraviolet heater that connects to a glass or other radiant wave permeable window or section of the tank. Heater 214 can alternatively be a resistance heater (not illustrated) upon which the tank sits. In either case, heater 214 receives power or duty cycle signals from a control unit 215. Control unit 215 can for example be a microcontroller (e.g., contain processing and memory) located in a box with heater 214. A temperature sensor 216, such as a thermocouple or thermistor, is placed inside each tank 210a to 210c and detects and feeds a temperature signal to the microcontroller for temperature, e.g., duty cycle, control of the dialysis fluid. The microcontroller can be connected to a wireless modem that links wirelessly via transceiver 108 to batch area computer 106g and/or one of front desk computers 106a to 106f.

There may also be an analog output liquid level sensor 218, such as an ultrasonic or laser sensor provided at the top of the tank, which detects and sends a signal indicative of a level of dialysate inside tanks 210a to 210c to the microcontroller housed inside the enclosure for heater 214. Liquid level or volume can be ascertained alternatively by providing a weigh scale (not illustrated) beneath each tank 210a to 210c. The weigh scale can itself send a wireless weight signal to batch area computer 106g and/or one of front desk computers 106a to 106f in one embodiment. In these embodiments, the dialysate temperature and level (or volume) within each tank 210a to 210c can be monitored remotely. Software at the remote computer can also be provided to inform the facility professional of when a tank 210a to 210c will soon need to be switched out or refilled.

It is also contemplated to make tanks 210a to 210c out of a semi-translucent material, such as a semi-translucent plastic, so that the dialysis fluid level within the tank can be viewed from outside of the tank. Also, each tank 210a to 210c can be provided with a hydrophobic or high-efficiency particulate air ("HEPA") filter 219, e.g., at the top of the tank, to let filtered air into the tank to displace consumed dialysate, so that negative pressure does not build within the tank.

In the illustrated embodiment, each tank 210a to 210c is provided with a plurality of peritoneal dialysis supply dispensers, e.g., dispensers 220a to 220f. Dispensers 220a to 220f may be attached, e.g., foldably attached, to tank 210a to 210c. In this manner, dispensers travel with the tanks for sterilization, testing and repair. Alternatively, dispensers 220a to 220f are shipped to facility 100 individually in sterilized bags (not illustrated), stored in storeroom 150, removed from the sterilized bag and connected when needed to one of the tanks 210a to 210c in a sterile manner, e.g., using a sterilizing unit 244 and/or a sterilization cleaning agent such as alcohol.

Dispenser 220a of tank 210a illustrates one embodiment for the dispensers in detail. Dispenser 220a includes a supply line 222, a pressure regulator 224 that controls downstream pressure, a metering device fill valve 226, a metering device 228, a metering device dispel valve 232, and a flexible line 234 leading flexibly to a check valve 236 and a dispenser connector 238. Dialysis fluid in tanks 210a to 210c is gravity fed to the patient. The large amount of dialysis fluid held within the tanks can create a large head pressure. Pressure regulator 224 causes the pressure of the dialysis fluid downstream of the regulator to be within a more manageable range, e.g., five to ten psig.

Metering device 228 includes liquid level sensors 230a and 230b, which can operate as an emitting and receiving pair, e.g., light or laser emitting and receiving. Liquid level sensors 230a and 230b are moved up and down along the scale of metering device 228 by patient 16 or facility professional 18 to the prescribed fill level. Although not illustrated, a ball screw type of translating apparatus can be provided with metering device 228, which translates liquid level sensors 230a and 230b in a precise manner via a manual or motorized turning of the screw to the prescribed fill level. To fill metering device 228, dispel valve 232 is closed, while fill valve 226 is opened, so that liquid under a manageable pressure and corresponding flowrate fills the metering tube.

Control unit 215 is programmed such that when the dialysis fluid fills the metering tube so that its level obstructs the beam of light or energy running from liquid level sensor 230a to sensor 230b, fill valve 226 is closed. Valves 226 and 232 and liquid level sensors 230a and 230b are controlled electrically via the tank's control unit 215 in the illustrated embodiment. It is also contemplated to place a filtered air port (not illustrated), like filters 219, at the top of metering device 228, so that pressure does not build within the tube of metering device 228 and so that any air entering supply line 222 from tank 210a and 210c is purged under pressure to the top of or out though the top of metering device 228.

To fill the patient from metering device 228, fill valve 226 remains closed, while dispel valve 232 is opened. Fluid is gravity fed under a safe low pressure through dispel valve 232, flexible line 234, check valve 236 and connector 238, through the patient's transfer set 242 and into patient 16 via the patient's indwelling, implanted catheter. Prior to fluid delivery, the patient makes a sterile connection of the patient's transfer set 242 to dispenser connector 238, e.g., via a sterilization unit 244 and/or an antiseptic cleaning agent, such as rubbing alcohol. Check valve 236 prevents any patient fluid from moving into supply line 222. Also, supply line 222 remains fully primed between uses. Dispenser connector 238 is configured such that no fluid can exit supply line 222 through check valve 236 unless patient transfer set 242 is mated to dispenser connector 238. To this end, dispenser connector 238 may be provided with an on/off valve (not illustrated). Dispenser connector 238 may also have a disposable tip (not illustrated) that is replaced with a sterilized tip prior to each use.

Metering device 228 can alternatively include other apparatuses capable of monitoring and metering the flow of dialysis solution to meet the amount of dialysis solution 212a to 212c predetermined by the patient's prescription. In one alternative embodiment, metering device 228 includes an integrated flowmeter that monitors and integrates dialysate flowrate versus time to determine when the patient has received the prescribed amount of dialysis solution.

In another alternative embodiment, metering device 228 includes a balance chamber that has a known and fixed volume chamber, which is divided by a membrane or diaphragm that flaps back and forth between inner walls of the chamber separated by the membrane or diaphragm.

Pressurized dialysate flowing from tanks 210a to 210c is split into two inlet lines, each leading to different sides of the membrane. Each inlet line is valved. The valves are sequenced to drive dialysate into the chamber from alternating sides of the membrane, each time driving a like volume of dialysate out of the chamber on the other side of the membrane towards the patient. Thus there are also two outlet lines, one on each side of the membrane or diaphragm, leading from the chamber towards the patient, each outlet line also being valved, wherein the valves of the outlet lines are sequenced in sync with the valves of the inlet lines, and wherein the inlet valve on one side of the membrane is opened and closed with the outlet valve on the other side of the membrane and vice-versa. The valved outlet lines are teed together to form a single outlet line forming or leading to flexible line 234, check valve 236, connector 238 and patient 16. Control unit 215 counts or knows how many times the valves are sequenced. That number multiplied by the known volume of the chamber provides an ever-increasing total volume pumped to the patient. When the actual total volume pumped equals the prescribed total volume, the exchange fill is completed and the balance chamber valves are closed. Here, the prescribed total volume can be entered electronically into control unit 215 of tanks 210a to 210c via (i) a user interface or keypad provided with dispensers 220a to 220f or (ii) the computer, tablet, or hybrid computer/tablet of one of the facility professionals, which is in wireless communication with control unit 215.

In many instances, patient 16 will enter batch peritoneal dialysis treatment area 200 with used dialysis solution in his or her peritoneum that first needs to be drained. To do so, patient 16 can connect first to (i) a drain bag (not illustrated), which can then be weighed and/or sampled and then discarded or (ii) an individual drain (not illustrated). In the illustrated embodiment, however, patient 16 can instead drain to a common drain area 250 discussed above in connection with FIG. 10. Common drain area 250 includes a tank or basin 252. A plurality of valved drain line assemblies 254a to 254g extend off of tank or basin 252. Each valved drain line assembly 254a to 254g includes a three-way valve 256 that allows the drain fluid to flow either from patient 16 to a reusable weigh bag or container 258 or from weigh bag or container 258 to tank or basin 252. In an embodiment, no position of valve 256 allows fluid to flow from patient 16 to drain tank or basin 252, which forces the patient to drain to weigh bag or container 258. The patient connects to valve 256 via sterilization unit 244 and/or via an antiseptic agent as has been discussed above.

As illustrated, each weigh bag or container 258 sits on a scale 260. Scale 260 can send the patient's drain weight wirelessly via transceiver 108 to a computer 106a to 106g, which then logs the drain volume along with other exchange data discussed above for sending to the patient's clinic 22a to 22c. The effluent weight data transfer to a computer 106a to 106g is done alternatively manually as has been discussed herein. In an embodiment, weigh bag or container 258 is provided with a sample port (not illustrated), which allows an effluent sample to be taken, which can be given to a facility professional 18, e.g., at batch area desk 120a or front desk 104 for analysis that can be performed while patient 16 is performing his or her exchange. The results can be given to the patient upon leaving facility 100 and/or logged as part of the exchange data sent to the patient's clinic 22a to 22c. Although weighing the drained dialysate to track the patient's drain volume is desired for patient volume and ultrafiltration control, it is contemplated that not every facility 100 will have the means or resources for weighing drained dialysate. In such cases, a patient can instead drain effluent dialysate into a common drain without such weighing.

After the patient's drain to weigh bag or container 258 is complete, it is contemplated that the patient or facility professional 18 lift the bag or container 258 to, e.g., a hook or ledge provided by tank or basin 252, located elevationally above both valve 256 and the connection of the respective drain line 254a to 254g to the tank or basin. The position of valve 256 is then switched so that the patient's effluent can gravity flow from weigh bag or container 258 to tank or basin 252. Tank or basin 252 is configured and arranged to efficiently and effectively handle biowaste, such as used dialysate from the patient's peritoneum.

Figure 12:
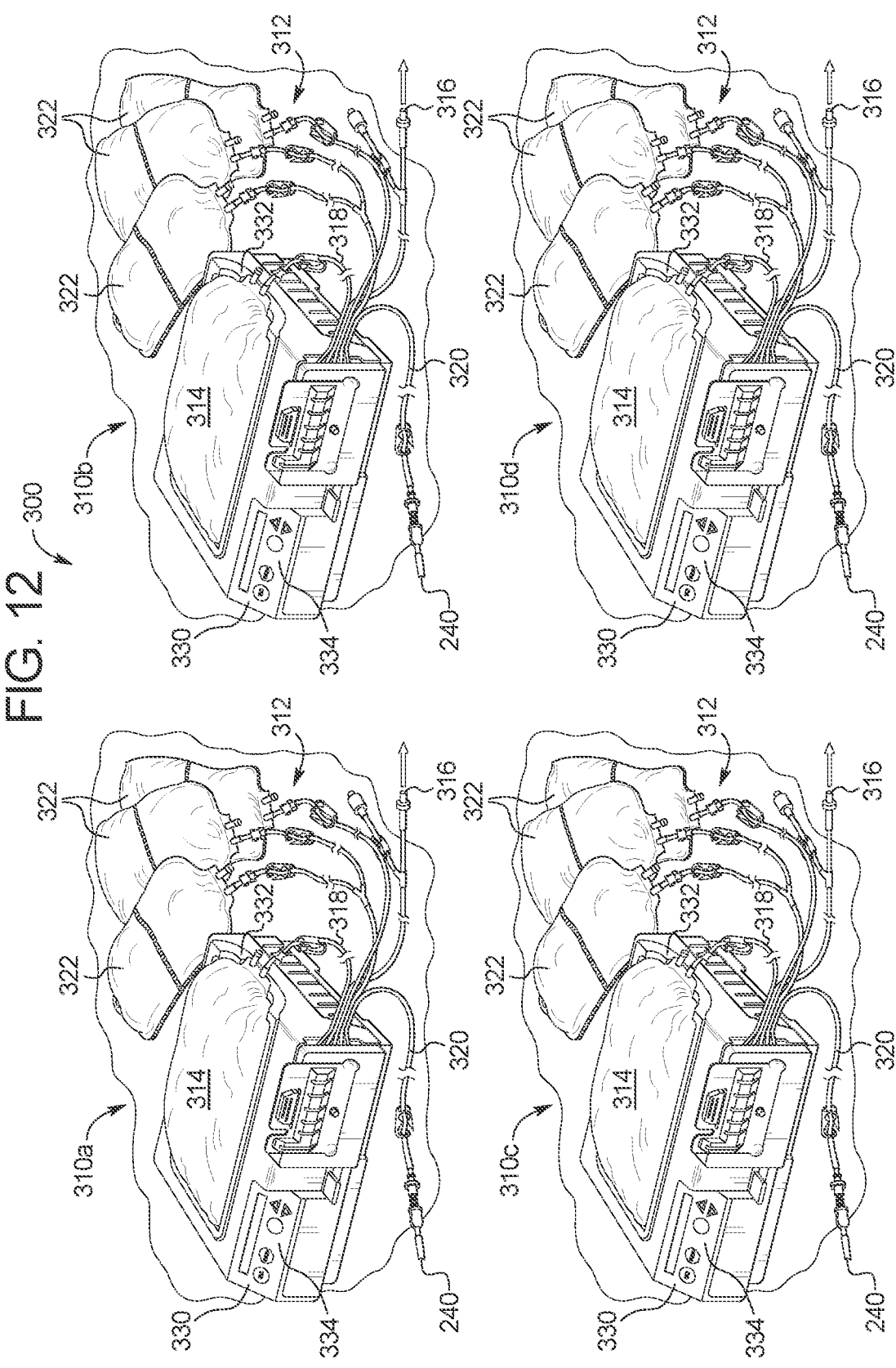
FIG. 12 is a plan view of one embodiment for an automated peritoneal dialysis ("APD") machine treatment area of a peritoneal dialysis exchange facility according to the present disclosure.

Referring now to FIG. 12, one embodiment for an APD machine peritoneal dialysis treatment area 300 discussed above is illustrated. APD machine peritoneal dialysis treatment area 300 dispenses specific amounts of a prescribed type of dialysis solution and can be a portion of a treatment facility 100 as discussed above. Treatment area 300 includes APD machine treatment stations 310a to 310d, which each provide a disposable set 312 operable with an APD machine 330. Each disposable set 312 can contain a different dialysis solution, e.g., having a different dextrose level, e.g., 1.5%, 2.5% and 4.25% dextrose or glucose level, e.g., 1.36%, 2.27% and 3.86% glucose, which are known and approved levels. Each disposable set 312 can also contain a specified volume of the prescribed type of dialysate. Or, disposable set 312 can contain more dialysate than the prescribed volume and rely on APD machine 330 to pump the prescribed volume of dialysate to patient 16.

Disposable set 312 may contain a single dialysate fill bag 314 only. Here, the patient can drain to a common drain area 250 as has been discussed above in connection with FIGS. 10 and 11, including all alternatives discussed in connection with those figures. When the patient drains to common drain area 250, disposable set 312 does not need a drain bag or associated drain line or tube. Alternatively, disposable set 312 does include a drain bag that attaches to a drain line 316, allowing APD machine 330 to perform the drain automatically for the patient. Still further alternatively, APD machine 330 pumps patient effluent to an individual drain via drain line 316.

In the illustrated embodiment, dialysate fill bag 314 is placed on a heater 332 located at the top of APD machine 330. Heater 332 heats the dialysate within fill bag 314 to at or near the patient's body temperature, e.g., about 37° C. It is expressly contemplated however to preheat fill bag 314 as part of disposable set 312 stored in storeroom 150 to reduce or even eliminate heating time before the patient's fill can begin. A tube 318 carries heated dialysate pumped from fill bag 314 into and by a disposable pumping cassette that has been loaded into APD machine 330 and thus cannot be viewed in FIG. 12. One suitable disposable pumping cassette is illustrated and described in U.S. Pat. No. 5,989,423, the entire contents of which are incorporated herein by reference and relied upon. APD machine 330 then pumps heated dialysate out of the cassette, through patient line 320, to patient 16. APD machine 330 via the disposable pumping cassette can pump a precise fill volume of the prescribed dialysate to the patient's peritoneum. The prescribed volume is entered into the control unit (not illustrated but including processing and memory) of APD machine 330 by the patient or facility professional 18 manually in one embodiment via a user interface 334. Alternatively, the facility professional enters the prescribed fill volume into the control unit (processing and memory) of APD machine 330 remotely and wirelessly via the facility professional's laptop computer, tablet or hybrid computer/tablet.

For a single exchange, once the prescribed fill from fill bag 314 is pumped to patient 16, the patient can disconnect from machine 330 and leave facility 100. For multiple fills, the patient can remain connected to machine 330 or disconnect from machine 330 but remain physically close to (e.g., within one-half hour of) machine 330, while the solution from fill bag 314 dwells within the patient's peritoneum, removing toxins and ultrafiltrate ("UF"). Once a prescribed dwell period has ended, machine 330 automatically pulls the used effluent dialysate from the patient into and by the disposable pumping cassette, which in turn pumps the effluent dialysate to drain via drain line 316.

Disposable set 312 may accordingly include one or more additional supply bags 322 to allow the drain and fill procedure to be repeated one or more time. Machine 330 records all fill volumes and drain volumes for logging and delivery to the patient's clinic 22a to 22c via any data flow manner described herein. One or more additional supply bag 322 can contain a different type of dialysate than initial fill bag 314. For example a last fill supply bag 322 may contain a dialysate prescribed for remaining in the patient's peritoneum after the patient has left facility 100.

Figure 13:
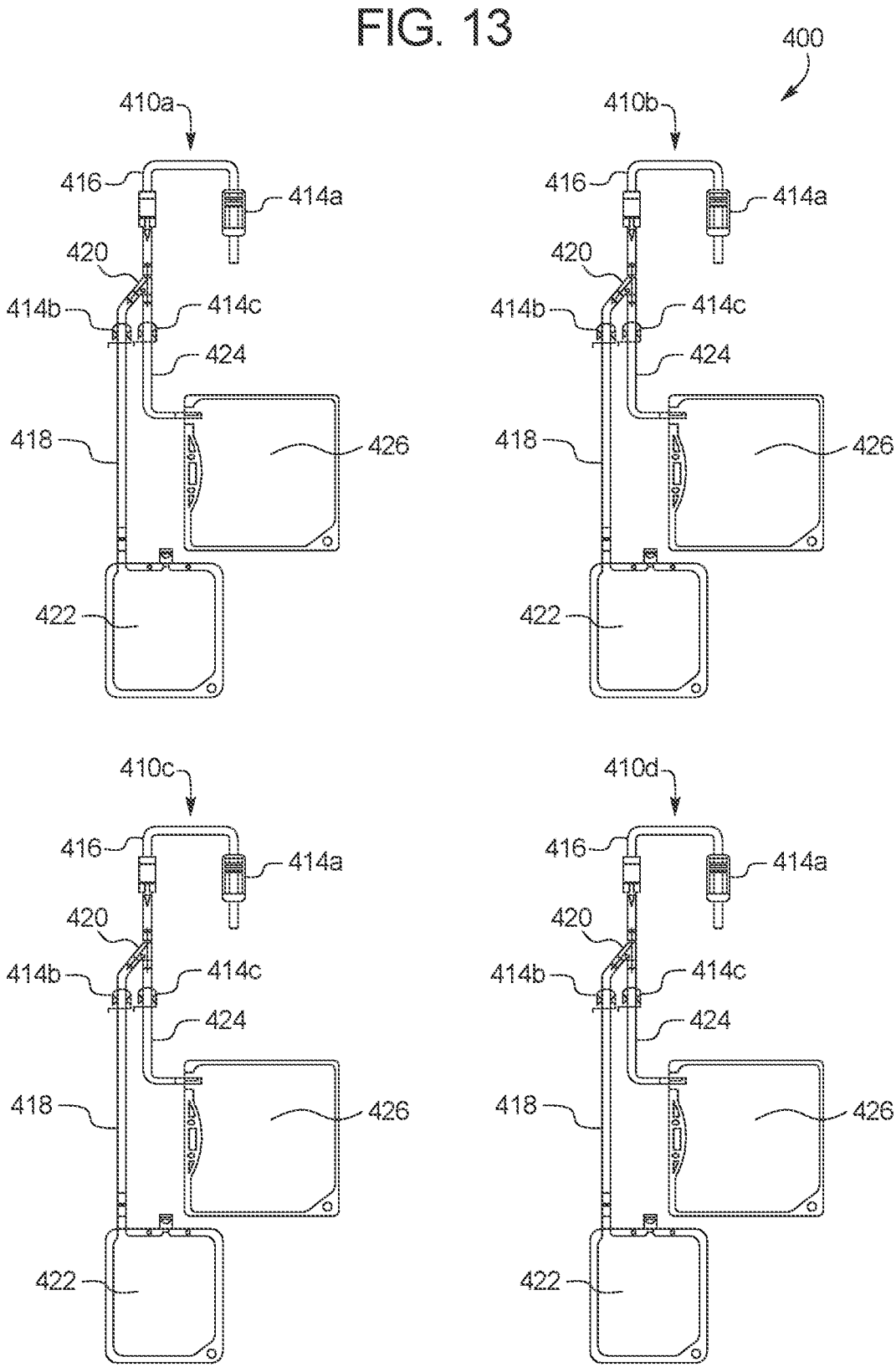
FIG. 13 is a plan view of one embodiment for a continuous ambulatory peritoneal dialysis ("CAPD") machine treatment area of a peritoneal dialysis exchange facility according to the present disclosure.

Referring now to FIG. 13, one embodiment for a CAPD peritoneal dialysis treatment area 400 discussed above is illustrated. CAPD peritoneal dialysis treatment area 400 likewise dispenses specific amounts of a prescribed type of dialysis solution and can be a portion of a treatment facility 100 as discussed above. Treatment area 400 includes CAPD treatment stations 410a to 410d, which each provide a disposable set 412 that is operated manually by the patient typically. Each disposable set 412 can contain a different dialysis solution, e.g., having a different dextrose level, e.g., 1.5%, 2.5% and 4.25% dextrose or glucose level, e.g., 1.36%, 2.27% and 3.86% glucose, which are known and approved levels. Each disposable set 412 can also contain a specified volume of the prescribed type of dialysate. Or, disposable set 412 can contain more dialysate than the prescribed volume and rely on the patient to meter the prescribed fill volume of dialysate.

Disposable set 412 in the illustrated embodiment is a twin-bag CAPD set, which uses three clamps 414a, 414b and 414c to perform the CAPD treatment. Clamp 414a is mounted to a first tube 416, which connects to the patient's transfer set 242 (FIG. 11), which in turn runs to a catheter implanted in the body of a patient. Clamp 414b is mounted to a second tube 418, which is connected at one end to a Y-shaped joint 420 joined to the other end of first tube 416. Second tube 418 is connected at its other end to a dialysis fluid bag or container 422 for supplying the prescribed amount and type of dialysate to the patient. Clamp 414b is mounted to a third tube 424 connected at one end to a drain bag 426 for collecting and discarding the patient's used effluent dialysate.

When the patient is initially full of spent effluent, the patient opens valves 414a and 414c to gravity drain to drain bag 426. To flush the system of drain fluid, the patient then opens valves 414b and 414c to allow a small amount of fresh fluid to gravity flow to drain, flushing and priming second tube 418. The patient then refills with fresh dialysate by opening valves 414a and 414b to allow fresh fluid to gravity feed to the patient. Disposable set 412 can alternatively replace separate valves 414a to 414c with a single multi-position valve that connects to Y-shaped joint 420 and provides multiple manually set positions to perform each of the draining, flushing and filling steps.

Multiple disposable sets 412 may be provided to the patient for multiple exchanges. In any case, the patient can alternatively drain to a common drain area 250 or to an individual house drain as has been discussed above in connection with FIGS. 10 and 11, including all alternatives discussed in connection with those figures. When the patient drains to common drain area 250 or house drain, disposable set 412 needs only a single line 416 connected at a patient end to valve 414a and at the other end to solution bag 422. Single line 416 can be packaged pre-primed up to valve 414a, eliminating the flushing step. As with APD set 312, solution bag 422 of CAPD set 412 can be pre-warmed to at or near the patient's body temperature, e.g., about 37° C. in storeroom 150 to reduce or even eliminate heating time before the patient fill can begin.

For a single exchange, once the prescribed fill from fill bag 422 is gravity fed to patient 16, the patient can disconnect from set 412 and leave facility 100. For multiple fills, the patient can remain physically close to (e.g., within one-half hour of) facility 100, while the solution from fill bag 422 dwells within the patient's peritoneum, removing toxins and ultrafiltrate ("UF"). Once a prescribed dwell period has ended, the patient drains to drain bag 426 using a second disposable set 412, to community drain 250 or to another house drain as discussed above, and performs another fill with a second supply bag 422.

Facility 100 records all fill volumes and drain volumes for logging and delivery to the patient's clinic 22a to 22c via any data flow manner described herein. One or more additional supply bag 422 can contain a different type of dialysate than the initial fill bag 422. For example a last fill supply bag 422 may contain a dialysate prescribed for remaining in the patient's peritoneum after the patient has left facility 100.

Facility System Architecture

FIGS. 14 and 15 illustrate various embodiments for integrating the facilities described above into a larger system. Also illustrated are various methods for operating the facilities of the present disclosure. In FIG. 14, peritoneal dialysis system 10 includes peritoneal dialysis exchange facilities 100a, 100b and 100c, which can access electronic medical record databases 522a, 522b and 522c via system hub 520 and web portal 560. In FIG. 12, peritoneal dialysis system 110 includes peritoneal dialysis exchange facilities 100a, 100b and 100c, which can access electronic medical record databases 522a, 522b and 522c via web portal 524. The primary difference between the two systems is that in system 10 of FIG. 14, web portal 560 accessed via dialysis exchange facilities 100a, 100b and 100c is provided by the same entity that provides and supports the patient's home machine, e.g., the machine, solution and disposable supplier ("machine supplier"). Here, facilities 100a, 100b and 100c may be primarily owned and operated by the machine supplier. In system 110 of FIG. 15, on the other hand, web portal 524 is hosted by a different entity, e.g., by one of the clinics that work with the machine supplier. There may be more than one different entity or clinic operating with system 110, each entity hosting their own web portal 524. For example, Clinic A, working with the machine supplier may service one portion of a country in which the machine supplier operates, while Clinic B, working with the machine supplier services another portion of the country, and so on. Here, facilities 100a, 100b and 100c may be primarily owned and operated by the clinics or companies other than the machine supplier.

In systems 10 and 110, exchange facilities 100a, 100b and 100c are walk-in facilities in which a peritoneal dialysis patient can receive peritoneal dialysis treatment at the location. Each facility 100 in an embodiment receives a prescription from a patient and verifies that the patient has been prescribed a peritoneal dialysis treatment by a licensed physician. In one embodiment, a repeat patient can be stored in the computers of the facility, such that the patient can identify himself or herself, be accessed from a database, and perform treatment without having to bring his or her prescription to the facility. The patient's prescription sets forth a plurality of treatment parameters, such as type of treatment (e.g., APD versus CAPD), number of exchanges per treatment, and volume and type of solution for each exchange. Different dialysis solutions contain different compositions of dextrose or glucose, salt and other constituents. Glucose or dextrose controls the osmotic gradient provided by the dialysate, which in turn controls how much or how quickly excess fluid is pulled from the patient's body and into the peritoneum as ultrafiltrate ("UF"). The higher the dextrose level, the higher the UF ability of the solution, but also the higher the caloric intake of the solution. Patients may need more or less glucose or dextrose for longer dwell time exchanges, such as for midday exchanges. Electrolytes such as potassium and calcium are also often included in dialysis solutions in similar concentrations as in healthy blood. The composition of a dialysis solution, and the amount of dialysis solution used per exchange, are therefore prescribed by a licensed physician to best treat each individual patient.

The present disclosure envisions various apparatuses and methodologies for receiving and verifying a patient's prescription. In the embodiments discussed herein, a patient can present an exchange facility 100 (referring generally to each facility 100a, 100b, 100c . . . 100n, or collectively to all facilities) with a paper prescription or an electronic file or data storage device (e.g., flash drive) that has been provided to the patient by a licensed physician from an outside hospital or clinic. Facility 100 via web portal 560 (FIG. 14) or 524 (FIG. 15) can then verify the prescription by the accessing electronic medical record ("EMR") databases 522a, 522b and/or 522c through the web portal. Doctor or clinician databases 522a, 522b and 522c store data relating to each patient's current dialysis prescription and may additionally keep historical information, such as past treatment data and past treatment prescriptions, none, some or all of which may be accessible via facilities 100. Thus, databases 522a, 522b and 522c may simply look (manually or automatically) at the patient's prescription for a match with one or more current prescriptions and communicate back to facility 100 whether or not a match has been found. Or, databases 522a, 522b and 522c may display the patient's approved prescription(s) to the professional at facility 100 for verification.

Databases 522a, 522b and 522c may additionally allow the facility professional 18 to access treatment data specific for the patient. For example, the patient may have multiple approved prescriptions and the freedom to pick any prescription to use on a given day. Patient data may indicate that one prescription may be working better than one or more other prescription. The facility professional 18 may be trained to look at the data and recommend one or more of the patient's better performing treatments for that day.

It is also contemplated to not require the patient to have to bring the patient's prescription to facility 100. Instead, patient name and/or patient identification is/are entered at facility 100, which communicates over web portal 524 or 560 with a database 522a, 522b and 522c, which in turn communicates back the patient's currently approved prescription(s) if it exists. Here, verification exists but no matching is required.

If the patient cannot be found on a database 522a, 522b or 522c, it is contemplated to let the facility professional 18 contact the patient's doctor or clinician to gain authorization to let the patient perform an exchange. And as discussed above, certain countries or areas of countries may not have the ability to link to a system for verification. It is accordingly contemplated to allow the prescription brought on paper or electronically to be self-authenticating, so that an exchange may take place as long as the prescription appears to be legitimate. Here again, when a patient visits a facility 100 for the first time, the patient and his/her current prescription can be entered into the local facility 100 computers to enable verification to be performed the next time the patient returns to facility 100. If the patient's prescription is changed, the change can be noted on the computers of local facility 100.

As discussed in detail below, after the prescription is verified according to any of the embodiments discussed above, or is taken as self-authenticating, the prescription is used to determine the volume and type of dialysis solution that the patient needs for the present treatment. The prescription also indicates whether the dialysis solution is to be delivered to the patient via a machine or is to be delivered manually. Knowing this information, the patient can proceed to the next step towards obtaining treatment.

In the illustrated embodiments, system hub 520 is connected to a connectivity server 530, a service portal 540 and web portals 560 and/or 524. System hub 520 communicates with the patients' home peritoneal dialysis or APD machines 550 through connectivity server 530 to download new treatment prescriptions to home machines 550 and to receive current treatment data from the home APD machines 550. In the illustrated embodiment, machine 550 is a hub for peritoneal dialysis peripherals at the patient's home (indicated by the dotted lines in FIGS. 14 and 15), which can include for example: a modem 552, a blood pressure monitor 554, a scale 556, and a user interface, such as a wireless tablet user interface 558. The modem 552, blood pressure monitor 554, scale 556 and tablet 558 may communicate wirelessly with home APD machine 550, or in the alternative may be wired to home machine 550.

Modem 552 can be a 3G, 4G, 5G or other type of Internet modem for enabling communication between home machines 550 and system hub 520. Blood pressure monitor 554 and scale 556 enable patient blood pressure and weight to be taken and recorded. Likewise, blood pressure monitor 554 may be a pneumatically controlled blood pressure cuff that is pressurized around the patient's arm. Blood pressure monitor 554 can send blood pressure data to the control processer of home machine 550, or the patient can measure his or her own blood pressure and enter that data into tablet 558, which in turn communicates the blood pressure data with the control processor of home machine 550. The control processor of home APD machine 550 can use weight data from scale 556, for example, to calculate how much ultrafiltration has been removed from the patient after a treatment. Treatment data is stored and later transferred via modem 552 to an electronic medical records database 522a to 522c to use in evaluating a current treatment prescription and for determining new prescriptions.

Besides storing weight and blood pressure data, each home peritoneal dialysis treatment performed by a patient using home machine 550 results in the storage of data relating to the parameters and activities of home machine 550 and the patient over the course of the treatment. Machine 550 can store, for example, dialysis fluid flowrates, and the total amount of ultrafiltrate removed over treatment. Errors, alerts, alarm conditions and whether or not treatment steps have been successfully performed can also be recorded. Treatment data is then sent from home machine 550 via modem 552 to system hub 520 via connectivity server 530, where it is stored in the hospital or clinician databases 522*a*, 522*b* or 522*c*, which can then be accessed by facilities 100*a*, 100*b* or 100*c* as discussed above.

Doctor and clinician databases 522*a*, 522*b* and 522*c* contain patient-specific treatment and prescription data and therefore access to the databases can be highly restricted. In each of the embodiments shown in FIGS. 14 and 15, facilities 100*a*, 100*b* and 100*c* may be able to gain some level of access to doctor or clinician databases 522*a*, 522*b* and 522*c* through a web portal. In FIG. 14, facilities 100*a*, 100*b* and 100*c* along with patients and clinicians 562*a*, 562*b* and 562*c*, e.g., from their home computers, each access web portal 560 hosted by the machine supplier. The doctors/ clinicians will have access to data that cannot be obtained by the patients or the public at large however. Facilities 100*a*, 100*b* and 100*c* may have the doctors/clinician level of access, the public at large level of access or some level of access in between. In FIG. 15, the same level of access to the patient databases provided by the machine supplier portal 560 in FIG. 14 may be afforded to facilities 100*a*, 100*b* and 100*c* via doctor/clinician Internet portal 524. Again in FIG. 15, doctor/clinician portal 524 and facilities 100*a*, 100*b* and 100*c* are managed and/or owned by a clinic or hospital. In FIG. 14, portal 560 and facilities 100*a*, 100*b* and 100*c* are managed and/or owned instead by the machine supplier.

Referring again to both FIGS. 14 and 15, system hub 520 and connectivity server 530 are also connected to service portal 540. Connectivity server 530 allows a service personnel director 542 and service personnel 544*a*, 544*b* and 544*c* to track and retrieve various assets across the network using home machine 550 and/or modem serial numbers. The assets may include APD machines and/or other equipment located inside facilities 100*a*, 100*b* and 100*c*. The connectivity server 530 can also be used to receive and provide firmware upgrades to the APD machines located at the patients' homes or the in-center APD machines located inside facilities 100*a*, 100*b* and 100*c*. The APD machines and/or other equipment located anywhere on system 10, 110, including inside facilities 100*a*, 100*b* and 100*c*, may also be operated in a service mode for service personnel to access, diagnose and troubleshoot onsite and/or remotely. A service technician can also remotely investigate and retrieve the data files stored on the APD machines and/or other equipment, located anywhere on system 10, 110, including inside facilities 100*a*, 100*b* and 100*c*, to determine a cause of machine error.

While systems 10 and 110 assume that the patients have home dialysis machines 550 and Internet access to portals 524 and 560, it is also envisioned that the present disclosure could be used in developing countries and other areas in which people need access to renal therapy but do not have access to or the means for home APD machine 550 or the Internet. Systems 10 and 110 therefore also include and support walk-up patients located in areas that do not have home dialysis equipment, service personnel support, system hub support, or access to a web portal. A facility 100 here instead provides a computer and software for accepting and verifying a customer and/or a prescription.

For example, if a patient presents a facility 100 with a paper prescription, the facility can place a call to the prescribing physician's hospital or clinic to verify the pre- scription provided by the patient. A licensed physician can also contact the facility 100 directly on behalf of a patient and provide a prescription prior to the patient's visit to the facility to expedite treatment. If a prescription is written by a hospital or clinic associated with the facility 100, the facility may already have access to the patient's records upon the patient's arrival at the facility. Those of ordinary skill in the art will understand that there are additional methods of receiving a patient's prescription that could be utilized by a facility, e.g., in a developing country, according to the present disclosure.

In some cases, such as when a prescription is provided directly to the facility by a licensed physician or when the prescription is prescribed by a hospital or clinic associated with the facility, the facility can verify the prescription simultaneously with the reception of the prescription. In other cases, such as when patients produce the prescriptions themselves at the facility 100, the verification process occurs after the facility receives the prescription. In the case of repeat patients at the facility, the facility may be able to keep a patient's prescription on electronic or paper file and recall the prescription each time the patient enters the facility for treatment after the prescription has been verified during an initial visit.

After facility 100 has verified the patient's prescription, the facility knows the type and amount of dialysis solution as well as any disposable items needed for same. Each facility 100 therefore stores a plurality of peritoneal dialysis solutions of varying chemical concentrations and associated disposables to meet the needs of different patients, having different residual renal function and toxin transport charac- teristics. Dispensing the specific amount of the prescribed dialysis solution for each patient can be accomplished in a number of ways, several of which are described below.

Additional Aspects of the Present Disclosure

Aspects of the subject matter described herein may be useful alone or in combination with any one or more of the other aspect described herein. Without limiting the forego- ing description, in a first aspect of the present disclosure, a method of treating peritoneal dialysis patients includes: providing a plurality of different peritoneal dialysis solutions at a single location; accepting a patient at the single location; receiving a prescription for the patient; selecting one of the peritoneal dialysis solutions based on the prescription; and enabling the patient to undergo a peritoneal dialysis treat- ment using the selected peritoneal dialysis solution.

In accordance with a second aspect of the present disclo- sure, which may be used in combination with any other aspect or combination of aspects listed herein, the receiving includes accepting the prescription.

In accordance with a third aspect of the present disclosure, which may be used in combination with any other aspect or combination of aspects listed herein, the receiving includes recalling the prescription.

In accordance with a fourth aspect of the present disclo- sure, which may be used in combination with any other aspect or combination of aspects listed herein, the receiving includes verifying the prescription.

In accordance with a fifth aspect of the present disclosure, which may be used in combination with any other aspect or combination of aspects listed herein, the enabling includes providing the patient with a peritoneal dialysis machine and a cassette.

In accordance with a sixth aspect of the present disclosure, which may be used in combination with any other aspect or combination of aspects listed herein, the enabling includes providing a continuous ambulatory peritoneal dialysis catheter.

In accordance with a seventh aspect of the present disclosure, which may be used in combination with any other aspect or combination of aspects listed herein, the enabling includes providing access to a multi-treatment container of the selected peritoneal dialysis solution.

In accordance with an eighth aspect of the present disclosure, which may be used in combination with the seventh aspect and any other aspect or combination of aspects listed herein, the enabling includes metering an amount of the selected peritoneal dialysis solution to the patient, the amount specified by the prescription.

In accordance with a ninth aspect of the present disclosure, which may be used in combination with the eighth aspect any other aspect or combination of aspects listed herein, the selected peritoneal dialysis solution is provided in a container and in a volume according to the patient.

In accordance with a tenth aspect of the present disclosure, which may be used in combination with any other aspect or combination of aspects listed herein, the enabling includes allowing the patient to manually drain spent dialysis fluid.

In accordance with an eleventh aspect of the present disclosure, which may be used in combination with any other aspect or combination of aspects listed herein, a method of enabling peritoneal dialysis for multiple persons in a single location includes: providing multiple dialysis solutions of varying concentrations at the single location; accepting a person who is a peritoneal dialysis patient at a clinic or hospital that is different from the location; and matching the person to one of the peritoneal dialysis solutions, wherein the person may then use the matched peritoneal dialysis solution in a peritoneal dialysis treatment.

In accordance with a twelfth aspect of the present disclosure, which may be used in combination with the eleventh aspect and any other aspect or combination of aspects listed herein, the person is verified by accessing information provided by the clinic or hospital.

In accordance with a thirteenth aspect of the present disclosure, which may be used in combination with the eleventh aspect any other aspect or combination of aspects listed herein, the peritoneal dialysis solution is matched based on a prescription provided by the clinic or hospital.

In accordance with a fourteenth aspect of the present disclosure, which may be used in combination with the eleventh aspect any other aspect or combination of aspects listed herein, accepting the person includes entering information provided by the person and obtaining the matched peritoneal dialysis solution based on the entered information.

In accordance with an fifteenth aspect of the present disclosure, which may be used in combination with any other aspect or combination of aspects listed herein, a method of enabling peritoneal dialysis self-treatment for multiple persons in a single location includes: providing a plurality of peritoneal dialysis machines capable of dispensing dialysis solutions of varying concentrations; and matching a person to a dialysis solution based on a prescription provided by the person, wherein the person may then use one of the peritoneal dialysis machines to perform a peritoneal dialysis treatment.

In accordance with a sixteenth aspect of the present disclosure, which may be used in combination with the fifteenth aspect and any other aspect or combination of aspects listed herein, the prescription is provided via a data storage device.

In accordance with an seventeenth aspect of the present disclosure, which may be used in combination with any other aspect or combination of aspects listed herein, a facility for providing peritoneal dialysis exchanges for multiple peritoneal dialysis patients includes: a plurality of peritoneal dialysis solutions of varying concentrations; and a system configured to accept information from a patient concerning a treatment prescribed for the patient, and wherein the treatment prescribes one of the dialysis solutions and the patient can perform a peritoneal dialysis exchange at the facility using the prescribed peritoneal dialysis solution.

In accordance with an eighteenth aspect of the present disclosure, which may be used in combination with any other aspect or combination of aspects listed herein, a walk-in facility for peritoneal dialysis patients includes: a plurality of peritoneal dialysis machines containing dialysis solutions of varying concentrations; and a means of accepting and verifying a prescription from a patient, wherein the prescription can be matched to a dialysis solution and the patient can perform self-treatment at the facility.

In accordance with a nineteenth aspect of the present disclosure, which may be used in combination with the eighteenth aspect and any other aspect or combination of aspects listed herein, the treatment is prescribed by a hospital or clinic associated with the facility.

In accordance with a twentieth aspect of the present disclosure, which may be used in combination with the eighteenth aspect and any other aspect or combination of aspects listed herein, the treatment is prescribed by a hospital or clinic under different ownership than the facility.

In accordance with a twenty-first aspect of the present disclosure, which may be used in combination with any other aspect or combination of aspects listed herein, a peritoneal dialysis system includes: a reusable fill container; a reusable drain container; and a reusable continuous ambulatory peritoneal dialysis ("CAPD") set configured and arranged to be fluidly connected to at least one of the reusable fill container or the reusable drain container.

In accordance with a twenty-second aspect of the present disclosure, which may be used in combination with the twenty-first aspect and any other aspect or combination of aspects listed herein, the reusable fill container and the reusable drain container are configured to be mated together as a unit for manual transportation.

In accordance with a twenty-third aspect of the present disclosure, which may be used in combination with the twenty-first aspect and any other aspect or combination of aspects listed herein, at least one of the reusable fill container and the reusable drain container is rigid or semi-rigid.

In accordance with a twenty-fourth aspect of the present disclosure, which may be used in combination with the twenty-first aspect and any other aspect or combination of aspects listed herein, the reusable fill container or the reusable drain container includes a handle for manually transporting the containers when mated together to form a unit.

In accordance with a twenty-fifth aspect of the present disclosure, which may be used in combination with the twenty-first aspect and any other aspect or combination of aspects listed herein, the reusable fill container is labeled with a prescribed type of peritoneal dialysis ("PD") solution.

In accordance with a twenty-sixth aspect of the present disclosure, which may be used in combination with the twenty-first aspect and any other aspect or combination of aspects listed herein, the reusable fill container is filled with a prescribed type of peritoneal dialysis ("PD") solution.

In accordance with a twenty-seventh aspect of the present disclosure, which may be used in combination with the twenty-sixth aspect and any other aspect or combination of aspects listed herein, the system includes a patient treatment facility, and which is configured such that the reusable fill container is filled with the prescribed PD solution at a location remote from the patient treatment facility.

In accordance with a twenty-eighth aspect of the present disclosure, which may be used in combination with the twenty-sixth aspect and any other aspect or combination of aspects listed herein, the system includes a patient treatment facility, and which is configured such that the reusable fill container is filled with the prescribed PD solution at the patient treatment facility.

In accordance with a twenty-ninth aspect of the present disclosure, which may be used in combination with the twenty-eighth aspect and any other aspect or combination of aspects listed herein, the peritoneal dialysis system of claim 7, which is configured such that the PD solution is prepared at the treatment facility before the reusable fill container is filled with the PD solution.

In accordance with a thirtieth aspect of the present disclosure, which may be used in combination with the twenty-eighth aspect and any other aspect or combination of aspects listed herein, the reusable fill container is provided initially with a concentrate and then mixed with purified water at the treatment facility.

In accordance with a thirty-first aspect of the present disclosure, which may be used in combination with the twenty-eighth aspect and any other aspect or combination of aspects listed herein, the system is configured such that the fill container and the PD solution are subjected to a sterilization procedure at the patient treatment facility prior to delivery to a patient.

In accordance with a thirty-second aspect of the present disclosure, which may be used in combination with the twenty-eighth aspect and any other aspect or combination of aspects listed herein, the system includes a sterilization device at a patient treatment location of the patient treatment facility, the fill container and the PD solution subjected to the sterilization device after delivery to a patient.

In accordance with a thirty-third aspect of the present disclosure, which may be used in combination with the twenty-first aspect and any other aspect or combination of aspects listed herein, the reusable fill container includes a valved pouring spout.

In accordance with a thirty-fourth aspect of the present disclosure, which may be used in combination with the twenty-first aspect and any other aspect or combination of aspects listed herein, the reusable CAPD set is provided in a pouch, and wherein the fill or drain container includes structure for releasably holding the pouch.

In accordance with a thirty-fifth aspect of the present disclosure, which may be used in combination with the thirty-fourth aspect and any other aspect or combination of aspects listed herein, the pouch is resealable.

In accordance with a thirty-sixth aspect of the present disclosure, which may be used in combination with the twenty-first aspect and any other aspect or combination of aspects listed herein, the reusable CAPD set is provided in a pouch, and which includes a replacement patient transfer set cap provided in the pouch.

In accordance with a thirty-seventh aspect of the present disclosure, which may be used in combination with the twenty-first aspect and any other aspect or combination of aspects listed herein, the reusable CAPD set includes a fill line and a drain line in fluid communication with a patient line.

In accordance with a thirty-eighth aspect of the present disclosure, which may be used in combination with the twenty-first aspect and any other aspect or combination of aspects listed herein, the CAPD set includes a manual valve that the user can manipulate to switch from a drain mode, to a flush mode, to a fill mode.

In accordance with a thirty-ninth aspect of the present disclosure, which may be used in combination with the twenty-first aspect and any other aspect or combination of aspects listed herein, the system is configured such that three caps from the CAPD set, one cap from the fill container, one cap from the drain container, and one cap from the pouch are subjected to a sterilization process after treatment.

In accordance with a fortieth aspect of the present disclosure, which may be used in combination with any other aspect or combination of aspects listed herein, a peritoneal dialysis system includes: a reusable fill container; and a reusable drain container, wherein the reusable fill container and the reusable drain container are configured to be mated together as a unit for manual transportation.

In accordance with a forty-first aspect of the present disclosure, which may be used in combination with the fortieth aspect and any other aspect or combination of aspects listed herein, the disposable CAPD set is provided in a disposable pouch subjected to a sterilization process.

In accordance with a forty-second aspect of the present disclosure, which may be used in combination with any other aspect or combination of aspects listed herein, a peritoneal dialysis system includes: a fill container; and an energizing unit that removably accepts the fill container, the energizing unit including a sterilization source so configured and arranged relative to the fill container when accepted by the energizing unit to place fluid within the fill container in a physiologically safe condition for delivery to the peritoneal cavity of a patient.

In accordance with a forty-third aspect of the present disclosure, which may be used in combination with the forty-second aspect and any other aspect or combination of aspects listed herein, the fluid is water or dialysate.

In accordance with a forty-fourth aspect of the present disclosure, which may be used in combination with the forty-second aspect and any other aspect or combination of aspects listed herein, the fluid is water, and which includes a packet of additives which when mixed with the water form dialysate suitable for delivery to the peritoneal cavity of the patient.

In accordance with a forty-fifth aspect of the present disclosure, which may be used in combination with the forty-fourth aspect and any other aspect or combination of aspects listed herein, the fill container provides an opening to receive the additives from the packet.

In accordance with a forty-sixth aspect of the present disclosure, which may be used in combination with the forty-second aspect and any other aspect or combination of aspects listed herein, the sterilizing source includes a plurality of ultraviolet ("UV") lights.

In accordance with a forty-seventh aspect of the present disclosure, which may be used in combination with the forty-second aspect and any other aspect or combination of aspects listed herein, the sterilizing source includes a plurality of panels arranged to be adjacent to a plurality of sides of the fill container when accepted by the energizing unit.

In accordance with a forty-eighth aspect of the present disclosure, which may be used in combination with the forty-second aspect and any other aspect or combination of aspects listed herein, the energizing unit includes a measurement device for determining how much fluid has been delivered to the container.

In accordance with a forty-ninth aspect of the present disclosure, which may be used in combination with the forty-eighth aspect and any other aspect or combination of aspects listed herein, the measurement device includes a weigh scale.

In accordance with a fiftieth aspect of the present disclosure, which may be used in combination with the forty-second aspect and any other aspect or combination of aspects listed herein, the energizing unit includes a heater positioned and arranged to heat fluid within the fill container when accepted by the energizing unit.

In accordance with a fifty-first aspect of the present disclosure, which may be used in combination with the forty-second aspect and any other aspect or combination of aspects listed herein, the peritoneal dialysis system includes at least one valve manueverably connected to the energizing unit so as to be selectively operable with at least one of an inlet or an outlet of the fill container.

In accordance with a fifty-second aspect of the present disclosure, which may be used in combination with the fifty-first aspect and any other aspect or combination of aspects listed herein, the fill container includes an inlet tube and an outlet tube, and wherein the at least one valve includes a fill valve operable with the inlet tube and a dispense valve operable with the outlet tube.

In accordance with a fifty-third aspect of the present disclosure, which may be used in combination with the forty-second aspect and any other aspect or combination of aspects listed herein, the energizing unit includes a control unit and at least one sensor providing feedback to the control unit.

In accordance with a fifty-fourth aspect of the present disclosure, which may be used in combination with the fifty-third aspect and any other aspect or combination of aspects listed herein, the at least one sensor is removably coupled to the fill container.

In accordance with a fifty-fifth aspect of the present disclosure, which may be used in combination with the forty-second aspect and any other aspect or combination of aspects listed herein, the peritoneal dialysis system includes a sterilization unit separate from the energizing unit, the sterilizing unit sized to accept a peritoneal dialysis set and configured to place the set into a physiologically safe condition to deliver fluid to the peritoneal cavity of the patient.

In accordance with a fifty-sixth aspect of the present disclosure, which may be used in combination with the fifty-fifth aspect and any other aspect or combination of aspects listed herein, the sterilizing unit used ultraviolet ("UV") radiation to place the peritoneal dialysis set into the physiologically safe condition.

In accordance with a fifty-seventh aspect of the present disclosure, which may be used in combination with the fifty-fifth aspect and any other aspect or combination of aspects listed herein, the peritoneal dialysis system includes a disinfection unit separate from the energizing unit and the sterilization unit, the disinfection unit configured to disinfect the peritoneal dialysis set prior to placing the set into the physiologically safe condition using the sterilizing unit.

In accordance with a fifty-eighth aspect of the present disclosure, which may be used in combination with the fifty-seventh aspect and any other aspect or combination of aspects listed herein, the disinfection unit is a hot water disinfection unit.

In accordance with a fifty-ninth aspect of the present disclosure, which may be used in combination with the forty-second aspect and any other aspect or combination of aspects listed herein, the peritoneal dialysis system includes a fluid purification unit separate from the energizing unit for purifying the fluid prior to placing the fluid into the physiologically safe condition using the energizing unit.

In accordance with a sixtieth aspect of the present disclosure, which may be used in combination with the fifty-ninth aspect and any other aspect or combination of aspects listed herein, the fluid purification unit uses at least one process selected from the group consisting of: distillation, reverse osmosis, carbon filtering, ultraviolet ("UV") radiation, electro-deionization, ultrafiltering or any combination thereof.

In accordance with a sixty-first aspect of the present disclosure, which may be used in combination with any other aspect or combination of aspects listed herein, a peritoneal dialysis ("PD") method includes: providing a dialysate additive packet, a disinfected PD set and a drain container to a patient; at a patient station, providing a sterilizing unit and an energizing unit housing a fill container; enabling the patient to place the disinfected PD set into the sterilizing unit; causing the sterilizing unit to place the disinfected PD set into a physiologically safe condition for use with the patient; enabling the patient to empty the contents of the additive packet into the fill container housed by the energizing unit; causing the fill container to fill with purified water and mix the additive contents with the purified water to form PD dialysate; enabling the patient to drain effluent fluid to the drain container using the physiologically safe PD set; heating and sterilizing the PD dialysate to form a physiologically safe and properly heated dialysate; and when the effluent fluid drain is completed and the dialysate is physiologically safe and properly heated, filling the patient from the fill container, through the PD set with the physiologically safe and properly heated dialysate.

In accordance with a sixty-second aspect of the present disclosure, which may be used in combination with the sixty-first aspect and any other aspect or combination of aspects listed herein, the PD method includes weighing an amount of effluent fluid drained to the drain container.

In accordance with a sixty-third aspect of the present disclosure, which may be used in combination with the sixty-second aspect and any other aspect or combination of aspects listed herein, the PD method includes weighing an amount of physiologically safe and properly heated dialysate delivered to the patient and subtracting the delivered amount from the drained amount to determine an amount of ultrafiltration ("UF") removed from the patient.

In accordance with a sixty-fourth aspect of the present disclosure, which may be used in combination with the sixty-first aspect and any other aspect or combination of aspects listed herein, the PD method includes enabling the patient to return the used PD set and filled drain container for refurbishment.

In accordance with a sixty-fifth aspect of the present disclosure, which may be used in combination with any other aspect or combination of aspects listed herein, a peritoneal dialysis ("PD") system includes: a peritoneal dialysis set provided to a patient; a disinfection unit configured to disinfect the peritoneal dialysis set prior to providing the set to the patient; a sterilization unit sized to accept the peritoneal dialysis set and configured to place the set into a physiologically safe condition to deliver fluid to the peritoneal cavity of the patient; a fill container; and an energizing unit that removably accepts the fill container, the energizing unit including a sterilization source so configured and arranged relative to the fill container when accepted by the energizing unit to place fluid within the fill container in a physiologically safe condition for delivery to the peritoneal cavity of a patient.

In accordance with a sixty-sixth aspect of the present disclosure, which may be used in combination with the sixty-fifth aspect and any other aspect or combination of aspects listed herein, the system is provided within a single facility.

In accordance with a sixty-seventh aspect of the present disclosure, which may be used in combination with any other aspect or combination of aspects listed herein, a peritoneal dialysis method includes: providing a reusable fill container, a reusable drain container, and a reusable continuous ambulatory peritoneal dialysis ("CAPD") set to a patient; enabling the patient to perform a CAPD treatment using the fill container, drain container, and CAPD set; receiving the fill container, drain container, and CAPD set back from the patient after the CAPD treatment; and refurbishing the fill container, drain container, and CAPD set for use with a subsequent CAPD treatment.

In accordance with a sixty-eighth aspect of the present disclosure, any of the structure and functionality illustrated and described in connection with FIGS. 1 to 15 may be used in combination with any one or more or all of the preceding aspects.

The invention is claimed as follows:

1. A peritoneal dialysis system for providing peritoneal dialysis exchanges to peritoneal dialysis patients at a facility located outside of homes of the peritoneal dialysis patients, the peritoneal dialysis system comprising:
   a plurality of patient lines, each patient line configured to provide peritoneal dialysis solution to a different peritoneal dialysis patient;
   a plurality of solution tanks each containing one of a plurality of different peritoneal dialysis solutions provided at the facility, the plurality of different peritoneal dialysis solutions including varying chemical concentrations for providing peritoneal dialysis exchanges for the peritoneal dialysis patients, the plurality of solution tanks each connected to the plurality of patient lines via respective dispensers, each dispenser including at least:
      a pressure regulator configured to reduce a pressure of the peritoneal dialysis solution from the respective solution tank before the peritoneal dialysis solution reaches the respective patient line,
      a fill valve located downstream from the pressure regulator, and
      a metering device located downstream from the fill valve, an output from the metering device causing the fill valve to close when the peritoneal dialysis solution reaches a predetermined volume within the metering device;
   a prescription for a peritoneal dialysis patient of the peritoneal dialysis patients, the prescription including information concerning a treatment prescribed for the peritoneal dialysis patient including the predetermined volume;
   at least one computer located at the facility, the at least one computer configured to select one of the peritoneal dialysis solutions according to the prescription for the peritoneal dialysis patient; and
   a patient station provided at the facility for the peritoneal dialysis patient to perform a peritoneal dialysis exchange according to the prescription, using one of the plurality of patient lines connected to the solution tank comprising the selected peritoneal dialysis solution.

2. The peritoneal dialysis system of claim 1, wherein the peritoneal dialysis exchange is a continuous ambulatory peritoneal dialysis ("CAPD") exchange.

3. The peritoneal dialysis system of claim 1, wherein the at least one computer is configured to retrieve the prescription for the peritoneal dialysis patient from a computer readable medium carried by the peritoneal dialysis patient.

4. The peritoneal dialysis system of claim 1, wherein the at least one computer is configured to communicate with a hospital or clinic issuing the prescription for the peritoneal dialysis patient.

5. The peritoneal dialysis system of claim 1, wherein the at least one computer is configured to send data from the facility to a hospital or clinic.

6. The peritoneal dialysis system of claim 1, wherein the at least one computer is configured to verify information concerning the prescription for the peritoneal dialysis patient.

7. The peritoneal dialysis system of claim 1, further comprising a disposable set provided at the facility for the peritoneal dialysis patient to perform the peritoneal dialysis exchange.

8. The peritoneal dialysis system of claim 7, wherein the disposable set is configured to be recyclable and/or reusable after the peritoneal dialysis exchange.

9. The peritoneal dialysis system of claim 1, wherein the plurality of solution tanks comprises different dextrose or glucose level peritoneal dialysis solutions.

10. The peritoneal dialysis system of claim 1, wherein the selected peritoneal dialysis solution is prepared on demand and includes purified water and powdered additives dissolved in the purified water.

11. The peritoneal dialysis system of claim 1, wherein the facility further includes a sterilizing unit for sterilizing a CAPD set for use with one of the plurality of solution tanks.

12. The peritoneal dialysis system of claim 11, wherein the sterilizing unit includes a plurality of ultraviolet ("UV") lights.

13. The peritoneal dialysis system of claim 11, wherein the sterilizing unit is located at the patient station.

14. The peritoneal dialysis system of claim 1, wherein the patient station is selected from a plurality of patient stations provided at the facility.

* * * * *